US012797633B2

(12) United States Patent
Fang

(10) Patent No.: US 12,797,633 B2
(45) Date of Patent: Nov. 17, 2026

(54) SKIN TREATMENT APPARATUS

(71) Applicant: SHENZHEN ULIKE SMART ELECTRONICS CO., LTD., Shenzhen (CN)

(72) Inventor: Shaoqing Fang, Shenzhen (CN)

(73) Assignee: SHENZHEN ULIKE SMART ELECTRONICS CO., LTD., Shenzhen (CN)

( * ) Notice: Subject to any disclaimer, the term of this patent is extended or adjusted under 35 U.S.C. 154(b) by 339 days.

(21) Appl. No.: 18/399,703

(22) Filed: Dec. 29, 2023

(65) Prior Publication Data

US 2024/0390696 A1 Nov. 28, 2024

(30) Foreign Application Priority Data

May 25, 2023 (CN) ......................... 202310606901.4

(51) Int. Cl.
*A61N 5/06* (2006.01)
*A61N 5/00* (2006.01)

(52) U.S. Cl.
CPC ...... *A61N 5/0616* (2013.01); *A61N 2005/007* (2013.01); *A61N 2005/0632* (2013.01);
(Continued)

(58) Field of Classification Search
None
See application file for complete search history.

(56) References Cited

U.S. PATENT DOCUMENTS 8,518,027 B2 * 8/2013 Weckwerth .......... A61N 5/0616 606/4
2011/0098789 A1 * 4/2011 Weckwerth .......... A61N 5/0616 607/88
(Continued)

FOREIGN PATENT DOCUMENTS

CN 207804371 U 9/2018
CN 110755153 A 2/2020
(Continued)

OTHER PUBLICATIONS

Machine translation of CN 112451087 (Year: 2021).*
(Continued)

*Primary Examiner* — James Kish

(57) ABSTRACT

The present disclosure provides a skin treatment apparatus, including: a housing component defined with an accommodation cavity and a light outlet communicated with each other; a light emitting component disposed in the accommodation cavity, light generated from the light emitting component passing through the light outlet and being irradiated to a to-be-treated skin; a cold compress component disposed on the housing component and located at the light outlet, configured to cool the to-be-treated skin; and a heat dissipation component including a thermal conductive structure and a heat dissipation sheet component, the thermal conductive structure including a first thermal conductive section and a second thermal conductive section, the cold compress component being thermally connected to the first thermal conductive section, and at least part of the heat dissipation sheet component being thermally connected to the second thermal conductive section.

14 Claims, 35 Drawing Sheets

(52) U.S. Cl.
CPC ................. *A61N 2005/0644* (2013.01); *A61N 2005/0653* (2013.01)

(56) References Cited

U.S. PATENT DOCUMENTS

| | | | | |
|---|---|---|---|---|
| 2021/0393014 A1* | 12/2021 | Pan | .................... | A45D 26/0061 |
| 2022/0118278 A1* | 4/2022 | Pan | ........................ | A61B 18/18 |
| 2022/0192745 A1* | 6/2022 | Pan | ........................ | A61B 18/18 |
| 2022/0346871 A1* | 11/2022 | Duan | ..................... | A61B 18/18 |
| 2023/0129185 A1 | 4/2023 | Pan | | |
| 2024/0261022 A1* | 8/2024 | Jones | ..................... | A61B 18/18 |

FOREIGN PATENT DOCUMENTS

| | | | | | |
|---|---|---|---|---|---|
| CN | 111529055 | A | * | 8/2020 | ........... A61N 5/0616 |
| CN | 111685869 | A | | 9/2020 | |
| CN | 111700725 | A | | 9/2020 | |
| CN | 211381746 | U | | 9/2020 | |
| CN | 112168344 | A | | 1/2021 | |
| CN | 212308030 | U | | 1/2021 | |
| CN | 112451087 | A | * | 3/2021 | ............... A61F 7/00 |
| CN | 112484336 | A | | 3/2021 | |
| CN | 214908023 | U | | 11/2021 | |
| CN | 215018854 | U | | 12/2021 | |
| CN | 215821349 | U | | 2/2022 | |
| CN | 216455274 | U | * | 5/2022 | |
| CN | 217612532 | U | | 10/2022 | |
| CN | 217745370 | U | | 11/2022 | |
| CN | 115770103 | A | | 3/2023 | |
| CN | 220141800 | U | | 12/2023 | |
| EP | 3925561 | A1 | * | 12/2021 | ............. A61B 18/18 |
| EP | 4008285 | A1 | | 6/2022 | |
| EP | 4424261 | A1 | * | 9/2024 | ............. A61B 18/22 |
| JP | 2010142612 | A | | 7/2010 | |
| JP | 2021007750 | A | * | 1/2021 | ........... A61N 5/0616 |
| KR | 20220023866 | A | | 3/2022 | |
| WO | WO-2011056472 | A1 | * | 5/2011 | ........... A61B 18/203 |
| WO | WO-2021003950 | A1 | * | 1/2021 | ............. A61F 7/007 |
| WO | WO-2022041034 | A1 | * | 3/2022 | ............. A61B 18/20 |
| WO | WO-2022082837 | A1 | * | 4/2022 | ............... A61N 5/06 |
| WO | WO-2024038286 | A1 | * | 2/2024 | ........... A61N 5/0616 |

OTHER PUBLICATIONS

Machine Translation of WO-2021003950-A1 (Year: 2021).*

Rao R. Tumara, Device and System Packaging Technology and Applications (2nd edition of the original book), published by Mechanical Industry Presssociety, issued Jun. 30, 2021, pp. 97-101.

* cited by examiner

SKIN TREATMENT APPARATUS

TECHNICAL FIELD

The present disclosure relates to the technical field of skin treatment apparatus, and in particular, to a skin treatment apparatus.

BACKGROUND

In related art, a skin treatment apparatus generally includes a housing and a thermal conductive component, a cold compress component, a light emitting component, and a heat dissipation sheet component that are all arranged on the housing. The cold compress component is disposed at the front end of the housing to cool human skin. The light emitting component is configured to emit light which passes through the front end of the housing and then irradiate to a skin to be treated so as to perform light therapy (such as hair removal, skin rejuvenation) on the skin to be treated.

In related art, the heat dissipation sheet component is generally disposed on the side of the light emitting component away from the cold compress component. That is, the cold compress component, the light emitting component, and the heat dissipation sheet component are arranged along a straight line, and the cold compress component is thermally connected to the heat dissipation sheet component by a thermal conductive component.

However, the above arrangement of the heat dissipation sheet component needs a long length of thermal conductive component and accordingly resulting a long thermal conductive path, which not only affects the thermal conductive efficiency of the thermal conductive component, but also leads to a poor heat dissipation effect of the heat dissipation sheet component.

SUMMARY

A main objective of the present disclosure is to provide a skin treatment apparatus, to solve the problem in related art that the length of the thermal conductive component of the skin treatment apparatus is relatively long and the heat dissipation efficiency of the heat dissipation sheet component is affected.

To achieve the foregoing objective, the present disclosure provides a skin treatment apparatus, including:

- a housing component defined with an accommodation cavity and a light outlet communicated with each other;
- a light emitting component disposed in the accommodation cavity, light generated from the light emitting component passing through the light outlet and being irradiated to a skin to be treated;
- a cold compress component disposed on the housing component and located at the light outlet, the cold compress component being configured to cool the skin to be treated or a skin in a vicinity of the skin to be treated; and
- a heat dissipation component including a thermal conductive structure and a heat dissipation sheet component, the thermal conductive structure including a first thermal conductive section and a second thermal conductive section, the cold compress component being thermally connected to the first thermal conductive section, and at least part of the heat dissipation sheet component being thermally connected to the second thermal conductive section.

In some embodiments, the housing component is provided with a housing air outlet part, and at least part of the heat dissipation component is disposed corresponding to the housing air outlet part; and/or, the thermal conductive structure extends along a light output direction of the light emitting component; and/or, the thermal conductive structure is provided with a capillary flow channel and a thermal conductive medium disposed in the capillary flow channel, the first thermal conductive section is an evaporation section, and the second thermal conductive section is a condensing section.

In some embodiments, the housing component includes a housing. The light outlet is located at a first end of the housing, and the first end of the housing is provided with a necking section.

In some embodiments, a height of at least part of the heat dissipation sheet component gradually reduces along the light output direction of the light emitting component, to fit the necking section.

In some embodiments, the heat dissipation sheet component includes a first side surface and a second side surface. The first side surface faces the first end of the housing, the second side surface faces away from the light emitting component, and a joint of the first side surface and the second side surface is defined with a missing corner, and the missing corner is disposed corresponding to the necking section.

In some embodiments, the heat dissipation sheet component further includes a transition surface. The first side surface is connected to the second side surface by the transition surface. The transition surface and the first side surface form an included angle, and the transition surface and the second side surface form an included angle. The missing corner is formed between the transition surface and the housing.

In some embodiments, the transition surface is an inclined surface or a curved surface. Alternatively, the transition surface includes a first sub-transition surface and a second sub-transition surface which forms an included angle with first sub-transition surface. The first sub-transition surface is connected to the first side surface, and the second sub-transition surface is connected to the second side surface. The first sub-transition surface is a first flat surface or a first curved surface, and the second sub-transition surface is a second flat surface or a second curved surface.

In some embodiments, the heat dissipation sheet component includes a plurality of heat dissipation sheets arranged at intervals in a first direction. A first side edge of each heat dissipation sheet forms the first side surface, and a second side edge of each heat dissipation sheet forms the second side surface. Each heat dissipation sheet extends along a second direction. The first direction and the second direction form an included angle, and the second direction is the same as the light output direction of the light emitting component.

In some embodiments, the transition surface includes a first sub-transition surface and a second sub-transition surface which forms an included angle with the first sub-transition surface. The first sub-transition surface is connected to the first side surface, and the second sub-transition surface is connected to the second side surface. Each heat dissipation sheet includes: a heat dissipation sheet body including the first side surface, the second side surface, and the second sub-transition surface; and a flange disposed on the heat dissipation sheet body and forming an included angle with the heat dissipation sheet body, a surface of the flange away from the heat dissipation sheet body forming the first sub-transition surface. A ventilation channel is formed between the heat dissipation sheet bodies of two adjacent heat dissipation sheets, and the flange of each heat dissipation sheet is in contact with an adjacent heat dissipation sheet and configured to block at least part of the ventilation channel, so as to form an air outlet at two sides of the flange.

In some embodiments, the heat dissipation sheet component further includes: a blocking part disposed on a part of a third side edge of at least one heat dissipation sheet for blocking at least part of the ventilation channel. A surface of the blocking part away from the light emitting component forms the first sub-transition surface, to form the air outlet at two sides of the blocking part. The other part of the third side edge of at least one heat dissipation sheet forms the second sub-transition surface.

In some embodiments, a ventilation channel is formed between two adjacent heat dissipation sheets. The heat dissipation sheet component is defined with an air inlet and an air outlet. The air inlet is communicated with the air outlet through the ventilation channel. The air inlet is located on a side of the heat dissipation sheet component away from the first side surface, and the air outlet is located on at least one of the first side surface, the second side surface, and the missing corner.

In some embodiments, the air outlet includes a first sub-air outlet defined in the first side surface and a second sub-air outlet defined in the second side surface and/or the missing corner; and/or, a ratio of a length of the missing corner to a length of the heat dissipation sheet is greater than or equal to 0.32 and less than or equal to 0.55; and/or, a ratio of a width of the missing corner to a width of the heat dissipation sheet is greater than or equal to 0.36 and less than or equal to 0.6; and/or, the heat dissipation sheet component and the light emitting component are located on two sides of the thermal conductive structure.

In some embodiments, the light emitting component includes a light emitting member and a filter. A distance between the first side surface and the filter is less than or equal to 9 millimeters (mm) in the light output direction of the light emitting component.

In some embodiments, the housing includes: a first side plate located on a side of the heat dissipation sheet component away from the light emitting component; and a second side plate facing the first side plate. A surface of the first side plate facing the second side surface of the heat dissipation sheet component defines a first extension section, and at least part of the first extension section gradually bends toward the second side plate in the light output direction of the light emitting component, to form at least part of the necking section.

In some embodiments, the housing component further includes: a holder component disposed in the accommodation cavity. The holder component is defined with a first mounting cavity and a second mounting cavity. The light emitting component is disposed in the first mounting cavity, and the heat dissipation sheet component is disposed in the second mounting cavity. At least part of a projection of the second mounting cavity on the first mounting cavity is within the first mounting cavity in a length direction of the housing.

In some embodiments, the holder component includes a first ventilation surface facing the first extension section, and at least part of the first ventilation surface is gradually close to the second side plate along the light output direction of the light emitting component, to fit the first extension section. The first ventilation surface is defined with a first air vent communicated with the second mounting cavity.

In some embodiments, the holder component includes a heat dissipation sheet holder and a light emitting side holder connected to each other, where the heat dissipation sheet holder is located on one side of the thermal conductive structure, and the light emitting side holder is located on the other side of the thermal conductive structure. The light emitting side holder is provided with the first mounting cavity. The heat dissipation sheet holder is provided with the second mounting cavity, the first ventilation surface, and a mounting port. The heat dissipation sheet component is mounted in the second mounting cavity through the mounting port.

In some embodiments, the skin treatment apparatus further includes: a fan disposed in the accommodation cavity and located on a side of the heat dissipation sheet component away from the outlet light. The heat dissipation sheet holder is defined with a second air vent. An air outlet of the fan is communicated with the second mounting cavity through the second air vent.

In some embodiments, the heat dissipation sheet holder includes a first holder. The first holder includes a first support part, a first side support part, a second support part, and a second side support part connected with each other successively. The first support part and the second support part face each other and are connected to the second side support part. The first side support part faces the second side support part. The second support part is disposed away from the light outlet with respect to the first support part. The first support part, the first side support part, the second support part, and the second side support part enclose to form the second mounting cavity and the first air vent. The side walls of the first support part, the first side support part, the second support part, and the second side support part away from the light emitting component form the first ventilation surface. The second support part, the first side support part, and the second side support part enclose to form the second air vent.

In some embodiments, the first support part includes a first support plate disposed laterally, the second support part includes a second support plate disposed laterally, the first side support part includes a third support plate disposed longitudinally, and the second side support part includes a fourth support plate disposed longitudinally. One end of the second support plate is connected to an inner surface of the third support plate, and the other end of the second support plate is connected to an inner surface of the fourth support plate. A side edge of the second support plate facing the fan, a side edge of the third support plate facing the fan, and a side edge of the fourth support plate facing the fan enclose to form the second air vent. A side edge of the first support plate facing the third support plate, the third support plate, the fourth support plate, and a side edge of the second support plate facing the first support plate enclose to form the first air vent.

In some embodiments, the housing component is provided with a housing air outlet part, a side edge of the first support plate away from the fan, a side edge of the third support plate away from the fan, and a side edge of the fourth support plate away from the fan enclose to form a third air vent communicated with the second mounting cavity and the housing air outlet part; and/or, the first support plate faces the first sub-transition surface of the heat dissipation sheet component; and/or, at least part of a side edge of the third support plate away from the light emitting component and at least part of a side edge of the fourth support plate away from the light emitting component gradually bend toward the second side plate in the light output direction of the light emitting component, to allow at least part of the first ventilation surface to gradually bend toward the second side plate; and/or, an inner side wall of the third support plate is provided with a first air blocking protrusion part, the first air blocking protrusion part is disposed close to a side edge of the second support plate away from the light emitting component, and the first air blocking protrusion part extends along an extension direction of the side edge; and/or, an inner side wall of the fourth support plate is provided with a second air blocking protrusion part, the second air blocking protrusion part is disposed close to a side edge of the third support plate away from the light emitting component, and the second air blocking protrusion part extends along an extension direction of the side edge; and/or, an inner side wall of the fourth support plate is provided with a third air blocking protrusion part, the third air blocking protrusion part is disposed close to the first support part with respect to the second support part, and the third air blocking protrusion part extends in a direction close to or away from the light emitting component.

In some embodiments, the heat dissipation sheet holder further includes a first outer support part disposed on an outer side wall of the first side support part, the first outer support part is connected to the light emitting side holder. The heat dissipation sheet holder further includes a second outer support part disposed on an outer side wall of the second side support part, the second outer support part is connected to the light emitting side holder.

In some embodiments, the housing component is provided with a housing air outlet part, the first outer support part and the light emitting side holder enclose to form a first ventilation flow channel communicated with the air outlet of the fan and the first mounting cavity, and at least part of the first ventilation flow channel gradually bends toward the side away from the first extension section in the light output direction of the light emitting component; and/or, the second outer support part and the light emitting side holder enclose to form a second ventilation flow channel communicated with the housing air outlet part and the first mounting cavity.

In some embodiments, the first outer support part includes a first air duct plate and a second air duct plate. The first air duct plate is disposed on an outer side wall of the third support plate, the second duct plate is connected to a side edge of the first air duct plate away from the first support plate, and the second air duct plate faces the third support plate. The first air duct plate, the third support plate, and the second air duct plate enclose to form a part of the first ventilation flow channel, at least part of the first air duct plate gradually bends toward the side away from the first extension section in the light output direction of the light emitting component, to allow at least part of the first ventilation flow channel to gradually bend toward the side away from the first extension section; and/or, the second outer support part includes a first flow duct plate and a second flow duct plate, the first flow duct plate is disposed on an outer side wall of the fourth support plate, the second flow duct plate is connected to a side edge of the first flow duct plate away from the second support plate, the second flow duct plate faces the fourth support plate, the second ventilation flow channel is defined with a ventilation through port and a diffuser auxiliary cavity, and the ventilation through port is located on the first flow duct plate; the first flow duct plate, the second flow duct plate, and the fourth support plate enclose to form the diffuser auxiliary cavity, the diffuser auxiliary cavity is communicated with the housing air outlet part, and the diffuser auxiliary cavity is communicated with the first mounting cavity through the ventilation through port; the second outer support part further includes a light-blocking flow guiding part, which is disposed on the fourth support plate and the second flow duct plate, and at least partially covers the ventilation through port.

In some embodiments, the first air duct plate and/or the second air duct plate is provided with a first engagement part that is engaged with the light emitting side holder; and/or, the first flow duct plate and/or the second flow duct plate is provided with a second engagement part that is engaged with the light emitting side holder.

In some embodiments, the cold compress component includes a light transmitting member. The light emitting side holder is further defined with a third mounting cavity located between the first mounting cavity and the light outlet. The light transmitting member is mounted in the third mounting cavity.

In some embodiments, the light emitting side holder includes a second holder and a third holder located between the second holder and the light outlet. The second holder is provided with the first mounting cavity and a holder light outlet. The first mounting cavity is communicated with the light outlet through the holder light outlet. The third holder is connected to the second holder and is provided with the third mounting cavity.

In some embodiments, the second holder includes a first mounting plate, a first side part disposed on one side of the first mounting plate, and a second side part disposed on the other side of the first mounting plate. The first mounting plate faces the light outlet. The first mounting plate, the first side part, and the second side part enclose to form the first mounting cavity. The holder light outlet is formed between the first side part and the second side part.

In some embodiments, the light emitting component includes a light emitting member and a reflector disposed around the light emitting member; the first mounting plate is defined with a mounting insertion hole, the reflector is provided with an insertion pin, and the insertion pin is inserted into the mounting insertion hole; and/or, an inner side surface of the first mounting plate is provided with an abutting protrusion part, and the reflector abuts against the abutting protrusion part, to form a ventilation gap between the reflector and the inner side surface of the first mounting plate.

In some embodiments, the light emitting component further includes a filter disposed between the light emitting member and the light transmitting member, and a sealing structure disposed between the filter and the light transmitting member. The sealing structure is located outside a spot of light irradiated on the filter by the light transmitting member.

In some embodiments, each side of the first mounting cavity is defined with an opening. The third holder includes a first connection support part and a second connection support part extending toward the second holder. The first connection support part and the second connection support part are both connected to the second holder and cover the two openings.

In some embodiments, the second holder further includes a first flow guiding part disposed at one end of the first mounting plate, one end of the first side part, and one end of the second side part, the first flow guiding part cooperates with the heat dissipation sheet holder to form the first ventilation flow channel communicated with the first mounting cavity; and/or, the second holder further includes a second flow guiding part disposed at the other end of the first mounting plate, the other end of the first side part, and the other end of the second side part, the second flow guiding part cooperates with the heat dissipation sheet holder to form the second ventilation flow channel communicated with the first mounting cavity.

In some embodiments, the first flow guiding part includes a first flow guiding side plate, a second flow guiding side plate, and a third flow guiding side plate. The second flow guiding side plate faces the first flow guiding side plate. The third flow guiding side plate is connected to the first flow guiding side plate, the second guide side plate, and the second side part respectively. The first flow guiding side plate, the second flow guiding side plate, and the third flow guiding side plate enclose to form at least part of the first ventilation flow channel.

In some embodiments, at least part of the third flow guiding side plate gradually bends toward the side away from the first extension section along the light output direction of the light emitting component; and/or, the first flow guiding side plate, the second flow guiding side plate, and the third flow guiding side all extend toward the side away from the light outlet; and/or, the first flow guiding part further includes a fourth flow guiding side plate connected with the first flow guiding side plate and the second flow guiding side plate, a surface of the fourth flow guiding side plate facing the third holder is provided with a third engagement part that is engaged with the third holder; and/or, an outer side surface of the second flow guiding side plate is provided with a fourth engagement part that is engaged with the heat dissipation sheet holder.

In some embodiments, the second ventilation flow channel includes a diffuser auxiliary cavity, the part of the second flow guiding part located at the opening of the first mounting cavity is defined with a diffuser cavity and a diffuser hole communicated with each other, and the diffuser cavity is communicated with the diffuser auxiliary cavity through the diffuser hole.

In some embodiments, the second flow guiding part includes: a first diffuser plate connected to the first mounting plate and extending toward a direction away from the light outlet; a second diffuser plate connected to the first diffuser plate and located on a side of the first diffuser plate away from the first mounting plate; a third diffuser plate connected to the first mounting plate, the first diffuser plate, and the second diffuser plate respectively; and a ventilation part connected to the first diffuser plate and the second diffuser plate, the third diffuser plate facing the ventilation part, and the ventilation part being provided with the diffuser hole.

In some embodiments, the ventilation part includes: a first ventilation plate connected to the first diffuser plate and the first side part; a second ventilation plate facing the first ventilation plate; a third ventilation plate connected to the second diffuser plate, the first ventilation plate, and the second ventilation plate respectively; and a fourth ventilation plate facing the third ventilation plate and connected to the first ventilation plate and the second ventilation plate. The first ventilation plate, the second ventilation plate, the third ventilation plate, and the fourth ventilation plate enclose to form the diffuser hole.

In some embodiments, an outer side surface of the second ventilation plate is provided with a fifth engagement part that is engaged with the heat dissipation sheet holder; and/or, an outer side surface of the fourth ventilation plate is provided with a sixth engagement part that is engaged with the third holder; and/or, the diffuser hole has a preset hole depth.

In some embodiments, the skin treatment apparatus further includes a main control board. The second holder further includes: a heat dissipation support plate disposed on a side of the first mounting plate away from the light outlet and connected to the first mounting plate and the first side part. The heat dissipation support plate is provided with a weight reduction hole and a first connection post. The first connection post is located on a side of the heat dissipation support plate away from the heat dissipation component, so that the main control board and the second holder are connected by inserting a fastener into the main control board and the first connection post.

In some embodiments, the skin treatment apparatus further includes a fan holder, which is configured to support the fan. The second flow guiding part further includes: a first support part disposed on the third ventilation plate and extending toward the side away from the light outlet, the first support part being configured to support the heat dissipation sheet holder; and a second support part disposed on the first support part and extending toward the side away from the light outlet, the second support part extending between the fan holder and the main control board and contacting with the fan holder and/or the main control board.

In some embodiments, the second support part includes: a support bar; and a support block, one end of the support bar is connected to the first support part, and the other end of the support bar is connected to the support block. The support block includes two support surfaces facing each other, an included angle is formed between the two support surfaces, one support surface is in contact with the fan support, and the other support surface is in contact with the main control board; and/or, the skin treatment apparatus further includes a cooling plate, and the cold compress component is thermally connected to the first thermal conductive section by the cooling plate; the third holder further includes a second mounting plate, one end of the second mounting plate is connected to the first connection support part, and the other end of the second mounting plate is connected to the second connection support part. The second mounting plate is defined with a mounting hole, the cooling plate is disposed in the mounting hole. The second mounting plate, the first connection support part, and the second connection support part enclose to form the third mounting cavity.

In some embodiments, the first connection support part includes: a support part side plate; a second support part side plate disposed on an outer side surface of the first support part side plate, a first receiving cavity being formed between the first support part side plate and the second support part side plate; a first connection component disposed in the first receiving cavity and configured to be connected with the thermal conductive structure and/or the main control board; and a first extension plate disposed on a surface of the second support part side plate far away from the light outlet, the first extension plate extending toward the side far away from the light outlet to dock with the second flow guiding part.

In some embodiments, a first mounting notch is defined between a first side edge of the first extension plate facing the ventilation part and the second support part side plate, and the ventilation part is disposed in the first mounting notch and in contact with the first side edge; and/or, a second mounting notch is defined in a second side edge of the first extension plate away from the second support part side plate, and at least part of the second diffuser plate extends into the second mounting notch and is in contact with the second side edge; and/or, a side of the first extension plate away from the ventilation part bends toward the light emitting side holder and is in contact with the third diffuser plate.

In some embodiments, a surface of the second support part side plate facing the light outlet and an outer side surface of the first support part side plate enclose to form a first connection component mounting cavity, and the first connection component includes: a second connection post, disposed on the first support part side plate and/or the second support part side plate and located in the first connection component mounting cavity, to connect the thermal conductive structure with the third holder by inserting a fastener into the second connection post and the thermal conductive structure; a third connection post, disposed on the first support part side plate and/or the second support part side plate and located in the first connection component mounting cavity, to connect the housing with the third holder by inserting a fastener into the third connection post and the housing, an extension direction of the second connection post and an extension direction of the third connection post forming an included angle; and/or, a first engagement protrusion part, disposed on the first support part side plate and/or the second support part side plate and located in the first connection component mounting cavity, to be engaged with the thermal conductive structure.

In some embodiments, the first connection component further includes: a first connecting block, disposed on the first support part side plate and the second support part side plate, and located in the first connection component mounting cavity. The second connection post is disposed on the first support part side plate and a surface of the first connection block away from the second support part side plate. The third connection post is disposed on the second support part side plate and a surface of the first connection block away from the first support part side plate.

In some embodiments, the second connection support part includes: a third support part side plate; a fourth support part side plate disposed on an outer side surface of the third support part side plate, a second receiving cavity being formed between the third support part side plate and the fourth support part side plate; a second connection component disposed in the second receiving cavity, configured to be connected with the thermal conductive structure and/or the main control board; a second extension plate disposed on a surface of the second support part side plate far away from the light outlet, the second extension plate extending toward the side far away from the light outlet to contact with the second flow guiding side plate and the third flow guiding side plate.

In some embodiments, a third mounting notch is defined between a first side edge of the second extension plate facing the fourth support part side plate and the fourth support part side plate, and the fourth support part side plate is disposed in the third mounting notch and in contact with the first side edge; and/or, a fourth mounting notch is defined in a second side edge of the second extension plate away from the fourth support part side plate, and at least part of the second flow guiding side plate and at least part of the third flow guiding side plate extend into the fourth mounting notch and are in contact with the second side edge.

In some embodiments, a surface of the fourth support part side plate facing the light outlet and an outer side surface of the third support part side plate enclose to form a second connection component mounting cavity, and the second connection component includes: a fourth connection post, disposed on the third support part side plate and/or the fourth support part side plate and located in the second connection component mounting cavity, to connect the thermal conductive structure with the third holder by inserting a fastener into the fourth connection post and the thermal conductive structure; a fifth connection post, disposed on the third support part side plate and/or the fourth support part side plate and located in the second connection component mounting cavity, to connect the housing with the third holder by inserting a fastener into the fifth connection post and the housing, an extension direction of the fourth connection post and an extension direction of the fifth connection post forming an included angle; and/or, a second engagement protrusion part, disposed on the third support part side plate and/or the fourth support part side plate and located in the second connection component mounting cavity, to be engaged with the thermal conductive structure.

In some embodiments, the second connection component further includes: a second connection block, disposed on the third support part side plate of the fourth support part side plate and located in the second connection component mounting cavity. The fourth connection post is disposed on the third support part side plate and a surface of the second connection block away from the fourth support part side plate. The fifth connection post is disposed on the fourth support part side plate and a surface of the second connection block away from the third support part side plate.

In some embodiments, a surface of the third support part side plate facing the cold compress component is provided with a first stop protrusion, the first stop protrusion is disposed close to the light outlet; and/or, a surface of the first support part side plate facing the cold compress component is provided with a second stop protrusion, the second stop protrusion is disposed close to the light outlet.

In some embodiments, the light emitting component includes a light emitting member and a filter. The skin treatment apparatus further includes a phototherapy lamp. The housing component further includes: a fourth holder, connected to the third holder and the second holder and located on a side of the third holder away from the thermal conductive structure, the fourth holder being defined with a fourth mounting cavity and a fifth mounting cavity, the phototherapy lamp being disposed in the fourth mounting cavity, and the fourth mounting cavity being located between the light outlet and the fifth mounting cavity; and a fifth holder, disposed in the fifth mounting cavity and located between the light emitting member and the cold compress component, the filter being disposed on the fifth holder.

In some embodiments, the first connection component further includes a sixth connection post disposed on a face of the first connection block facing the fourth holder, to allow a fastener to pass through the sixth connection post and the fourth holder; and/or, the second connection component further includes a seventh connection post disposed on a face of the second connection block facing the fourth holder, to allow a fastener pass through the seventh connection post and the fourth holder.

In some embodiments, the skin treatment apparatus further includes a Hall sensor. A side of fourth holder away from the third holder is provided with two third engagement parts facing each other. A limiting space is formed between the two third engagement parts, and at least part of the Hall sensor is located in the limiting space.

In some embodiments, the fourth holder includes: a third mounting plate; a baffle plate disposed on the third mounting plate; a first enclosure plate disposed on the third mounting plate and connected to the baffle plate, the first enclosure plate, a surface of the baffle plate facing the light outlet and at least a part of the third mounting plate enclosing to form the fourth mounting cavity; and a second enclosure plate disposed on the third mounting plate and connected to the baffle plate, the second enclosure plate, a surface of the baffle plate away from the light outlet and at least the other part of the third mounting plate enclosing to form the fifth mounting cavity.

In some embodiments, the first enclosure plate includes a first side plate section, a first connection plate section and a second side plate section connected successively. The first side plate section and the second side plate section face each other and are both connected to the baffle plate. A surface of the first connection plate facing the cold compress component is provided with a first engagement recessed part communicated with the fourth mounting cavity, and at least part of the phototherapy lamp extends into the first engagement recessed part and mates engaged with the first engagement recessed part. The two third engagement protrusion parts are disposed on a surface of the first connection plate away from the cold compress component.

In some embodiments, an outer side surface of the first side plate section is provided with a first support plate, which is configured to support the sixth connection post and is defined with a first passing hole for a fastener to pass through; and/or, an outer side surface of the second side plate section is provided with a second support plate, which is configured to support the seventh connection post and is defined with a second passing hole for a fastener to pass through.

In some embodiments, the third mounting plate located in the fourth mounting cavity is defined with a ventilation hole; and/or, each third engagement protrusion part extends toward the light outlet and then extends to a side edge of the first connection plate facing the light outlet.

In some embodiments, a connection of the third mounting plate, the first side plate section, and the first connection plate is defined with a first through hole for at least part of the phototherapy lamp to pass through; and/or, a connection of the third mounting plate, the second side plate section and the first connection plate is defined with a second through hole for at least part of the phototherapy lamp to pass through.

In some embodiments, the second enclosure plate includes a third side plate section, a second connection plate and a fourth side plate section connected successively. The third side plate section and the fourth side plate section face each other and are both connected to the baffle plate. A side edge of the first connection plate away from the light outlet is provided with a fourth engagement protrusion part that is engaged with the second holder.

In some embodiments, an outer side surface of the third side plate section is provided with a third support plate, which is configured to support the third holder and is provided with a second engagement recessed part that is engaged with the third holder; and/or, an outer side surface of the fourth side plate section is provided with a fourth support plate, which is configured to support the third holder and is provided with a third engagement recessed part that is engaged with the third holder.

In some embodiments, the heat dissipation component is located on one side of the light emitting component.

In some embodiments, the thermal conductive structure is a vapor chamber or a heat pipe. The heat dissipation sheet component and the light emitting component are located on two opposite sides of the thermal conductive structure.

In some embodiments, the thermal conductive structure further includes a third thermal conductive section. The third thermal conductive section is connected to an end of the second thermal conductive section away from the first thermal conductive section. The third thermal conductive section protrudes from the light emitting component in a direction opposite to the light output direction of the light emitting component. The heat dissipation sheet component is further disposed on the third thermal conductive section.

In some embodiments, the cold compress component includes a light transmitting member and a cooling plate. The light transmitting member is disposed on the housing component. The light transmitting member is located on a side of the light emitting component facing the light outlet and is disposed corresponding to the light outlet. The light transmitting member is configured to transmit the light generated by the light emitting component out of the light outlet. The cooling plate includes a cooling surface and a heat dissipation surface. The cooling surface is thermally connected to the light transmitting member, and the heat dissipation surface is thermally connected to the first thermal conductive section.

In some embodiments, a length direction the housing component and the light output direction of the light emitting component form an included angle. The included angle is greater than or equal to 6 degrees and less than or equal to 36 degrees.

According to the technical solution of the present disclosure, the skin treatment apparatus includes the housing component, the light emitting component, the cold compress component, and the heat dissipation component. The light generated from the light emitting component passes through the light outlet and then is irradiated to the skin to be treated. The cold compress component is disposed on the housing component and located at the light outlet for cooling the skin to be treated. The heat dissipation component includes the thermal conductive structure and the heat dissipation sheet component. The thermal conductive structure includes the first thermal conductive section and the second thermal conductive section connected to each other. The cold compress component is thermally connected to the first thermal conductive section. The light emitting component faces at least part of the second thermal conductive section. The second thermal conductive section extends along the light output direction of the light outlet. At least part of the heat dissipation sheet component is thermally connected to the second thermal conductive section. In such a way, the heat generated by the cold compress component is conducted to the second thermal conductive section through the first thermal conductive section, and then is dissipated through the heat dissipation sheet component thermally connected to the second thermal conductive section. In the present disclosure, since the second thermal conductive section thermally connected to the heat dissipation sheet component is disposed corresponding to the light emitting component, the heat dissipation sheet component is disposed close to the cold compress component, the thermal conductive path is shortened. In other words, the heat dissipation sheet component and the light emitting component are stacked in the thickness direction of the housing component. Compared with the related art in which the cold compress component, the light emitting component and the heat dissipation sheet component are arranged along a straight line, the skin treatment apparatus of the present disclosure shortens the overall length of the thermal conductive structure and accordingly shortens the thermal conductive path, which allows the heat dissipation sheet component to be closer to the light emitting component, thereby improving the heat dissipation efficiency. Therefore, the problem in related art that the length of the thermal conductive component of the skin treatment apparatus is relatively long and thereby affecting the heat dissipation efficiency of the heat dissipation sheet component is solved.

BRIEF DESCRIPTION OF DRAWINGS

The drawings forming a part of the present disclosure are intended to provide further understanding of the present disclosure. The embodiments of the present disclosure and the corresponding descriptions are used to interpret the present disclosure and do not constitute undue limitation of the present disclosure.

REFERENCE NUMERALS

Figure 1:
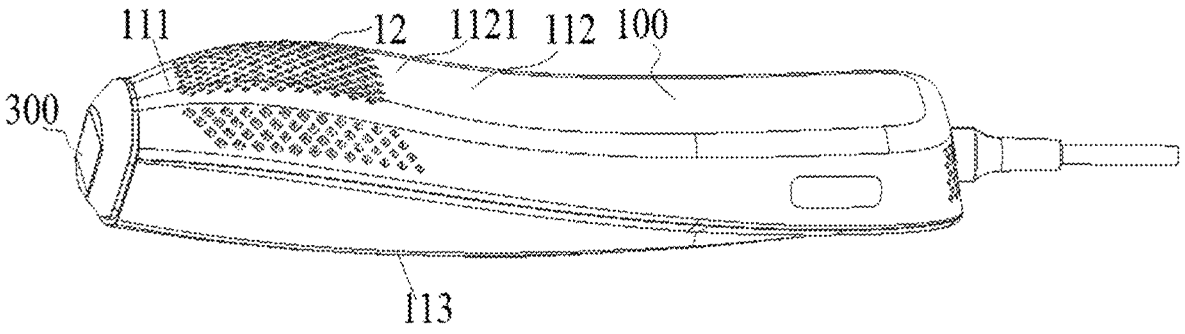
FIG. 1 is a perspective view of a skin treatment apparatus according to an embodiment of the present disclosure.

100, housing component; 10, first housing; 102, limiting protrusion part; 1021, main rib; 1022, lateral rib; 1023, notch; 103, mounting cavity; 104, positioning rib; 105, heat dissipation cavity; 11, light outlet; 12, air vent part; 1201, housing air outlet part; 1202, air inlet part; 1203, air vent; **1203*a*, outer air vent section; 1203*b*, inner air vent section; 1211, first air outlet part; 1212, second air outlet part; 1213, first air outlet; 1214, second air outlet; 1215, designated air outlet part; 1216, designated air outlet; 1221, air inlet; 13, bulge part; 1301, third wall section; 1302, fourth wall section; 14, back plate; 1401, first back plate section; 1402, second back plate section; 15, first side plate; 1501, first side plate section; 1502, second side plate section; 131, pressure groove; 16, grip area; 17, ventilation area; 18, insertion groove; 1801, latching hole; 191, first straight line; 192, second straight line; 110, housing; 111, necking section; 112, first side plate; 1121, first extension section; 113, second side plate; 114, button; 115, concave part; 116, first wall section; 117, second wall section; 120, holder component; 121, first mounting cavity; 122, second mounting cavity; 123, first ventilation surface; 1231, first air vent; 124, heat dissipation sheet holder; 1241, mounting port; 1242, second air vent; 1243, second outer support part; 1243*a*, first flow duct plate; 1243*b*, second flow duct plate; 1243*c*, light-blocking flow guiding part; 125, light emitting side holder; 1251, third mounting cavity; 1252, second holder; 1252*a*, holder light outlet; 1252*b*, heat dissipation support plate; 1252*c*, weight reduction hole; 1253, third holder; 1253*a*, second mounting plate; 1253*b*, mounting hole; 131, first support part; 1311, first support plate; 1312, auxiliary support plate; 1313, drainage plate; 132, first side support part; 1321, third support plate; 133, second support part; 1331, second support plate; 134, second side support part; 1341, fourth support plate; 135, third air vent; 136, first air blocking protrusion part; 137, second air blocking protrusion part; 138, third air blocking protrusion part; 141, first outer support part; 1411, first air duct plate; 1412, second air duct plate; 142, first engagement part; 143, second engagement part; 151, first ventilation flow channel; 152, second ventilation flow channel; 1521, ventilation through port; 1522, diffuser auxiliary cavity; 161, first mounting plate; 162, first side part; 163, second side part; 171, first connection support part; 1711, first support part side plate; 1712, second support part side plate; 1713, first connection component; 1713*a*, second connection post; 1713*b*, third connection post; 1713*c*, first engagement protrusion part; 1713*d*, first connection block; 1713*e*, second connection block; 1713*f*, sixth connection post; 1713*g*, seventh connection post; 1714, first extension plate; 172, second connection support part; 1721, third support part side plate; 1721*a*, first stop protrusion; 1722, fourth support part side plate; 1723, second connection component; 1723*a*, fourth connection post; 1723*b*, fifth connection post; 1723*c*, second engagement protrusion part; 1724, second extension plate; 181, first flow guiding part; 1811, first flow guiding side plate; 1812, second flow guiding side plate; 1813, third flow guiding side plate; 1814, fourth flow guiding side plate; 1815, third engagement part; 1816, fourth engagement part; 182, second flow guiding part; 1821, diffuser cavity; 1822, diffuser hole; 1823, first diffuser plate; 1824, second diffuser plate; 1825, third diffuser plate; 1826, ventilation part; 1826*a*, first ventilation plate; 1826*b*, second ventilation plate; 1826*c*, third ventilation plate; 1826*d*, fourth ventilation plate; 1827, first support section; 1828, second support section; 1828*a*, support bar; 1828*b*, support block; 1829*a*, fifth engagement part; 1829*b*, sixth engagement part; 191, fourth holder; 1911, fourth mounting cavity; 1912, fifth mounting cavity; 193, third engagement protrusion part; 194, third mounting plate; 1941, ventilation hole; 195, baffle plate; 196, first enclosure plate; 1961, first side plate section; 1962, first connection plate; 1963, second side plate section; 1964, first support plate; 1965, second support plate; 197, second enclosure plate; 1971, third side plate section; 1972, second connection plate; 1973, fourth side plate section; 1974, third support plate; 1975, fourth support plate; 1981, first through hole; 1982, second through hole; 20, second housing; 21, face plate; 210, face plate part; 211, first face plate section; 212, second face plate section; 22, second side plate; 221, third side plate section; 222, fourth side plate section; 23, insertion part; 231, latching platform; 30, first housing section; 31, first housing part; 32, second housing part; 40, second housing section; 41, third housing part; 42, fourth housing part; 51, first area; 52**, second area;

200, light emitting component; 201, light emitting port; 210, light emitting member; 220, filter; 230, reflector; 231, insertion pin; 240, sealing structure; 241, insertion slot; 242, sealing rib; 243, limiting groove; 244, latching protrusion part; 245, latching notch; 246, first sealing structure; 2461, mating rib; 247, second sealing structure; 2471, semi-annular protrusion;

300, cold compress component; 301, air intake port; 302, air exhaust port; 310, light transmitting member; 311, positioning slot; 312, light outgoing surface; 313, light incoming surface; 3131, bump; 314, side surface part; 3141, first side surface; 3142, second side surface; 330, spacing space;

400, heat dissipation component; 401, insertion slot; 4011, first insertion port; 4031, second insertion port; 4032, main strip-shaped groove; 4033, side strip-shaped groove; 402, sealing rib; 403, limiting groove; 410, thermal conductive structure; 411, first thermal conductive section; 412, second thermal conductive section; 420, heat dissipation sheet component; 421, first side surface; 422, second side surface; 423, missing corner; 424, transition surface; 4241, first sub-transition surface; 4242, second sub-transition surface; 425, heat dissipation sheet; 4251, heat dissipation sheet body; 4252, flange; 4253, ventilation channel; 427, air outlet; 4271, first sub-air outlet; 4272, second sub-air outlet;

- 500, fan; 600, main control board;
- 700, fan support; 710, support base; 711, hollow cavity; 712, first base; 7121, first base plate; 7122, avoidance notch; 7123, first limiting flange; 7124, second limiting flange; 7125, third limiting step; 713, second base; 7131, second base plate; 7132, support bar; 714, first side base; 7141, first side body; 7142, first limiting step; 7143, first snap-fit element; 7144, notch; 7145, thickness reduction groove; 715, second side base; 7151, second side body; 7151*a*, inclined body; 7151*b*, protrusion body; 7152, second limiting step; 7153, second snap-fit element; 716, protection part; 7161, protection groove; 7162, protection bottom wall; 7163, protection peripheral wall; 7164, positioning post; 7171, first holder connection post; 7172, second holder connection post; 7173, third holder connection post; 7174, fourth holder connection post; 7175, limiting ring; 7181, fifth holder connection post; 7182, sixth holder connection post; 721, first connection seat; 722, second connection seat; 723, fourth limiting step; 731, extension plate; 732, limiting bar; 733, hollow hole; 734, extension arm; 735, third snap-fit element;
- 800, cooling plate;
- 900, phototherapy lamp;
- 910, Hall sensor;
- 920, element;
- 930, control board;
- 940, partition part;
- 950, drainage part; 951, drainage surface; 952, air intake space.

DESCRIPTION OF EMBODIMENTS

It should be noted that the embodiments in the present disclosure and the features in the embodiments may be combined with each other in case of no conflict, the present disclosure is described in detail below with reference to the attached drawings and in conjunction with embodiments.

It should be noted that, unless otherwise indicated, all technical and scientific terms used herein have the same meaning as would normally be understood by those skilled in the art.

In the present disclosure, where the contrary is not stated, the terms "up" and "down" are used in the directions shown in the attached drawings, or in the longitudinal, vertical, or gravitational directions. Similarly, for ease of understanding and description, the terms "left" and "right" usually refers to the left and right shown in the attached drawings; the terms "inner" and "outer" means inside and outside relative to the outline of each part itself. These terms are not intended to limit the present disclosure.

To solve the problem in related art that the length of the thermal conductive component of the skin treatment apparatus is relatively long and thereby affecting the heat dissipation efficiency of the heat dissipation sheet component, the present disclosure provides a skin treatment apparatus.

Figure 59:
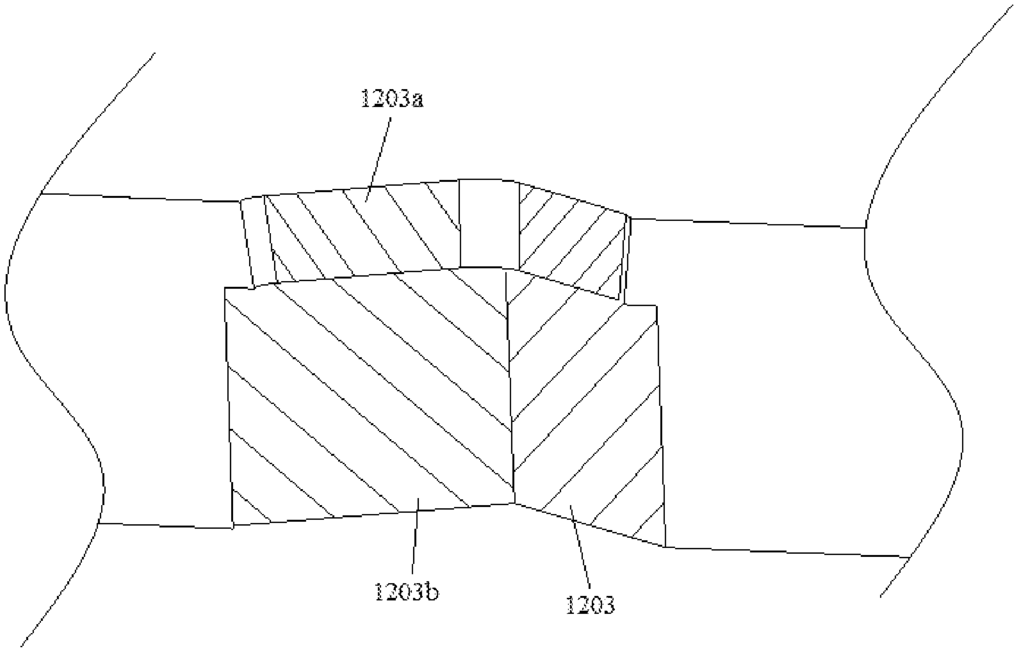
FIG. 59 is a longitudinal sectional diagram of an air vent of the skin treatment according to the present disclosure.

As shown in FIG. 1 to FIG. 59, the skin treatment apparatus includes a housing component 100, a light emitting component 200, a cold compress component 300, and a heat dissipation component 400. The housing component 100 is defined with an accommodation cavity and a light outlet 11 communicating with each other. The light emitting component 200 is disposed in the accommodation cavity to generate light, which passes through the light outlet 11 and then is irradiated to a skin to be treated. The cold compress component 300 is disposed on the housing component 100 and located at the light outlet 11 for cooling the skin to be treated or a skin in the vicinity of the skin to be treated. The heat dissipation component 400 includes a thermal conductive structure 410 and a heat dissipation sheet component 420. The thermal conductive structure 410 includes a first thermal conductive section 411 and a second thermal conductive section 412 connected to each other. The cold compress component 300 is thermally connected to the first thermal conductive section 411. The light emitting component 200 faces at least part of the second thermal conductive section 412. At least part of the heat dissipation sheet component 420 is thermally connected to the second thermal conductive section 412.

The light emitting component 200 is configured to generate and emit the light to the light outlet 11.

According to the technical solution provided in the embodiments, the heat generated by the cold compress component 300 is conducted through the first thermal conductive section 411 to the second thermal conductive section 412, and then is dissipated through the heat dissipation sheet component 420 thermally connected to the second thermal conductive section 412. In the present disclosure, the second thermal conductive section 412 thermally connected to the heat dissipation sheet component 420 is disposed corresponding to the light emitting component 200, so that the heat dissipation sheet component 420 is closer to the cold compress component 300, thereby shortening the thermal conductive path.

In other words, the heat dissipation sheet component 420 and the light emitting component 200 are stacked in the thickness direction of the housing component 100. Compared with the related art in which the cold compress component, the light emitting component and the heat dissipation sheet component are arranged along a straight line, the skin treatment apparatus provided in the embodiments shortens the overall length of the thermal conductive structure 410 and accordingly shortens the thermal conductive path, which allows the heat dissipation sheet component 420 to be closer to the light emitting component 200, thereby improving the heat dissipation efficiency. Therefore, the problem in related art that the length of the thermal conductive component of the skin treatment apparatus is relatively long and thereby affecting the heat dissipation efficiency of the heat dissipation sheet component is solved.

Further, the thermal conductive structure 410 extends along a light output direction of the light emitting component 200.

Further, the thermal conductive structure 410 includes a capillary flow channel and a thermal conductive medium disposed in the capillary flow channel. The first thermal conductive section 411 is an evaporation section, and the second thermal conductive section 412 is a condensation section.

In the embodiments, the skin treatment apparatus may be used as a hair removal instrument and/or a skin rejuvenation instrument, based on the wavelength of the light generated by the light emitting component 200.

In an embodiment, the light emitting component 200 may be an intense pulsed light (IPL) light-emitting light source component to generate intense pulsed light, also known as pulsed intense light. The IPL is a type of broad-spectrum light generated after a high-intensity light source has been focused and filtered. The wavelength of the IPL is mostly 400 nanometer (nm) to 200 nm, and the IPL with different wavelengths has different functions. For example, the IPL with a wavelength of 690 nm to 1200 nm uses the principle of photo pyrolysis of the IPL and accordingly has the hair removal effect. Since the melanocytes in the hair follicles can selectively absorb light in a specific wavelength band, and the IPL can penetrate the epidermis and directly reach the hair follicles, light energy in the dermis is absorbed by the melanocytes in the hair follicles and then converted into heat energy to increase the temperature of the hair follicles. When the temperature of the hair follicles is high enough, the structure of the hair follicles will be irreversibly damaged, and the damaged hair follicles will naturally fall off after a period of time. As a result, the hair growth will be delayed or even inhibited in a short period of time. For another example, the IPL with a wavelength of 560 nanometer (nm) to 640 nm mainly has a skin rejuvenation effect. Alternatively, the second sub-light emitting component is a laser light emitting component to generate laser light, so as to achieve hair removal by laser.

In some embodiments, the heat dissipation component 400 is located on a side of the light emitting component 200. In this way, the entire heat dissipation component 400 is located on one side of the light emitting component 200, so that the heat dissipation component 400 and the light emitting component 200 are stacked in the thickness direction of the housing component 100, which simplifies the structure.

As shown in FIG. 1, the housing component 100 is provided with a housing air outlet part 1201. At least part of the heat dissipation component 400 is located between the housing air outlet part 1201 and the light emitting component 200, so that at least part of the heat dissipation component 400 is disposed corresponding to the housing air outlet part 1201. In this way, the heat dissipation component 400 is located above the light emitting component 200, which ensures that an airflow after heat exchange is smoothly discharged from the housing air outlet part 1201, thereby preventing the accumulation of hot air from resulting in overall heating of the skin treatment apparatus. Also, the above arrangement makes the layout of the heat dissipation component 400 in the skin treatment apparatus more reasonable and compact.

As shown in FIG. 1, the housing component 100 includes a housing 110. The light outlet 11 is located at a first end of the housing 110. The first end of the housing 110 is provided with a necking section 111. As such, the front end of the skin treatment apparatus is in a necking shape, which reduces the shielding of the front end of the housing component 100 to the skin where the skin treatment apparatus performs the treatment. Therefore, it is convenient for a user to observe, and the user may change the mode or the treatment region according to needs.

In some embodiments, the height of at least part of the heat dissipation sheet component 420 gradually decreases in the light output direction of the light emitting component 200, to fit the necking section 111. This arrangement allows the heat dissipation sheet component 420 to better fit the necking section 111, and also prevents an occurrence of interference between the two in the disassembly process which may affect normal disassembly of the skin treatment apparatus.

Figure 7:
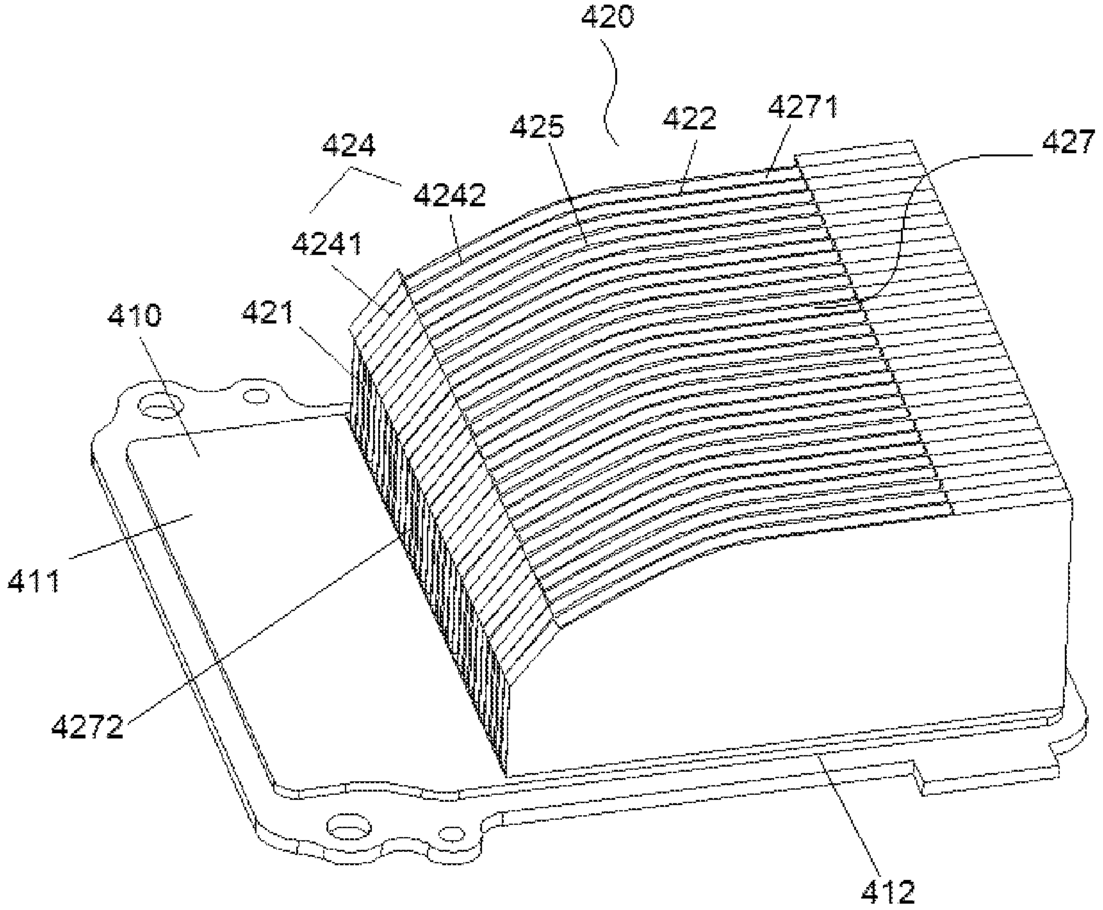
FIG. 7 is a structural schematic diagram of the heat dissipation component in FIG. 6.
Figure 8:
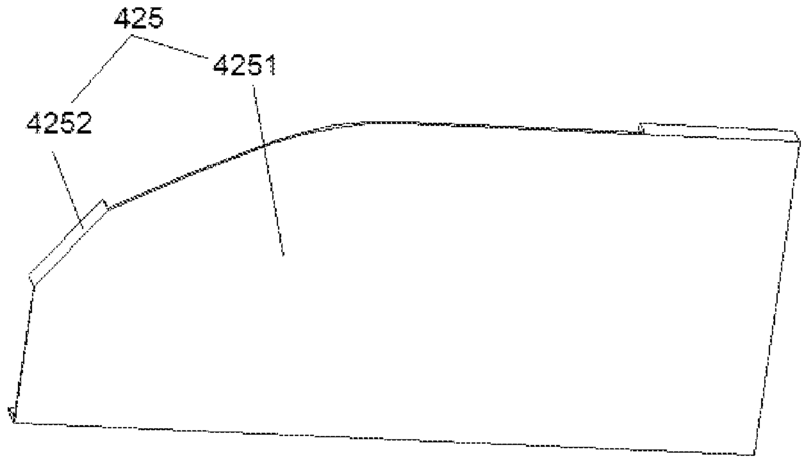
FIG. 8 is a structural schematic diagram of a heat dissipation sheet in FIG. 7.

As shown in FIG. 7, the heat dissipation sheet component 420 includes a first side surface 421 and a second side surface 422. The first side surface 421 faces the first end of the housing 110, and the second side surface 422 faces away from the light emitting component 200. A joint of the first side surface 421 and the second side surface 422 is defined with a missing corner 423. The missing corner 423 is disposed corresponding to the necked section 111. The missing corner 423 is disposed in such a way that it is possible to form the front end of the housing component 100 corresponding to the missing corner 423 into the necking shape. During the use of the skin treatment apparatus, the above arrangement helps to reduce the shielding of the front end of the housing component 100 to the skin where the skin treatment apparatus performs the treatment, which is convenient for the user to observe.

As shown in FIG. 7, the heat dissipation sheet component 420 further includes a transition surface 424. The first side surface 421 is connected to the second side surface 422 through the transition surface 424. The transition surface 424 and the first side surface 421 form an included angle, and the transition surface 424 and the second side surface 422 form an included angle. The missing corner 423 is formed between the transition surface 424 and the housing 110. The above arrangement in which the transition surface 424 is disposed at an included angle with the first side surface 421 and at an included angle with the second side surface 422, and the transition surface 424 is located at the joint of the first side surface 421 and the second side surface 422 makes it easier and simpler to process the missing corner 423, thereby reducing the overall processing cost and difficulty of the heat dissipation sheet component 420.

Optionally, the transition surface 424 is an inclined surface or a curved surface; or, the transition surface 424 includes a first sub-transition surface 4241 and a second sub-transition surface 4242 forming an included angle with first sub-transition surface 4241. The first sub-transition surface 4241 is connected to the first side surface 421, and the second sub-transition surface 4242 is connected to the second side surface 422. The first sub-transition surface 4241 is a first flat surface or a first curved surface. The second sub-transition surface 4242 is a second flat surface or a second curved surface. The above arrangement allows for more versatility in the selection of the shape of the transition surface 424, so as to meet different use requirements and working conditions, and also improve the processing flexibility.

In some embodiments, the transition surface 424 includes the first sub-transition surface 4241 and the second sub-transition surface 4242 forming the included angle with the first sub-transition surface 4241. The first sub-transition surface 4241 is connected to the first side surface 421, and the second sub-transition surface 4242 is connected to the second side surface 422. The first sub-transition surface 4241 is a first curved surface, and the second sub-transition surface 4242 is a second curved surface. Compared with a chamfer, the above arrangement allows the heat dissipation sheet component 420 to have a larger heat dissipation area, thereby improving the heat dissipation capability of the heat dissipation sheet component 420.

In some embodiments, the heat dissipation sheet component 420 includes a plurality of heat dissipation sheet 425 spaced apart along a first direction D1. A first side edge of each heat dissipation sheet 425 forms the first side surface 421, and a second side edge of each heat dissipation sheet 425 form the second side surface 422. Each heat dissipation sheet 425 extends along a second direction D2. The first direction D1 and the second direction D2 form an included angle, and the second direction D2 is the same as the light output direction of the light emitting component 200. Optionally, the second direction D2 is the same as a front-rear direction of the housing component 100, and the first direction D1 is perpendicular to the second direction D2. In this way, the arrangement of the plurality of heat dissipation sheets 425 in the housing component 100 is made more reasonable and compact, and also the heat dissipation area of the heat dissipation sheet component 420 is increased, thereby improving the heat dissipation efficiency of the heat dissipation sheet component 420.

In the embodiments, the transition surface 424 includes the first sub-transition surface 4241 and the second sub-transition surface 4242 forming the included angle with the first sub-transition surface 4241. The first sub-transition surface 4241 is connected to the first side surface 421, and the second sub-transition surface 4242 is connected to the second side surface 422. Each heat dissipation sheet 425 includes a heat dissipation sheet body 4251 and a flange 4252. The heat dissipation sheet body 4251 includes the first side surface 421, the second side surface 422, and the second sub-transition surface 4242. The flange 4252 is disposed on the heat dissipation sheet body 4251, and forms an included angle with the heat dissipation sheet body 4251. The surface of the flange 4252 away from the heat dissipation sheet body 4251 forms the first sub-transition surface 4241. A ventilation channel 4253 is formed between the heat dissipation sheet bodies 4251 of two adjacent heat dissipation sheets 425, and the flange 4252 of each heat dissipation sheet 425 is in contact with its adjacent heat dissipation sheet 425 and configured to block at least part of the ventilation channel 4253, so as to form an air outlet 427 on two sides of the flange 4252. Illustratively, the flange 4252 acts as a blocking part. The first sub-transition surface 4241 and the second sub-transition surface 4242 are disposed in such a way that a first missing part and a second missing part are correspondingly formed, to avoid directly forming a blocking part on the missing corner 423. In this way, the blocking part allows the air entering the ventilation channel 4253 to flow in a preset speed. Also, it is ensured that the blocking part does not take up a large amount of space and therefore does not affect the setting of the air outlet 427.

Illustratively, the flange 4252 is formed on the heat dissipation sheet 425 for forming the ventilation channel 4253. In manufacturing, a margin may be left at a first missing corner of the heat dissipation sheet 425, and then the margin is bent to one side to form the flange 4252. That is, the first missing part and the second missing part facilitates the formation of the flange 4252 at the first missing part. The flange 4252 is further configured to abut against the adjacent heat dissipation sheet 425 when subjected to an external force, so as to prevent the thin heat dissipation sheet 425 from being easily deformed and affecting the spacing between the heat dissipation sheets 425. In addition, the flange 4252 can increase the contact area between the heat dissipation sheet 425 and the air, further improving the heat dissipation effect of the heat dissipation sheet 425.

It should be noted that the structure of the heat dissipation sheet component 420 is not limited thereto, and may be adjusted according to working conditions and use requirements.

In other embodiments not shown in the figures, the ventilation channel is formed between two adjacent heat dissipation sheets, and the heat dissipation sheet component further includes a blocking part. The blocking part is disposed on a part of a third side edge of at least one heat dissipation sheet, and is configured to block at least part of the ventilation channel. The surface of the blocking part away from the light emitting component forms the first sub-transition surface so as to form the air outlet at two sides of the blocking part. The other part of the third side edge of at least one heat dissipation sheet forms the second sub-transition surface. The first sub-transition surface and the second sub-transition surface are disposed in such a way that a first missing part and a second missing part are correspondingly formed, to avoid directly forming the blocking part on the missing corner. In this way, the blocking part allows the air entering the ventilation channel 4253 to flow in a preset speed. Also, it is ensured that the blocking part does not take up a large amount of space and therefore does not affect the setting of the air outlet 427.

In the embodiments, the ventilation channel 4253 is formed between two adjacent heat dissipation sheets 425, the heat dissipation sheet component 420 is provided with the air inlet and the air outlet 427. The air inlet is communicated with the air outlet 427 through the ventilation channel 4253. The air inlet is located on the side of the heat dissipation sheet component 420 away from the first side surface 421, and the air outlet 427 is located on at least one of the first side surface 421, the second side surface 422 and the missing corner 423. In this way, the airflow blown out from an air outlet of a fan enters the heat dissipation sheet component 420 through the air inlet and flows along the ventilation channel 4253 to take away heat on the surfaces of the heat dissipation sheets 425, and finally is discharged through the air outlet 427, which allows the airflow to flow smoothly in the heat dissipation sheet component 420 and thereby avoiding the heat accumulation. In addition, the air inlet of the heat dissipation sheet component 420 is staggered with the air outlet of the heat dissipation sheet component 420, thereby preventing the turbulence of hot air in the heat dissipation sheet component 420 which may affect the normal flow of air.

Optionally, the air outlet 427 includes a first sub-air outlet 4271 and a second sub-air outlet 4272. The first sub-air outlet 4271 is located at the first side surface 421, and the second sub-air outlet 4272 is located at the second side surface 422 and/or the missing corner 423.

Optionally, a ratio of a length of the missing corner 423 to a length of the heat dissipation sheet 425 is greater than or equal to 0.32 and less than or equal to 0.55. It can be understood that a greater value of the ratio allows for a greater length of the missing corner 423, which is advantageous to dispose a longer necking section.

Optionally, a ratio of a width of the missing corner 423 to a width of the heat dissipation sheet 425 is greater than or equal to 0.36 and less than or equal to 0.6. It can be understood that a greater value of the ratio allows for a greater length of the missing corner 423, which is advantageous to dispose a longer necking section.

It can be understood that the above arrangement allows the missing corner 423 to have a sufficient avoidance margin to avoid the necking section and also ensures the heat dissipation of the heat dissipation sheet component.

Optionally, the heat dissipation sheet component 420 is located on one side of the thermal conductive structure 410, and the light emitting component 200 is located at the other side of the thermal conductive structure 410. This reduces the difficulty of installation and design. It can be understood that, in other embodiments, according to heat dissipation requirements, the end of the heat dissipation sheet component 420 away from the light outlet may bend and extend to the side where the light emitting component 200 is located, to increase the heat dissipation area of the heat dissipation sheet component.

The above arrangement allows for more flexible selection in the length and the width of the missing corner 423, to meet different use requirements and working conditions, and improve the processing flexibility. In addition, the above arrangement ensures that the hot air generated during the heat dissipation of the heat dissipation sheet 425 is discharged through the first sub-air outlet 4271 and the second sub-air outlet 4272, which prevents heat from accumulating in the heat dissipation sheet component 420, thereby improving the heat dissipation efficiency of the heat dissipation sheet component 420.

In the embodiments, the ratio of the length of the missing corner 423 to the length of the heat dissipation sheet 425 is 0.4, and the ratio of the width of the missing corner 423 to the width of the heat dissipation sheet 425 is 0.5. This allows for more reasonable selection in the size of the missing corner 423 and reduces the processing cost and difficulty of the missing corner 423.

It should be noted that the ratio of the length of the missing corner 423 to the length of the heat dissipation sheet 425 is not limited thereto, and may be adjusted according to working conditions and use requirements. Optionally, the ratio of the length of the missing corner 423 to the length of the heat dissipation sheet 425 is 0.35, 0.42, 0.45, 0.50, or 0.52.

It should be noted that the ratio of the width of the missing corner 423 to the width of the heat dissipation sheet 425 is not limited thereto, and may be adjusted according to working conditions and use requirements. Optionally, the ratio of the width of the missing corner 423 to the width of the heat dissipation sheet 425 is 0.38, 0.40, 0.42, 0.45, 0.52, 0.55, or 0.58.

Optionally, the light emitting component 200 includes a light emitting member 210 and a filter 220. In the light output direction of the light emitting component 200, a distance between the first side surface 421 and the filter 220 is less than or equal to 9 mm. In this way, the light emitted by the light emitting component 200 is filtered by the filter 220 and then irradiated to the light transmitting member 310. The above arrangement makes the first side surface 421 closer to the filter 220, such that a distance between the first side surface and the light outlet 11 is longer, and the necking section 111 is allowed to have a large degree of inclination.

Moreover, since the light emitting temperature of the light emitting member 210 is relatively high in the area behind the filter 220, the above arrangement is advantageous for the heat dissipation of the heat dissipation sheet component 420.

It should be noted that, the first side surface 421 may be located at the front end or the rear end of the filter 220 in the light output direction of the light emitting component 200.

Figure 2:
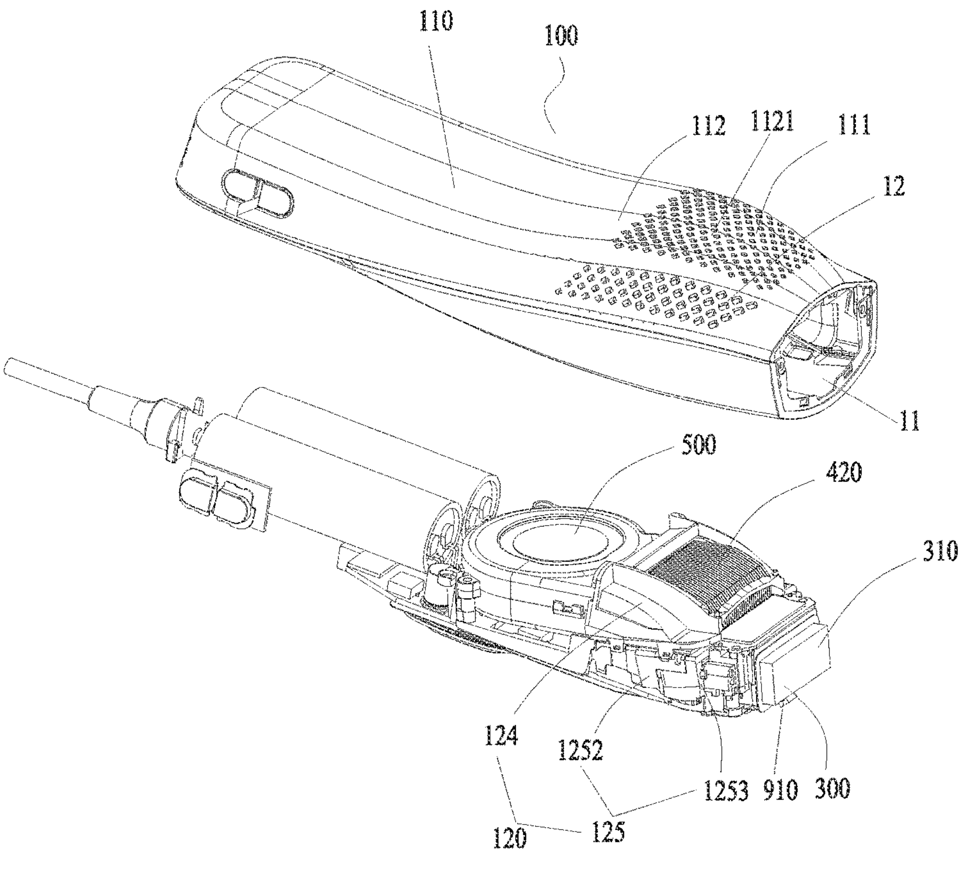
FIG. 2 is a disassembly diagram of a housing, a light emitting component, a fan, a cold compress component, and a heat dissipation component of the skin treatment apparatus in FIG. 1.
Figure 3:
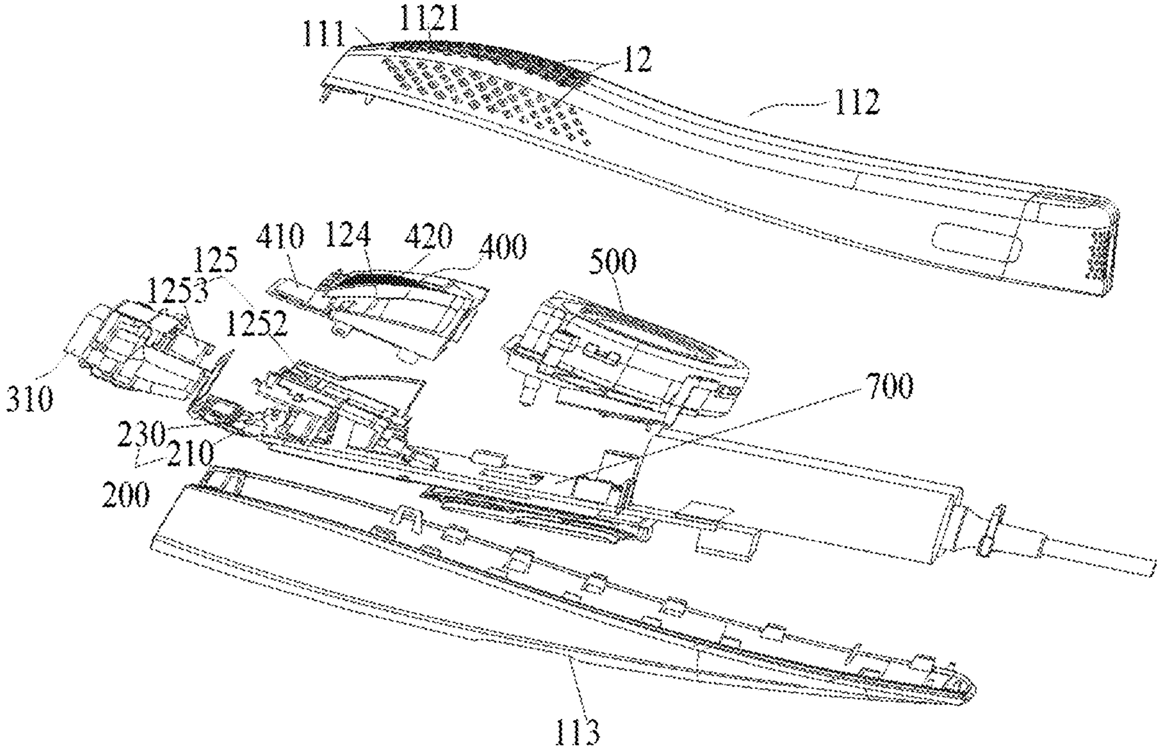
FIG. 3 is an exploded diagram of the skin treatment apparatus in FIG. 1.

As shown in FIG. 1 to FIG. 3, the housing 110 includes a first side plate 112 and a second side plate 113. The second side plate 113 faces the first side plate 112. The first side plate 112 is located on the side of the heat dissipation sheet component 420 away from the light emitting component 200. The surface of the first side plate 112 facing the second side surface 422 of the heat dissipation sheet component 420 defines a first extension section 1121. In the light output direction of the light emitting component 200, at least part of the first extension section 1121 is gradually bent toward the second side plate 113 to form at least part of the necking section 111. In this way, the first extension section 1121 is gradually close to the second side plate 113 from the rear to the front, to form the front end of the housing component 100 into the necking shape, which prevents the front end from blocking the user's view during use.

Figure 4:
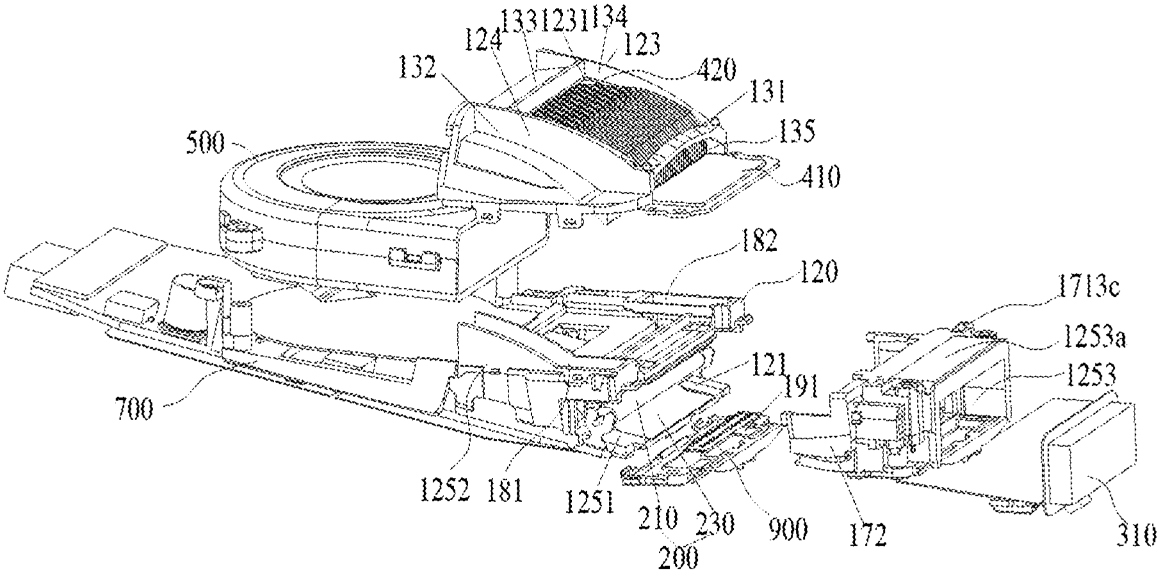
FIG. 4 is a disassembly diagram of a heat dissipation component, a holder component, a cold compress component, and a fan of the skin treatment apparatus in FIG. 3.
Figure 5:
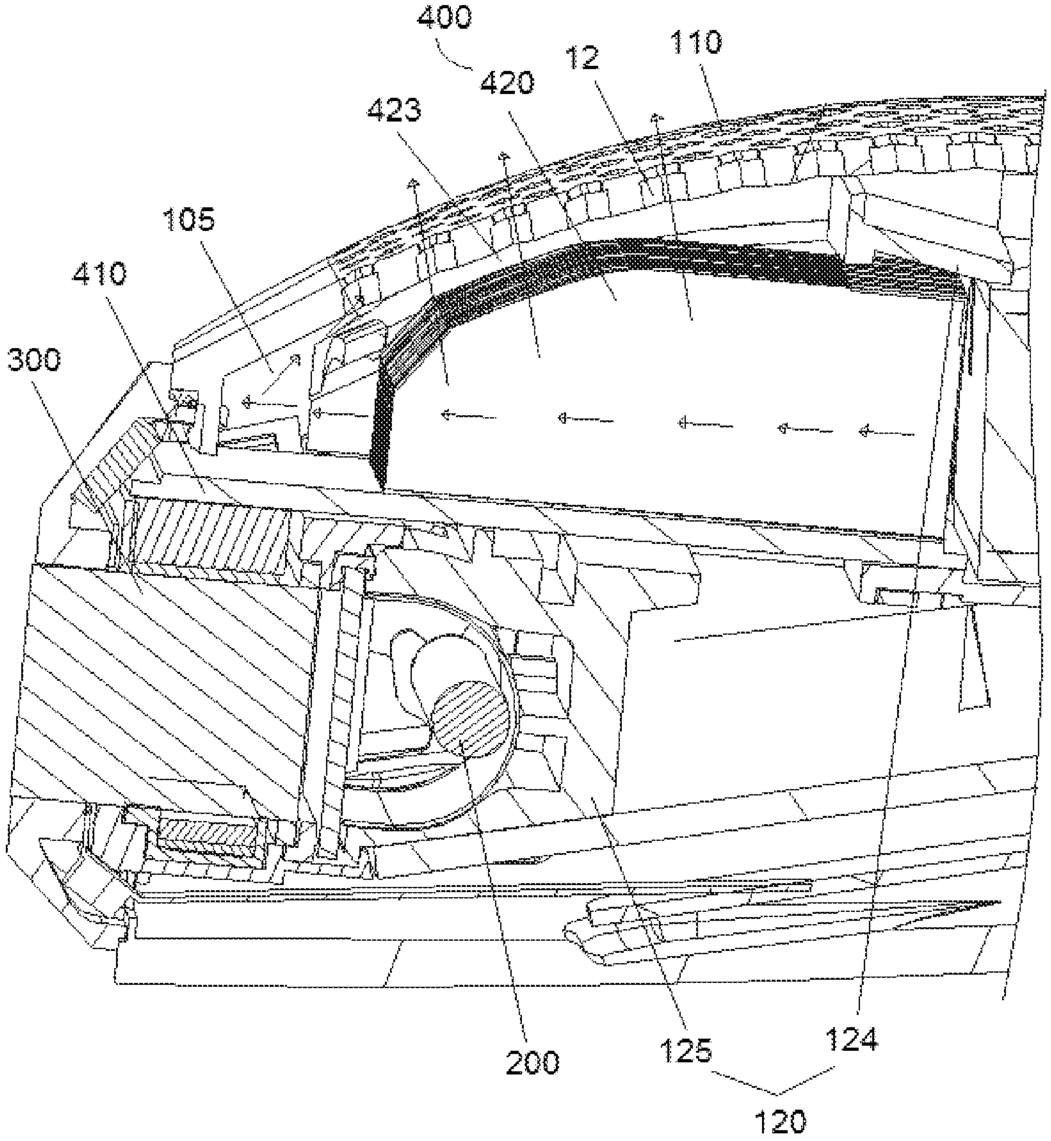
FIG. 5 is a sectional diagram of a skin treatment apparatus according to a first embodiment of the present disclosure.
Figure 32:
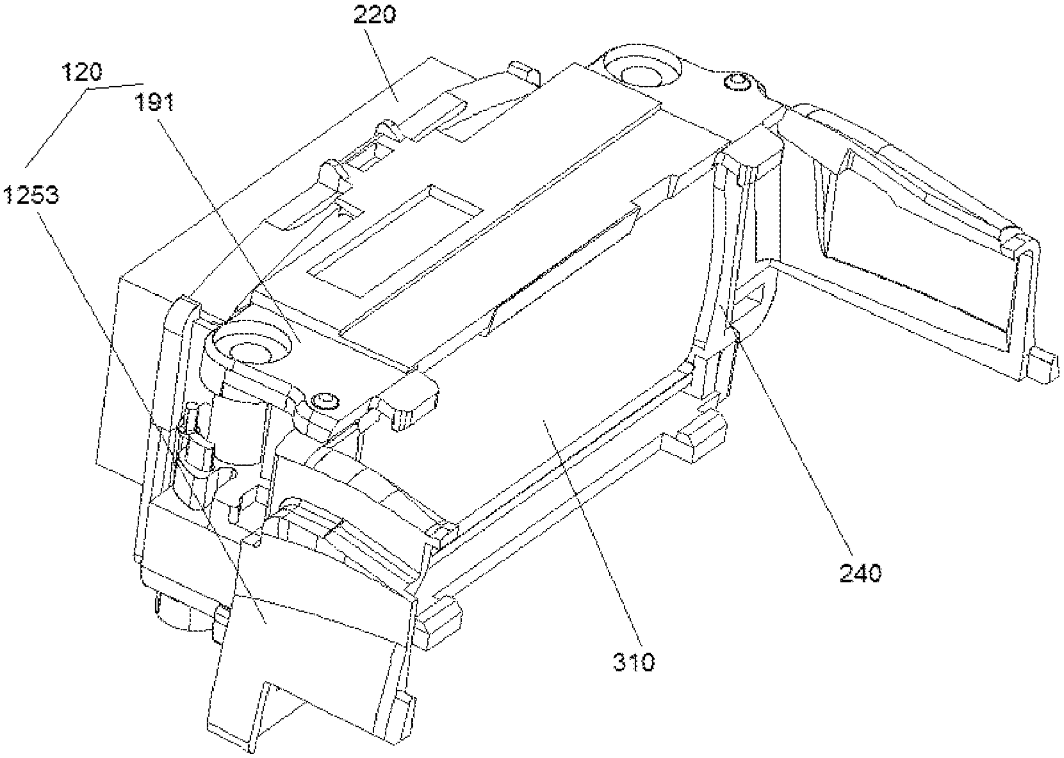
FIG. 32 is a perspective view of a light transmitting member, a third holder, and a fourth holder of the skin treatment apparatus in FIG. 4 in assembly.

As shown in FIG. 4 and FIG. 32, the housing component 100 further includes a holder component 120. The holder component 120 is disposed in the accommodation cavity. The holder component 120 is defined with a first mounting cavity 121 and a second mounting cavity 122. The light emitting component 200 is disposed in the first mounting cavity 121, and the heat dissipation sheet component 420 is disposed in the second mounting cavity 122. In the length direction of the housing 110, a projection of at least part of the second mounting cavity 122 on the first mounting cavity 121 is within the first mounting cavity 121. The above arrangement further ensures that the heat dissipation sheet component 420 is staggered with respect to the light emitting component 200 in the length direction of the housing 110, which shortens the overall length of the thermal conductive structure 410 and thereby shortening the thermal conductive path. Also, the above arrangement makes the layout of the light emitting component 200 and the heat dissipation sheet component 420 in the housing 110 more reasonable and compact, improving the utilization rate of the internal space.

Figure 9:
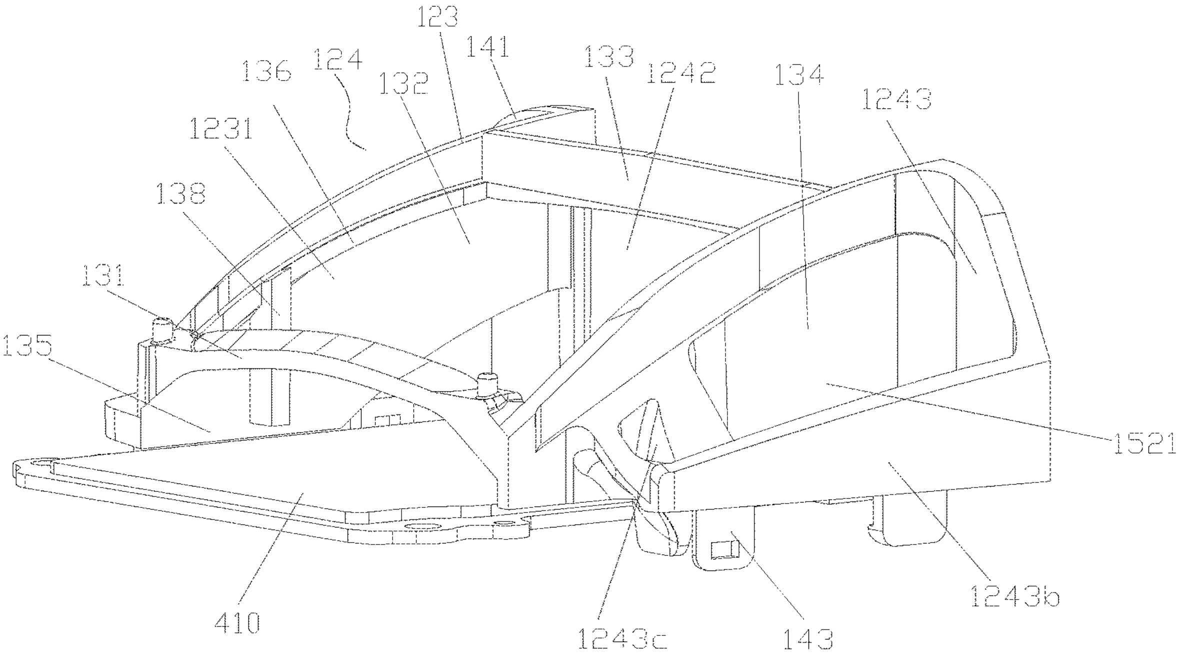
FIG. 9 is a structural schematic diagram of a heat dissipation sheet holder in FIG. 5.

As shown in FIG. 9, the holder component 120 includes a first ventilation surface 123 facing the first extension section 1121. In the light output direction of the light emitting component 200, at least part of the first ventilation surface 123 extends toward the second side plate 113 so as to fit the first extension section 1121. The first ventilation surface 123 is defined with a first air vent 1231 communicated with the second mounting cavity 122. In this way, the airflow after completing heat exchange with the heat dissipation sheet component 420 is blown out through the first ventilation surface 123. Also, the first ventilation surface 123 fits the necking section 111, which prevents structural interference between the holder component 120 and the necking section 111. Moreover, the first holder ventilation 1231 is communicated with the second mounting cavity 122 to ensure that the air flows inside the heat dissipation sheet component 420 for heat exchange.

As shown in FIG. 9 to FIG. 14, the holder component 120 includes a heat dissipation sheet holder 124 and a light emitting side holder 125 located on two sides of the thermal conductive structure 410 and connected to each other. The light emitting side holder 125 is provided with the first mounting cavity 121. The heat dissipation sheet holder 124 is provided with the second mounting cavity 122, the first ventilation surface 123, and a mounting port 1241. The heat dissipation sheet component 420 is mounted in the second mounting cavity 122 through the mounting port 1241. The heat dissipation sheet component 420 is mounted in the housing component 100 by the heat dissipation sheet holder 124, and the light emitting component 200 is mounted in the housing component 100 by the light emitting side holder 125. On one hand, it is easy to disassemble and assemble the heat dissipation sheet component 420 and the light emitting component 200, thus reducing the difficulty of disassembly and disassembly. On the other hand, the positions of the heat dissipation sheet component 420 and the light emitting component 200 in the housing component 100 are fixed to prevent the two components from moving or shifting and affecting the internal structural stability of the skin treatment apparatus. The heat dissipation sheet component 420 is detachable through the mounting port 1241, which is easy and simple for workers to disassemble and assemble the heat dissipation sheet component 420, thus reducing the difficulty of disassembly and disassembly. Further, the heat dissipation sheet holder 124 and the light emitting side holder 125 form heat dissipation channels for dissipating heat from the heat dissipation sheet component 420 and the light emitting component 200, thereby improving the heat dissipation effect.

As shown in FIG. 2 to FIG. 4, the skin treatment apparatus further includes a fan 500, which is disposed in the accommodation cavity and located on the side of the heat dissipation sheet component 420 away from the light outlet 11. The heat dissipation sheet holder 124 is defined with a second air vent 1242, and an air outlet of the fan 500 is communicated with the second mounting cavity 122 through the second air vent 1242. In this way, the cold air blown out from the air outlet of the fan 500 enters the second mounting cavity 122 through the second air vent 1242 and exchanges heat with the heat dissipation sheet component 420. This ensures that the cold air is blown to the heat dissipation sheet component 420 for cooling.

As shown in FIG. 9 to FIG. 12, the heat dissipation sheet holder 124 includes a first holder. The first holder includes a first support part 131, a first side support part 132, a second support part 133 and a second side support part 134. The first support part 131 and the second support part 133 face each other, and are both connected to the second side support part 134. The first side support part 132 faces the second side support part 134. The second support part 133 is disposed away from the light outlet 11 with respect to the first support part 131.

The first support part 131, the first side support part 132, the second support part 133, and the second side support part 134 enclose to form the second mounting cavity 122 and the first air vent 1231. The sides walls of the first support part 131, the first side support part 132, the second support part 133, and the second side support part 134 away from the light emitting component 200 form the first ventilation surface 123. The second support part 133, the first side support part 132, and the second side support part 134 enclose to form the second air vent 1242.

In this way, a relatively large space is formed in the middle of the heat dissipation sheet holder 124, which can accommodate the heat dissipation sheet component 420. Besides, the multiple support parts ensure the structural strength. Further, the heat dissipation sheet holder 124 has a simple structure, which is easy to form the first air vent 1231, the first ventilation surface 123, and the second air vent 1242.

A gap is formed between the first support part 131 and the inner wall of the housing 110, such that the air in the second mounting cavity 122 can flow to the housing air outlet part 1201 through the gap, and then flows to the outside of the housing 110 through the housing air outlet part 1201.

In some embodiments, the first support part 131 includes a first support plate disposed laterally, the second support part 133 includes a second support plate disposed laterally, the first side support part 132 includes a third support plate disposed longitudinally, and the second side support part 134 includes a fourth support plate disposed longitudinally. One end of the first support plate 1311 is connected with an inner surface of the third support plate, and the other end of the first support plate 1311 is connected with an inner surface of the fourth support plate. One end of the second support plate 1321 is connected with an inner surface of the third support plate, and the other end of the second support plate 1321 is connected with an inner surface of the fourth support plate. The side edge of the second support plate facing the fan 500, the side edge of the third support plate facing the fan 500, and the side edge of the fourth support plate facing the fan 500 enclose to form the second air vent 1242. The side edge of the first support plate facing the third support plate, the third support plate, the fourth support plate, and the side edge of the second support plate facing the first support part 131 enclose to form the first air vent 1231. The above arrangement makes it easier and simpler to process the first air vent 1231 and the second air vent 1242, thereby reducing the processing cost and processing difficulty of the first holder, and improving the structural strength and the ventilation performance of the first holder. This ensures that the cold air blown from the air outlet of the fan 500 enters the first holder to cool the heat dissipation sheet component 420.

Optionally, the housing component 100 includes the housing air outlet part 1201. The side edge of the first support plate away from the fan 500, the side edge of the third support plate away from the fan 500, and the side edge of the fourth support plate away from the fan 500 enclose to form a third air vent 135, which is communicated with the second mounting cavity 122 and the housing air outlet part 1201.

Optionally, the first support plate 1311 faces the first sub-transition surface 4241 of the heat dissipation sheet component 420.

Optionally, in the light output direction of the light emitting component 200, at least part of the side edge of the third support plate away from the light emitting component 200 and at least part of the side edge of the fourth support plate away from the light emitting component 200 gradually bend toward the second side plate 113, to make at least part of the first ventilation surface 123 gradually bend toward the second side plate 113.

Optionally, the missing corner is located in the first air vent 1231.

The third air vent 135 allows the airflow to flow smoothly within the housing 110, avoiding the accumulation of hot air that may affect the heat dissipation performance of the skin treatment apparatus. In addition, the first holder fits the outer shape of the housing 110, which prevents the structural interference between the first holder and the housing 110 that may affect the disassembly and assembly of the skin treatment apparatus.

Optionally, the inner side wall of the third support plate 1321 is provided with a first air blocking protrusion part 136. The first air blocking protrusion part 136 is disposed close to the side edge of the second support plate away from the light emitting component 200, and the first air blocking protrusion part 136 extends along an extension direction of this side edge.

It can be understood that by providing first air blocking protrusion part 136, the air entering the gap between the heat dissipation sheet component 420 and the third support plate 1321 flows out of the gap through the first air vent less quickly, thereby increasing the interaction time with the heat dissipation sheet component.

Optionally, the inner side wall of the fourth support plate 1341 is provided with a second air blocking protrusion part 137. The second air blocking protrusion part 137 is disposed close to the side edge of the third support plate away from the light emitting component 200, and the second air blocking protrusion part 137 extends along an extension direction of this side edge.

It can be understood that by providing the second air blocking protrusion part 137, the air entering the gap between the heat dissipation sheet component 420 and the fourth support plate 1341 flows out of the gap through the first air vent less quickly, thereby increasing the interaction time with the heat dissipation sheet component.

Optionally, the inner side wall of the fourth support plate 1341 is provided with a third air blocking protrusion part 138. The third air blocking protrusion part 138 is disposed close to the first support part 131 with respect to the second support part 133, and the third air blocking protrusion part 138 extends along a direction close to or away from the light emitting component 200.

It can be understood that by providing the third air blocking protrusion part 138, the air entering the gap between the heat dissipation sheet component 420 and the fourth support plate 1341 flows out of the gap through the first air vent less quickly, thereby increasing the interaction time with the heat dissipation sheet component.

In this way, the air blocking protrusion parts play the roles of supporting and limiting to avoid the heat dissipation sheet component 420 from shaking or moving, and also allow the ventilation gaps to be formed between the heat dissipation sheet component 420 and the first holder, ensuring that the airflow after heat exchange with the heat dissipation sheet component 420 is discharged to the outside of the housing 110 through the ventilation gaps.

Figure 10:
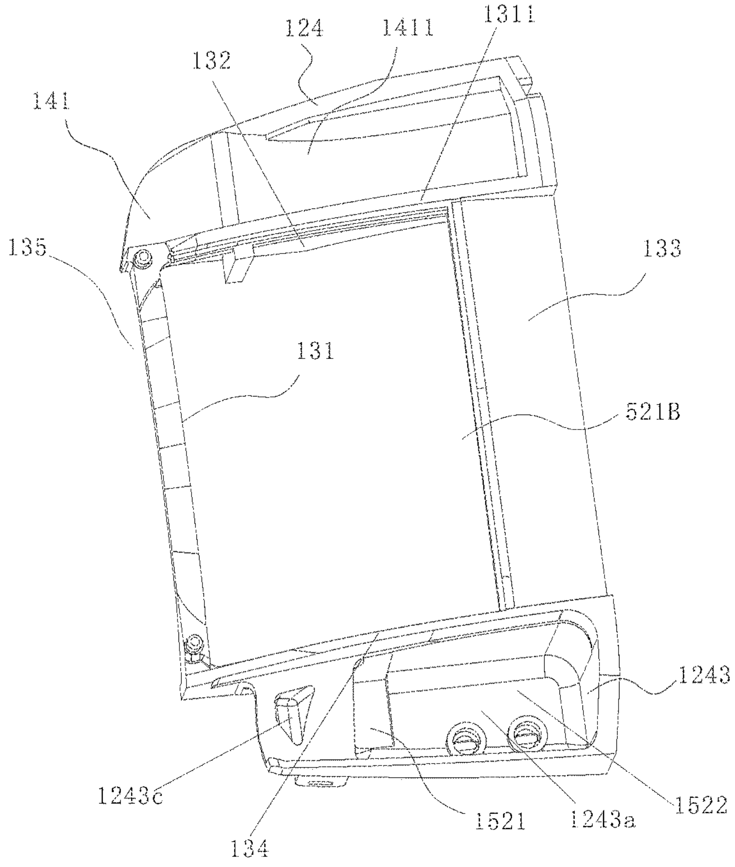
FIG. 10 is a perspective view of the heat dissipation fin holder in FIG. 9 from a first perspective.
Figure 11:
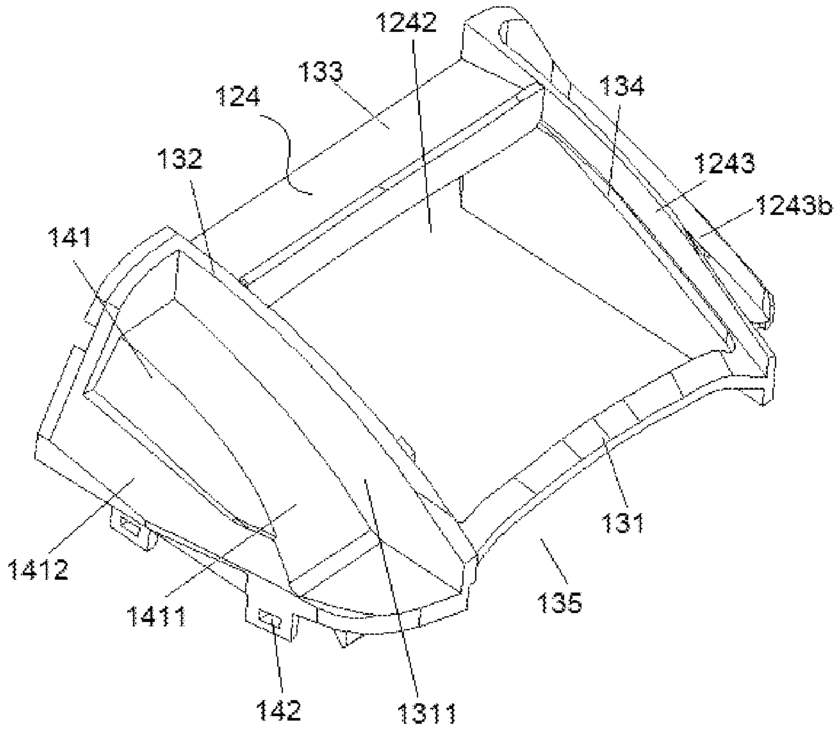
FIG. 11 is a perspective view of the heat dissipation fin holder in FIG. 9 from a second perspective.

As shown in FIG. 9 to FIG. 11, the heat dissipation sheet holder 124 further includes a first outer support part 141 disposed on an outer side wall of the first side support part 132. The first outer support part 141 is connected to the light emitting side holder 125.

As shown in FIG. 9 to FIG. 11, the heat dissipation sheet holder 124 further includes a second outer support part 1243 disposed on an outer side wall of the second side support part 134. The second outer support part 1243 is connected to the light emitting side holder 125.

In this way, the heat dissipation sheet holder 124 is connected to the light emitting side holder 125 by the first outer support part 141 and the second outer support part 1243, so that the mounting position of the holder component 120 in the housing 110 is fixed, thereby preventing the holder component 120 from moving or shifting in the housing 110 and affecting the overall structural stability of the skin treatment apparatus. In addition, the mounting positions of the heat dissipation sheet holder 124 and the light emitting side holder 125 avoid the mounting position of the heat dissipation sheet component 420, thereby preventing the connection between the heat dissipation sheet holder 124 and the light emitting side holder 125 from affecting the normal heat dissipation of the heat dissipation sheet component 420.

Figure 12:
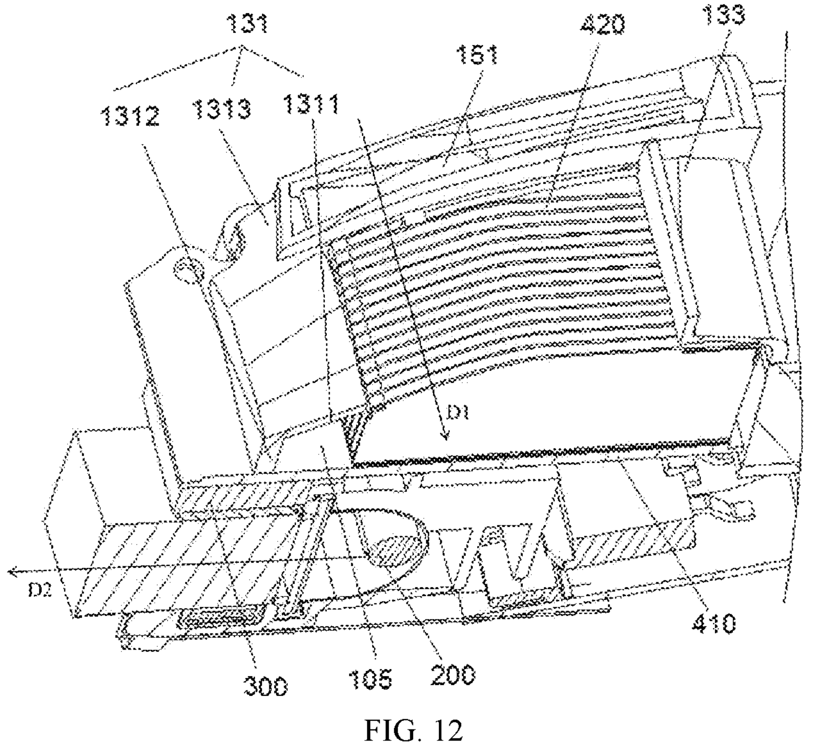
FIG. 12 is a sectional diagram of a skin treatment apparatus according to a second embodiment of the present disclosure.
Figure 14:
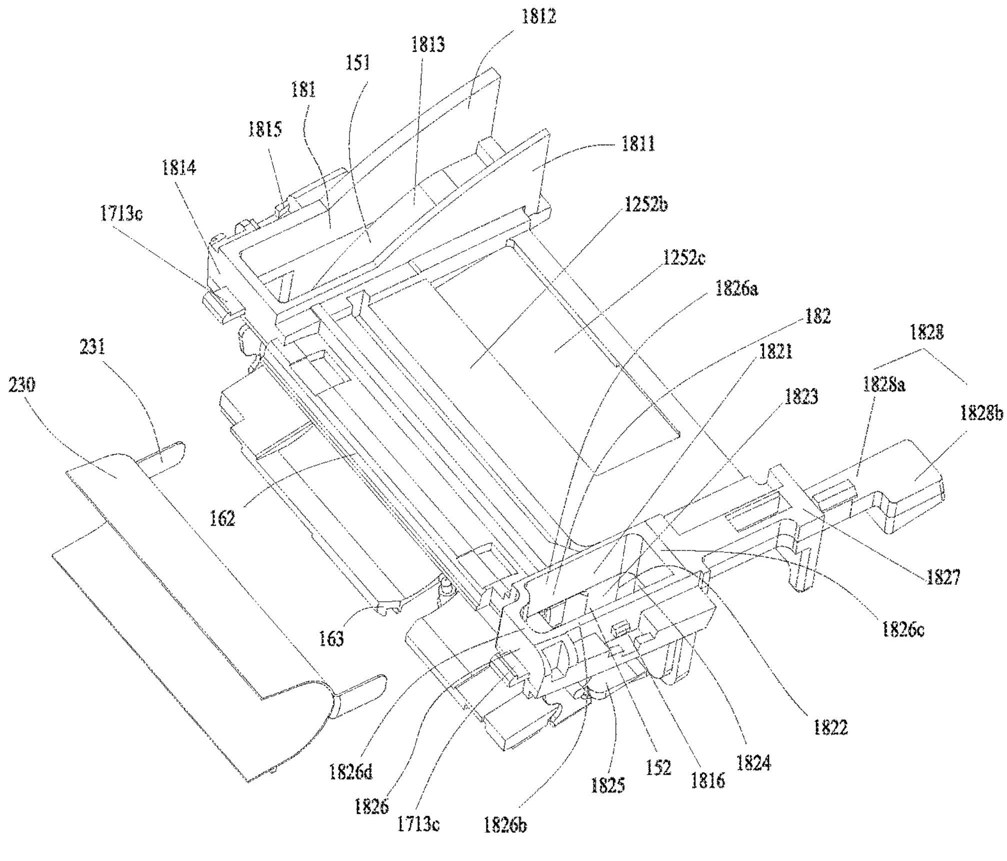
FIG. 14 is an exploded diagram of the second holder and the reflector in FIG. 13.

As shown in FIG. 12 and FIG. 14, the housing component 100 includes the housing air outlet part 1201. The first outer support part 141 and the light emitting side holder 125 enclose to form a first ventilation flow channel 151. The first ventilation flow channel 151 is communicated with the air outlet of the fan 500 and the first mounting cavity 121. In the light output direction of the light emitting component 200, at least part of the first ventilation flow channel 151 gradually bends toward the side away from the first extension section 1121.

And/or, the second outer support part 1243 and the light emitting side holder 125 enclose to form a second ventilation flow channel 152. The second ventilation flow channel 152 is communicated with the housing air outlet part 1201 and the first mounting cavity 121.

In this way, the first ventilation flow channel 151 is formed by the first outer support part 141, to guide the air entering the first mounting cavity 121; and/or, the second ventilation flow channel 152 is formed by the second outer support part 1243, to guide the air flowing out from the first mounting cavity 122.

In an embodiment, the air blown out from the fan enters the first mounting cavity 121 through the first ventilation flow channel 151, and then flows out of the first mounting cavity 121 through the second ventilation flow channel 152, so as to dissipate the heat from the light emitting component.

As shown in FIG. 9 to FIG. 11, the first outer support part 141 includes a first air duct plate 1411 and a second air duct plate 1412. The first air duct plate 1411 is disposed on the outer side wall of the third support plate. The second air duct plate 1412 is connected to the side edge of the first air duct plate 1411 away from the first support plate. The second air duct plate 1412 faces the third support plate 1321. The first air duct plate 1411, the third support plate 1321 and the second air duct plate 1412 enclose to form a part of the first ventilation flow channel 151. In the light output direction of the light emitting component 200, at least part of the first air duct plate 1411 gradually bend toward the side away from the first extension section 1121, so that at least part of the first ventilation flow channel 151 gradually bend toward the side away from the first extension section 1121.

And/or, as shown in FIG. 9 and FIG. 11, the second outer support part 1243 includes a first flow duct plate **1243*a* and a second flow duct plate 1243*b*. The first flow duct plate 1243*a* is disposed on the outer side wall of the fourth support plate 1341. The second flow duct plate 1243*b* is connected to the side edge of the first flow duct plate 1243*a* away from the second support plate 1331. The second flow duct plate 1243*b* faces the fourth support plate 1341. The second ventilation flow channel 152 includes a ventilation through port 1521 and a diffuser auxiliary cavity 1522. The ventilation through port 1521 is disposed in the first flow duct plate 1243*a*. The first flow duct plate 1243*a*, the second flow duct plate 1243*b* and the fourth support plate 1341 enclose to form the diffuser auxiliary cavity 1522. The diffuser auxiliary cavity 1522 is communicated with the housing air outlet part 1201. The diffuser auxiliary cavity 1522 is communicated with the first mounting cavity 121 through the ventilation through port 1521. The second outer support part 1243 further includes a light-blocking flow guiding part 1243*c* disposed on the fourth support plate 1341 and the second flow channel 1243*b*. The light-blocking flow guiding part 1243*c* at least partially covers the ventilation through port 1521**.

In this way, the first ventilation flow channel 151 is an arc-shaped channel to ensure that the cold air blown from the air outlet of the fan 500 enters the light emitting component 200 through the arc-shaped channel for cooling the light emitting component 200. The second ventilation flow channel 152 includes the ventilation through port 1521 and the diffuser auxiliary cavity 1522, to diffuse the air flowing out of the first mounting cavity 121 and thereby preventing the heat accumulation.

Moreover, the air flowing out from the downstream of the light emitting component 200 can be divided at the light-blocking flow guiding part **1243*c* into at least two airflows and then be discharged from the housing air outlet part 1201, to prevent the heat accumulation at the downstream of the light emitting component 200 that may cause the heating of the light emitting component 200**.

Illustratively, a part of the airflow blown out from the air outlet of the fan 500 directly enters the second mounting cavity 122 to cool the heat dissipation sheet component 420; the other part of the airflow enters the first ventilation flow channel 151, passes through the light emitting component 200, and then is discharged through the second ventilation flow channel 152. The diffuser auxiliary cavity 1522 located in the second ventilation flow channel 152 can increase the outlet space of the second ventilation flow channel 152, such that the hot air after cooling the light emitting component 200 can be quickly discharged through the second ventilation flow channel 152 to avoid the heat accumulation.

Optionally, the first air duct plate 1411 and/or the second air duct plate 1412 is provided with a first engagement part 142 that is engaged with the light emitting side holder 125; and/or, the first flow duct plate **1243*a* and/or the second flow duct plate 1243*b* is provided with a second engagement part 143 that is engaged with the light emitting side holder 125. In this way, the first holder is engaged with the light emitting side holder 125, realizing a detachable connection therebetween. It is easier and simpler to detach the first holder and the light emitting side holder 125**, thus reducing the difficulty of disassembly and assembly.

As shown in FIG. 2 to FIG. 6, the cold compress component 300 includes the light transmitting member 310. The light emitting side holder 125 is further defined with a third mounting cavity 1251 disposed between the first mounting cavity 121 and the light outlet 11. The light transmitting member 310 is mounted in the third mounting cavity 1251. The light-transmitting member 310 is configured to touch the skin to be treated so as to cool the skin to be treated or the skin in the vicinity of the skin to be treated.

Figure 13:
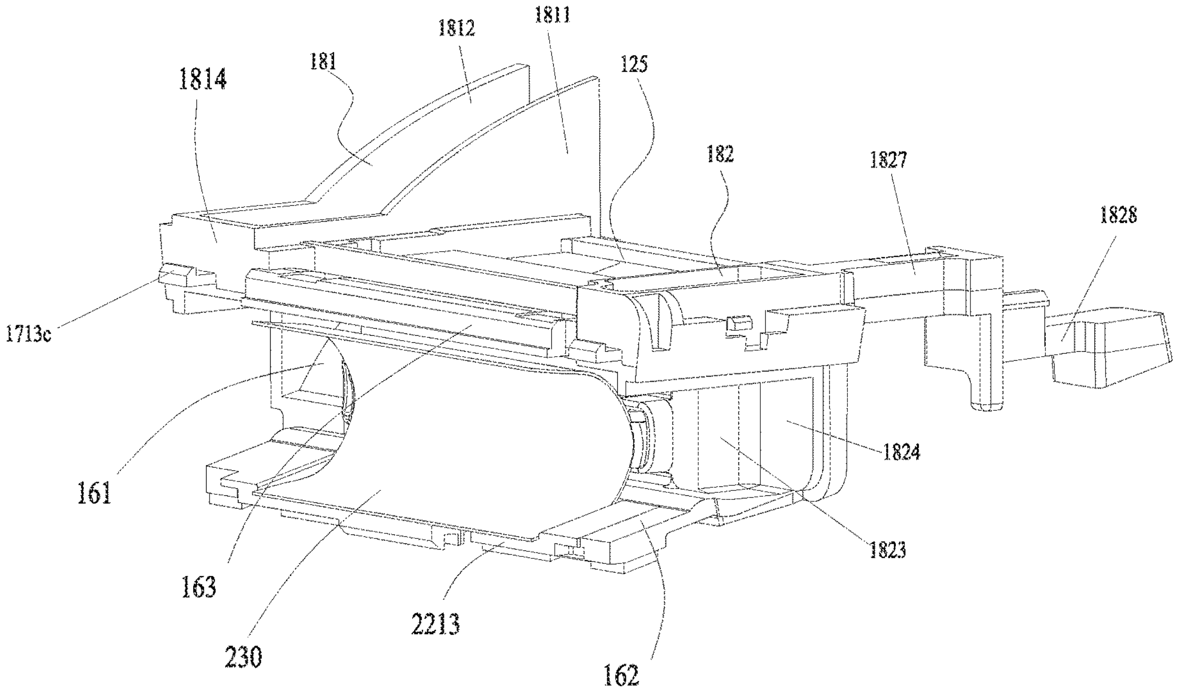
FIG. 13 is a perspective view of a second holder and a reflector of the holder component in FIG. 4 in assembly.

As shown in FIG. 13 and FIG. 14, the light emitting side holder 125 includes a second holder 1252 and a third holder 1253 located between the second holder 1252 and the light outlet 11. The second holder 1252 is defined with the first mounting cavity 121 and a holder light outlet 1252*a*. The first mounting cavity 121 is communicated with the light outlet 11 through the holder light outlet 1252*a*. The third holder 1253 is connected to the second holder 1252 and is provided with the third mounting cavity 1251. The second holder 1252 is configured to support and fix the light emitting component 200, so as to prevent the light emitting component 200 from moving or shifting in the housing component 100 and affecting the internal structural stability of the skin treatment apparatus. The third holder 1253 is configured to support and fix the light transmitting member 310, so as to prevent the light transmitting member 310 from moving or shifting in the housing component 100 and affecting the internal structural stability of the skin treatment apparatus.

As shown in FIG. 13 and FIG. 14, the second holder 1252 includes a first mounting plate 161, a first side part 162 disposed on one side of the first mounting plate 161, and a second side part 163 disposed on the other side of the first mounting plate 161. The first mounting plate 161 faces the light outlet 11. The first mounting plate 161, the first side part 162 and the second side part 163 enclose to form the first mounting cavity 121. The holder light outlet 1252*a* is formed between the first side part 162 and the second side part 163. In this way, the second holder 1252 is in a U-shaped structure, which limits the light output direction of the light emitting component 200, thereby ensuring that the light generated by the light emitting component 200 is directed to the light outlet 11 after passing through the holder light outlet 1252*a*.

As shown in FIG. 12 to FIG. 14, the light emitting component 200 includes the light emitting member 210 and a reflector 230. The reflector 230 is disposed around the light emitting member 210.

As shown in FIG. 12 to FIG. 14, the first mounting plate 161 is defined with a mounting insertion hole, the reflector 230 is provided with an insertion pin 231. The insertion pin 231 is inserted into the mounting insertion hole.

As shown in FIG. 12 to FIG. 14, the inner side surface of the first mounting plate 161 is provided with an abutting protrusion part. The reflector 230 abuts against the abutting protrusion part, to form the ventilation gap between the reflector 230 and the inner side surface of the first mounting plate 161.

The reflector 230 is detachably connected to the first mounting plate 161, thus it is easy to assemble and disassemble the reflector and the first mounting plate 161, reducing the difficulty of assembly and disassembly. In addition, the cold air entering the first ventilation flow channel 151 can pass through the ventilation gap, to flow smoothly in the light emitting component 200 and exchange heat.

As shown in FIG. 33 to FIG. 38, the light emitting component 200 further includes the filter 220 and a sealing structure 240. The filter 220 is disposed between the light emitting member 210 and the light transmitting member 310. The sealing structure 240 seals the gap between the filter 220 and the light transmitting member 310.

In an embodiment, the sealing structure 240 is located outside a spot of light irradiated on the filter 200 by the light emitting member 210. Since the sealing structure 240 is located outside a covering space of a light emitting outlet of the light emitting member 210, the light exiting from the light emitting outlet will not be irradiated directly on the sealing structure 240. This avoids the problem in related art that the sealing structure is susceptible to deterioration and carbonization under long-term light exposure, thus improving the service life of the sealing structure 240 and the skin treatment apparatus, and preventing the production of powdery debris which may affect the light effect.

Figure 15:
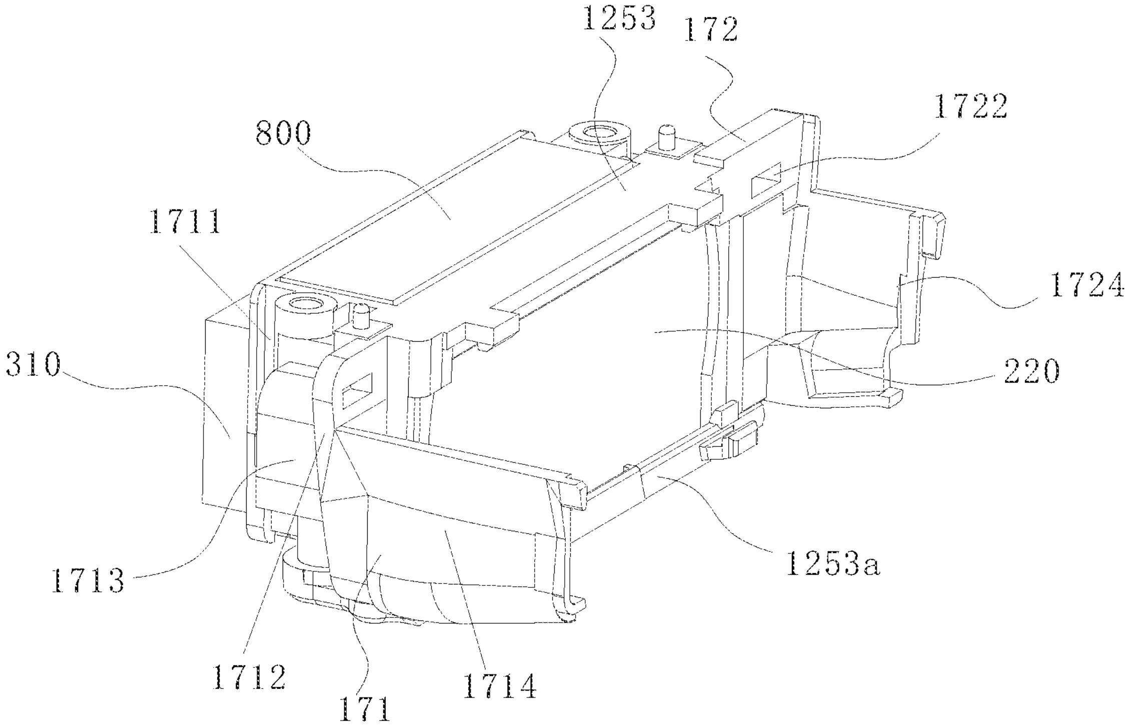
FIG. 15 is a perspective view of a third holder of the holder component in FIG. 4.
Figure 16:
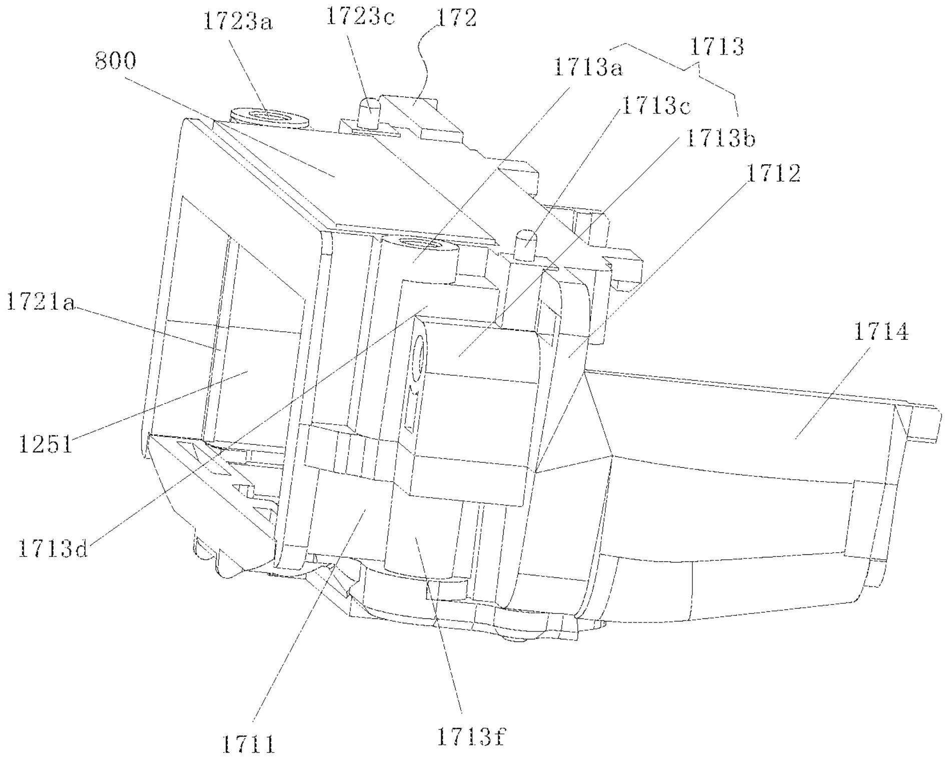
FIG. 16 is a perspective view of the third holder in FIG. 15 from a first perspective.
Figure 17:
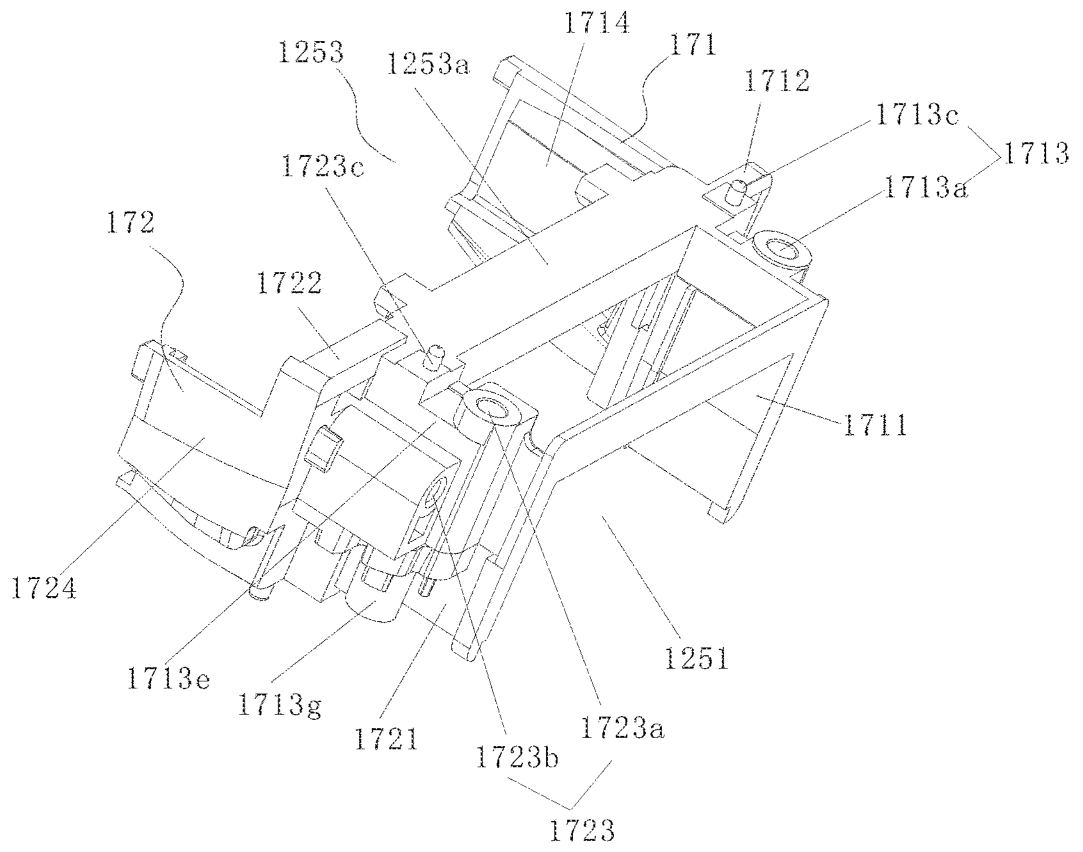
FIG. 17 is a perspective view of the third holder in FIG. 15 from a second perspective.

As shown in FIG. 15 to FIG. 17, the first mounting cavity 121 are open on two sides. The third holder 1253 includes a first connection support part 171 and a second connection support part 172 extending toward the second holder 1252. The first connection support part 171 and the second connection support part 172 are both connected to the second holder 1252 and cover the two openings. In this way, the first connection support part 171 and the second connection support part 172 help to avoid the light leakage of the light emitting component 200 which may affect the user experience, and ensure that all the light generated by the light emitting member 210 is emitted through the light outlet 11.

As shown in FIG. 13 and FIG. 14, the second holder 1252 further includes a first flow guiding part 181 disposed at an end of the first mounting plate 161, the first side part 162 and the second side part 163. The first flow guiding part 181 cooperates with the heat dissipation sheet holder 124 to form the first ventilation flow channel 151 that is communicated with the first mounting cavity 121.

As shown in FIG. 13 and FIG. 14, the second holder 1252 further includes a second flow guiding part 182 disposed at the other end of the first mounting plate 161, the first side part 162 and the second side part 163. The second flow guiding part 182 cooperates with the heat dissipation sheet holder 124 to form the second ventilation flow channel 152 that is communicated with the first mounting cavity 121. The first flow guiding part 181 is docked with the first outer support part 141 to form the first ventilation flow channel 151; and/or, the second flow guiding part 182 is docked with the second outer support part 1243 to form the second ventilation flow channel 152, so that the cold air blown out from the air outlet of the fan 500 enters the ventilation flow channel to cool the light emitting component 200, thereby preventing a high surface temperature of the light emitting component 200 from affecting its service life.

As shown in FIG. 13 and FIG. 14, the first flow guiding part 181 includes a first flow guiding side plate 1811, a second flow guiding side plate 1812 and a third flow guiding side plate 1813. The second flow guiding side plate 1812 faces the first flow guiding side plate 1811. The third flow guiding side plate 1813 is connected to the first flow guiding side plate 1811, the second flow guiding side plate 1812 and the second side part 163. The first flow guiding side plate 1811, the second flow guiding side plate 1812 and the third flow guiding side plate 1813 enclose to form at least part of the first ventilation flow channel 151. The first flow guiding part 181 has a simple structure which is easy to process and implement, thereby reducing the overall processing cost and difficulty of the skin treatment apparatus.

Optionally, in the light output direction of the light emitting component 200, at least part of the third flow guiding side plate 1813 gradually bends toward the side away from the first extension section 1121.

As shown in FIG. 13 and FIG. 14, the first flow guiding side plate 1811, the second flow guiding side plate 1812 and the third flow guiding side plate 1813 all extend toward the side away from the light outlet 11.

As shown in FIG. 13 and FIG. 14, the first flow guiding part 181 further includes a fourth flow guiding side plate 1814. The fourth guide side plate 1814 is connected to the first flow guiding side plate 1811 and the second flow guiding side plate 1812. The surface of the fourth flow guiding side plate 1814 facing the third holder 1253 is provided a third engagement part 1815 that is engaged with the third holder 1253.

As shown in FIG. 13 and FIG. 14, the outer side surface of the second guide side plate 1812 is provided with a fourth engagement part 1816 that is engaged with the heat dissipation sheet holder 124. In this way, the first ventilation flow channel 151 is an arc-shaped flow channel, to ensure that the cold air blown out from the air outlet of the fan 500 is blown to the light emitting member 210 through the arc-shaped flow channel. In addition, the engagement position of the first holder and the light emitting side holder 125 is convenient for a user to operate, thus reducing the difficulty of disassembly and assembly.

Illustratively, the first engagement part 142 is engaged with the fourth engagement part 1816 in FIG. 14, and the second engagement part 143 is engaged with a fifth engagement part 1829*a* in FIG. 13.

As shown in FIG. 13 and FIG. 14, the second ventilation flow channel 152 includes the diffuser auxiliary cavity 1522. The part of the second flow guiding part 182 located at the opening of the first mounting cavity 121 is defined with a diffuser cavity 1821 and a diffuser hole 1822 communicated with each other. The diffuser cavity 1821 is communicated with the diffuser auxiliary cavity 1522 through the diffuser hole 1822. The airflow blown out from a downstream side of the light emitting component 200 passes through the diffuser cavity 1821 and the diffuser hole 1822, and enters the diffuser auxiliary cavity 1522, and finally is discharged through the housing air outlet part 1201, so that the hot air can be quickly discharged from the downstream of the light emitting member 210, to prevent the heat accumulation from resulting in heating of the light emitting component 200.

As shown in FIG. 13 and FIG. 14, the second flow guiding part 182 includes a first diffuser plate 1823, a second diffuser plate 1824, a third diffuser plate 1825, and a ventilation part 1826. The first diffuser plate 1823 is connected to the first mounting plate 161, and the first diffuser plate 1823 extends along the direction away from the light outlet 11. The second diffuser plate 1824 is connected to the first diffuser plate 1823 and located on the side of the first diffuser plate 1823 away from the first mounting plate 161. The third diffuser plate 1825 is connected to the first mounting plate 161, the first diffuser plate 1823, and the second diffuser plate 1824. The ventilation part 1826 is connected to the first diffuser plate 1823 and the second diffuser plate 1824. The third diffuser plate 1825 faces the ventilation part 1826. The ventilation part 1826 is provided with the diffuser hole 1822. It is easy and simple to form the diffuser cavity 1821 and the diffuser hole 1822, thus reducing the processing cost and processing difficulty of the second holder 1252.

As shown in FIG. 13 and FIG. 14, the ventilation part 1826 includes a first ventilation plate 1826*a*, a second ventilation plate 1826*b*, a third ventilation plate 1826*c*, and a fourth ventilation plate 1826*d*. The first ventilation plate 1826*a* is connected to the first diffuser plate 1823 and the first side part 162. The second ventilation plate 1826*b* faces the first ventilation plate 1826*a*. The third ventilation plate 1826*c* is connected to the second diffuser plate 1824, the first ventilation plate 1826*a*, and the second ventilation plate 1826*b*. The fourth ventilation plate 1826*d* faces the third ventilation plate 1826*c*, and is connected to the first ventilation plate 1826*a* and the second ventilation plate 1826*b*. The first ventilation plate 1826*a*, the second ventilation plate 1826*b*, the third ventilation plate 1826*c*, and the fourth ventilation plate 1826*d* enclose to form the diffuser hole 1822. The ventilation part 1826 is annular, to ensure that the hot air discharged from the downstream of the light emitting component 200 is quickly and fully discharged through the ventilation part 1826, thereby avoiding the accumulation of the hot air at the downstream of the light emitting component 200.

Optionally, the outer side surface of the second ventilation plate 1826*b* is provided with the fifth engagement part 1829*a* that is engaged with the heat dissipation sheet holder 124; and/or, the outer side surface of the fourth ventilation plate 1826*d* is provided with a sixth engagement part that is engaged with the third holder 1253.

As shown in FIG. 13 and FIG. 14, the diffuser hole 1822 has a preset hole depth. Optionally, the preset hole depth is greater than or equal to 1.5 cm, such as 1.8 cm, 2 cm, 2.3 cm, 2.5 cm, 2.8 cm, 3 cm, or 3.2 cm.

In this way, the engagement position of the first holder and the light emitting side holder 125 is convenient for a user to operate, thus reducing the difficulty of disassembly and assembly. In addition, the diffuser hole 1822 can guide the hot air after the cooling is completed to ensure that the hot air is smoothly discharged from the housing air outlet part 1201.

Figure 20:
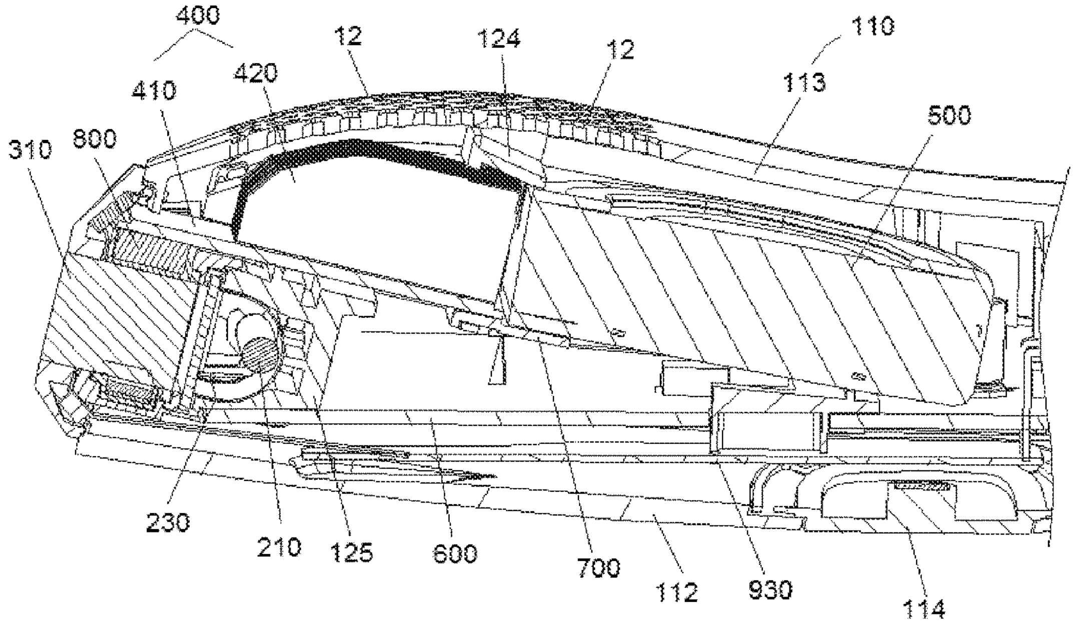
FIG. 20 is a structural schematic diagram of a skin treatment apparatus according to an embodiment of the present disclosure.

As shown in FIG. 14 and FIG. 20, the skin treatment apparatus further includes a main control board 600, and the second holder 1252 further includes a heat dissipation support plate 1252*b*. The heat dissipation support plate 1252*b* is disposed on the side of the first mounting plate 161 away from the light outlet 11, and is connected to the first mounting plate 161 and the first side part 162. A weight reduction hole 1252*c* and a first connection post are disposed on the heat dissipation support plate 1252*b*. The first connection post is located on the side of the heat dissipation support plate 1252*b* away from the heat dissipation component 400, so that the main control board 600 and the second holder 1252 are connected by inserting a fastener into the main control board 600 and the first connection post. In this way, the heat dissipation support plate 1252*b* is configured to support part of the first holder and is connected to the main control board 600, so as to fix the mounting positions of the main control board 600 and the second holder 1252 in the housing 110, thereby preventing the internal structure of the skin treatment apparatus from moving or shifting and affecting the structural stability. In addition, the main control board 600 is connected to the light emitting member 210 and the fan 500, so as to control a light emitting state of the light emitting member 210, an ON/OFF state and a rotation speed of the fan 500.

Figure 21:
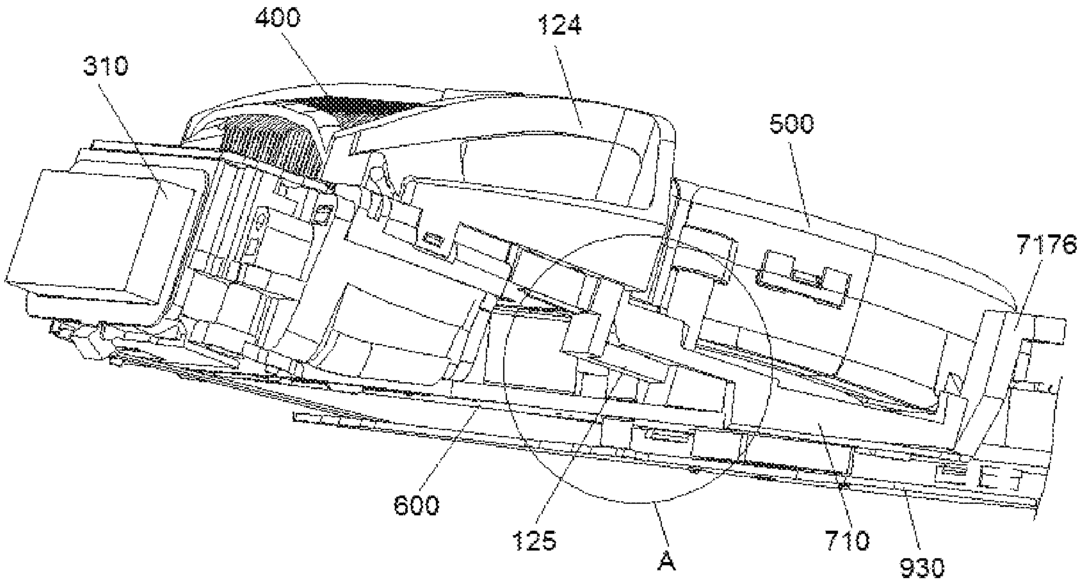
FIG. 21 is a structural schematic diagram of the skin treatment apparatus in FIG. 20 with the housing being removed.
Figure 23:
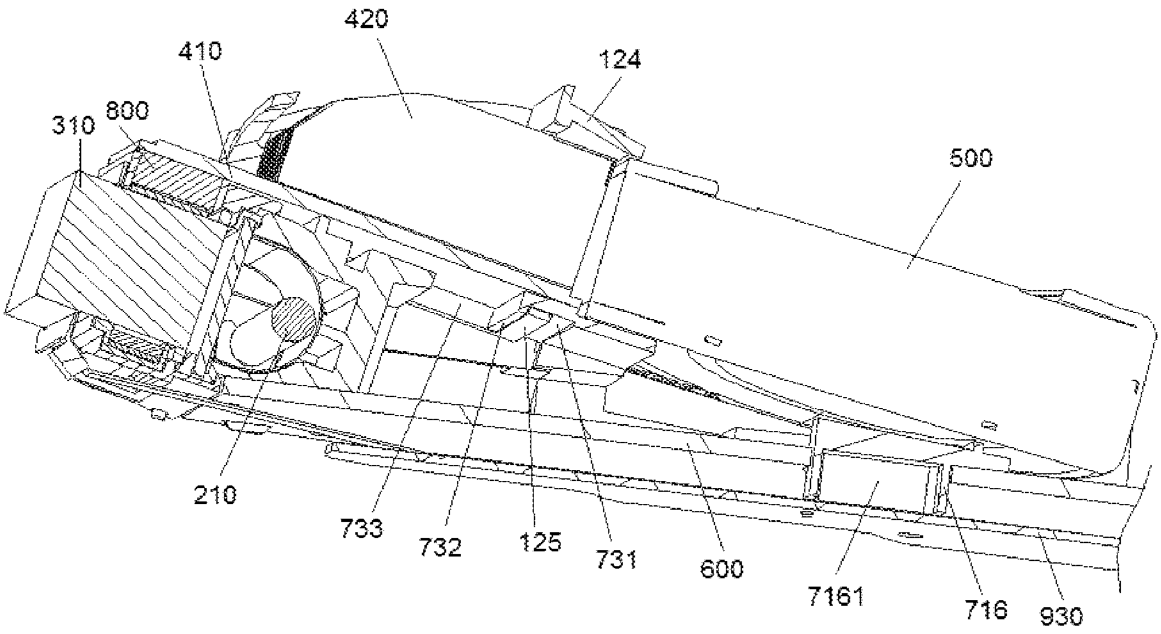
FIG. 23 is a sectional diagram of the skin treatment apparatus in FIG. 21.

Illustratively, the weight reduction hole 1252*c* helps to reduce the overall weight of the second holder 1252, so as to realize a lightweight design of the second holder 1252, thereby improving the user experience. In addition, as shown in FIG. 21 and FIG. 23, the heat dissipation component (specifically, the thermal conductive structure) is mounted on the heat dissipation support plate 1252*b*, and the weight reduction hole 1252*c* is further configured to dissipate heat from the thermal conductive structure.

As shown in FIG. 20 to FIG. 31, the skin treatment apparatus further includes a fan holder 700. The fan 500 is disposed on the fan holder 700. The second flow guiding part 182 further includes a first support section 1827 and a second support section 1828. The first support section 1827 is disposed on the third ventilation plate 1826*c* and extends toward the side away from the light outlet 11. The first support section 1827 is configured to support the heat dissipation sheet holder 124. The second support section 1828 is disposed on the first support section 1827 and extends toward the side away from the light outlet 11. The second support section 1828 extends between the fan holder 700 and the main control board 600, and is in contact with the fan holder 700 and/or the main control board 600. In this way, the first support section 1827 is configured to support the heat dissipation sheet holder 124, and the second support section 1828 is in contact with and abuts against the fan holder 700 and the main control board 600 to limit the positions of the fan holder 700 and the main control board 600. This prevents the two from moving or shifting relative to the housing 110 and affecting the internal structural stability of the skin treatment apparatus.

As shown in FIG. 14, the second support section 1828 includes a support bar 1828*a* and a support block 1828*b*. One end of the support bar 1828*a* is connected with the first support section 1827, and the other end of the support bar 1828*a* is connected with the support block 1828*b*. The support block 1828*b* includes two support surfaces facing each other. The two support surfaces form an included angle. One support surface is in contact with the fan holder 700, and the other support surface is in contact with the main control board 600. And/or, the skin treatment apparatus further includes a cooling plate 800. The cold compress component 300 is thermally connected with the first thermal conductive section 411 by the cooling plate 800. The third holder 1253 further includes a second mounting plate 1253*a*. One end of the second mounting plate 1253*a* is connected with the first connection support part 171, and the other end of the second mounting plate 1253*a* is connected with the second connection support part 172. The second mounting plate 1253*a* is defined with a mounting hole 1253*b*. The cooling plate 800 is disposed in the mounting hole 1253*b*. The second mounting plate 1253*a*, the first connection support part 171 and the second connection support part 172 enclose to form the third mounting cavity 1251. The second support section 1828 has a simple structure which is easy to process and implement, thus reducing the processing cost of the second support section 1828. Moreover, the third holder 1253 may be configured to mount the cooling plate 800, so as to support and fix the cooling plate 800. With this arrangement, it is ensured that the cold compress component 300 is thermally connected to the first thermal conductive section 411 by the cooling plate 800, thereby improving the heat dissipation performance of the heat dissipation component 400.

As shown in FIG. 15 to FIG. 17, the first connection support part 171 includes a first support part side plate 1711, a second support part side plate 1712, a first connection component 1713, and a first extension plate 1714. The second support part side plate 1712 is disposed on the outer side surface of the first support part side plate 1711, and a first receiving cavity is formed between the second support part side plate 1712 and the first support part side plate 1711. The first connection component 1713 is disposed in the first receiving cavity, and is configured to be connected to the thermal conductive structure 410 and/or the main control board 600. The first extension plate 1714 is disposed on the surface of the second support part side plate 1712 away from the light outlet 11. The first extension plate 1714 extends toward the side away from the light outlet 11 and then is docked with the second flow guiding part 182. In this way, the first extension plate 1714 extends to dock with the second flow guiding part 182 so as to shield one side of the light emitting component 200. This prevents the occurrence of light leakage from light emitting component 200 that may affect the user experience, and ensures that all the light generated by the light emitting member 210 comes out through the light outlet 11. In addition, the first connection support part 171 has a simple structure which is easy to process and implement, thus reducing the processing cost and processing difficulty of the first connection support part 171.

In some embodiments, the third holder 1253 is connected to the thermal conductive structure 410 and the main control board 600 by the first connection component 1713, such that the third holder 1253 is easier and simpler to disassemble and assemble with the thermal conductive structure 410 and the main control board 600, thereby reducing the difficulty of disassembly and assembly.

As shown in FIG. 15 to FIG. 17, a first mounting notch is defined between a first side edge of the first extension plate 1714 facing the ventilation part 1826 and the second support part side plate 1712, and the ventilation part 1826 is disposed in the first mounting notch and is in contact with the first side edge; and/or, a second mounting notch is defined in a second side edge of the first extension plate 1714 away from the second support part side plate 1712, at least part of the second diffuser plate 1824 extends into the second mounting notch and is in contact with the second side edge; and/or, the side of the first extension plate 1714 away from the ventilation part 1826 bends toward the light emitting side holder 125 and is in contact with the third diffuser plate 1825. In this way, the first extension plate 1714 can be better docked with the second flow guiding part 182 to form a closed cavity, which prevents light leakage and air leakage that may affect the user experience, and also reduces the impact and resistance of the airflow in the second ventilation flow channel 152, thereby allowing the hot air to be quickly discharged from the housing air outlet part 1201.

Optionally, a first connection component mounting cavity is defined between the plate surface of the second support part side plate 1712 facing the light outlet 11 and the outer side surface of the first support part side plate 1711. The first connection component 1713 includes a second connection post 1713*a* and a third connection post 1713*b*. The second connection post 1713*a* is disposed on the first support part side plate 1711 and/or the second support part side plate 1712, and is located in the first connection component mounting cavity, so that the thermal conductive structure 410 and the third holder 1253 are connected by inserting a fastener into the second connection post 1713*a* and the thermal conductive structure 410. The third connection post 1713*b* is disposed on the first support part side plate 1711 and/or the second support part side plate 1712, and is located in the first connection component mounting cavity, so that the housing 110 and the third holder 1253 are connected by inserting a fastener into the third connection post 1713*b* and the housing 110. An extension direction of the second connection post 1713*a* and an extension direction of the third connection post 1713*b* form an included angle. And/or, the first connection component 1713 includes a first engagement protrusion part 1713*c*. The first engagement protrusion part 1713*c* is disposed on the first support part side plate 1711 and/or the second support part side plate 1712, and is located in the first connection component 1713 mounting cavity for engagement with the thermal conductive structure 410. The above arrangement allows for more flexible setting in the positions of the second connection post 1713*a* and/or the third connection post 1713*b*, to meet different user experiences and working conditions, and also improve the processing flexibility. In addition, the third holder 1253 is detachably connected with the thermal conductive structure 410 and the housing 110, which is convenient to disassemble and assemble the skin treatment apparatus, thereby reducing the difficulty of disassembly and assembly.

In some embodiments, the second connection post 1713*a* is disposed on the first support part side plate 1711, so that the thermal conductive structure 410 and the third holder 1253 are connected by inserting a fastener into the second connection post 1713*a* and the thermal conductive structure 410. The third connection post 1713*b* is disposed on the second support part side plate 1712, so that the housing 110 and the third holder 1253 are connected by inserting a fastener into the third connection post 1713*b* and the housing 110. The first engagement protrusion part 1713*c* is disposed on the second support part side plate 1712. In this way, the positions of the second connection post 1713*a*, the third connection post 1713*b* and the first engagement protrusion part 1713*c* make it easy for a worker to disassemble and assemble the third holder 1253, the thermal conductive structure 410 and the housing 110, thus reducing the difficulty of disassembly and assembly.

It should be noted that the position of the second connection post 1713*a* is not limited thereto, and may be adjusted according to working conditions and use requirements. Optionally, the second connection post 1713*a* is disposed on the second support part side plate 1712. Optionally, the second connection post 1713*a* is disposed on the first support part side plate 1711 and the second support part side plate 1712.

It should be noted that the position of the third connection post 1713*b* is not limited thereto, and may be adjusted according to working conditions and use requirements. Optionally, the third connection post 1713*b* is disposed on the first support part side plate 1711. Optionally, the third connection post 1713*b* is disposed on the first support part side plate 1711 and the second support part side plate 1712.

It should be noted that the position of the first engagement protrusion part 1713*c* is not limited thereto, and may be adjusted according to working conditions and use requirements. Optionally, the first engagement protrusion part 1713*c* is disposed on the first support part side plate 1711. Optionally, the first engagement protrusion part 1713*c* is disposed on the first support part side plate 1711 and the second support part side plate 1712.

Optionally, the first connection component 1713 further includes a first connection block 1713*d*. The first connection block 1713*d* is disposed on the first support part side plate 1711 and the second support part side plate 1712, and is located in the first connection component mounting cavity. The second connection post 1713*a* is disposed on the first support part side plate 1711 and the plate surface of the first connection block 1713*d* away from the second support part side plate 1712. The third connection post 1713*b* is disposed on the second support part side plate 1712 and the plate surface of the first connection block 1713*d* away from the first support part side plate 1711. In this way, the second connection post 1713*a* and the third connection post 1713*b* are disposed in the first connection component mounting cavity by the first connection block 1713*d*, which enhances the structural strength of the first connection component 1713 and thereby prolonging the service life of the first connection support part 171.

Optionally, the second connection support part 172 includes a third support part side plate 1721, a fourth support part side plate 1722, a second connection component 1723, and a second extension plate 1724. The fourth support part side plate 1722 is disposed on the outer side surface of the third support part side plate 1721, and a second receiving cavity is formed between the fourth support part side plate 1722 and the third support part side plate 1721. The second connection component 1723 is disposed in the second receiving cavity, and is configured to be connected to the thermal conductive structure 410 and/or the main control board 600. The second extension plate 1724 is disposed on the surface of the second support part side plate 1712 away from the light outlet 11. The second extension plate 1724 extends toward the side away from the light outlet 11 and then is in contact with the second flow guiding side plate 1812 and the third flow guiding side plate 1813. In this way, the second extension plate 1724 extends to dock with the second flow guiding side plate 1812 and the third flow guiding side plate 1813, so as to shield one side of the light emitting component 200. This prevents the occurrence of light leakage from light emitting component 200 that may affect the user experience, and ensures that all the light generated by the light emitting member 210 comes out through the light outlet 11. In addition, the second connection support part 172 has a simple structure which is easy to process and implement, thus reducing the processing cost and processing difficulty of the second connection support part 172.

In some embodiments, the third holder 1253 is connected to the thermal conductive structure 410 and the main control board 600 by the second connection component 1723, such that the third holder 1253 is easier and simpler to disassemble and assemble with the thermal conductive structure 410 and the main control board 600, thereby reducing the difficulty of disassembly and assembly.

Optionally, a third mounting notch is formed between a first side edge of the second extension plate 1724 facing the fourth support part side plate 1722 and the fourth support part side plate 1722, and the fourth support part side plate 1722 is disposed in the third mounting notch and is in contact with the first side edge; and/or, a fourth mounting notch is defined in a second side edge of the second extension plate 1724 away from the fourth support part side plate 1722, and at least part of the second flow guiding side plate 1812 and at least part of the third flow guiding side plate 1813 extend into the fourth mounting notch and are in contact with the second side edge. In this way, the second extension plate 1724 is docked with the first flow guiding part 181 to form a closed cavity, which can prevent light leakage and air leakage that may affect the user experience, and reduce the impact and resistance of the airflow in the first ventilation flow channel 151. Therefore, the hot air can be quickly discharged from the housing air outlet part 1201.

As shown in FIG. 15 to FIG. 17, a second connection component mounting cavity is defined between the surface of the fourth support part side plate 1722 facing the light outlet 11 and the outer side surface of the third support part side plate 1721. The second connection component 1723 includes a fourth connection post 1723*a* and a fifth connection post 1723*b*. The fourth connection post 1723*a* is disposed on the third support part side plate 1721 and/or the fourth support part side plate 1722, and is located in the second connection component mounting cavity, so that the thermal conductive structure 410 and the third holder 1253 are connected by inserting a fastener into the fourth connection post 1723*a* and the thermal conductive structure 410. The fifth connection post 1723*b* is disposed on the third support part side plate 1721 and/or the fourth support part side plate 1722, and is located in the second connection component mounting cavity, so that the housing 110 and the third holder 1253 are connected by inserting a fastener into the fifth connection post 1723*b* and the housing 110. An extension direction of the fourth connection post 1723*a* and an extension direction of the fifth connection post 1723*b* form an included angle. And/or, the second connection component 1723 includes a second engagement protrusion part1723*c*. The second engagement protrusion part1723*c* is disposed on the third support part side plate 1721 and/or the fourth support part side plate 1722, and is located in the second connection component mounting cavity for engagement with the thermal conductive structure 410. In this way, the above arrangement allows for more flexible setting in the position of the second connection post 1713*a* and/or the third connection post 1713*b*, to meet different user experiences and working conditions, and improves the processing flexibility. In addition, the third holder 1253 is detachably connected with the thermal conductive structure 410 and the housing 110, which is convenient to disassemble and assemble the skin treatment apparatus, thereby reducing the difficulty of disassembly and assembly.

In some embodiments, the fourth connection post 1723*a* is disposed on the third support part side plate 1721, so that the thermal conductive structure 410 and the third holder 1253 are connect by inserting a fastener into the fourth connection post 1723*a* and the thermal conductive structure 410. The fifth connection post 1723*b* is disposed on the fourth support part side plate 1722, so that the housing 110 and the third holder 1253 are connect by inserting a fastener into the fifth connection post 1723*b* and the housing 110. The second engagement protrusion part 1723*c* is disposed on the fourth support part side plate 1722. In this way, the positions of the fourth connection post 1723*a*, the fifth connection post 1723*b*, and the second engagement protrusion part1723*c* make it easier for a worker to disassemble and assemble the third holder 1253, the thermal conductive structure 410 and the housing 110, thereby reducing the difficulty of disassembly and assembly.

It should be noted that the position of the fourth connection post 1723*a* is not limited thereto, and may be adjusted according to working conditions and use requirements. Optionally, the fourth connection post 1723*a* is disposed on the fourth support part side plate 1722. Optionally, the fourth connection post 1723*a* is disposed on the third support part side plate 1721 and the fourth support part side plate 1722.

It should be noted that the position of the fifth connection post 1723B is not limited thereto, and may be adjusted according to working conditions and use requirements. Optionally, the fifth connection post 1723*b* is disposed on the third support part side plate 1721. Optionally, the fifth connection post 1723*b* is disposed on the third support part side plate 1721 and the fourth support part side plate 1722.

Optionally, the second connection component 1723 further includes a second connection block 1713*e*. The second connection block 1713*e* is disposed on the third support part side plate 1721 and the fourth support part side plate 1722, and is located in the second connection component mounting cavity. The fourth connection post 1723*a* is disposed on the third support part side plate 1721 and the surface of the second connection block 1713*e* away from the fourth support part side plate 1722. The fifth connection post 1723*b* is disposed on the fourth support part side plate 1722 and the surface of the second connection block 1713*e* away from the third support part side plate 1721. In this way, the fourth connection post 1723*a* and the fifth connection post 1723*b* are disposed in the second connection component mounting cavity by the second connection block 1713*e*, which enhances the structural strength of the second connection component 1723 and thereby prolonging the service life of the first connection support part 171.

Optionally, the surface of the third support part side plate 1721 facing the cold compress component 300 is provided with a first stop protrusion 1721*a*, which is disposed close to the light outlet 11; and/or, the surface of the first support part side plate 1711 facing the cold compress component 300 is provided with a second stop protrusion, which is disposed close to the light outlet 11. In this way, the first stop protrusion 1721*a* can limit the light transmitting member 310 so as to fix the light transmitting member 310 at a preset position, thereby preventing the light transmitting member 310 from shaking or moving and affecting the light transmission stability; and/or, the second stop protrusion can limit the light transmitting member 310 so as to fix the light transmitting member 310 at a preset position, thereby preventing the light transmitting member 310 from shaking or moving and affecting the light transmitting stability.

It should be noted that the description of "the third holder 1253 includes the second mounting plate 1253*a*, and the first connection support part 171 and the second connection support part 172 extending toward the second holder 1252, and two ends of the second mounting plate 1253*a* are connected to the first connection support part 171 and the second connection support part 172. The first connection support part 171 includes the first support part side plate 1711, the second support part side plate 1712, the first connection component 1713 and the first extension plate 1714. The second connection support part 172 includes the third support part side plate 1721, the fourth support part side plate 1722, the second connection component 1723 and the second extension plate 1724" is only an exemplary structural division of the third holder 1253. In other embodiments, the structure of the third holder 1253 may be divided in other form. For example, the structure including the second mounting plate 1253*a*, the first support part side plate 1711, the second support part side plate 1712, the third support part side plate 1721 and the fourth branch side plate 1722 is called a body part, and the body part is formed with the third mounting cavity 1251 and the mounting hole. The first extension plate 1714 is defined as the first connection support part 1714, and the second extension plate 1724 is defined as the second connection support part 1724. In other words, the third holder 1253 may include the body part and the first connection support part 1714 and the second connection support part 1724 that are connected to the body part. The first connection support part 1714 and the second connection support part 1724 are connected to the second holder 1252, and cover the two openings of the first mounting cavity 121.

As shown in FIG. 2 to FIG. 4, the light emitting component 200 includes the light emitting member 210 and the filter 220. The skin treatment apparatus further includes a phototherapy lamp 900. The housing component 100 further includes a fourth holder 191 and a fifth holder 192. The fourth holder 191 is connected to the third holder 1253 and the second holder 1252, and is located on the side of the third holder 1253 away from the thermal conductive structure 410. The fourth holder 191 is defined with a fourth mounting cavity 1911 and a fifth mounting cavity 1912. The phototherapy lamp 900 is disposed in the fourth mounting cavity 1911. The fourth mounting cavity 1911 is located between the light outlet 11 and the fifth mounting cavity 1912. The fifth holder is disposed in the fifth mounting cavity 1912, and is located between the light emitting member 210 and the cold compress component 300. The filter 220 is disposed on the fifth holder. The fourth holder 191 is configured to mount the phototherapy lamp 900, and support the second holder 1252 and the third holder 1253. This makes the structure of the housing component 100 more compact, thus improving the utilization rate of the inner space of the housing 110. The fifth holder is configured to mount the filter 220 so as to fix the filter 220 at a preset position, thereby preventing it from moving or shifting in the housing 110 and affecting its normal use.

As shown in FIG. 15 to FIG. 17, the first connection component 1713 further includes a sixth connection post 1713*f*, and the sixth connection post 1713*f* is disposed on the surface of the first connection block 1713*d* facing the fourth holder 191, so that a fastener is inserted into the sixth connection post 1713*f* and the fourth holder 191; and/or, the second connection component 1723 further includes a seventh connection post 1713*g*, and the seventh connection post 1713*g* is disposed on the surface of the second connection block 1713*e* facing the fourth holder 191, so that a fastener is inserted into the seventh connection post 1713*g* and the fourth holder 191. In this way, the first connection component 1713 is connected to the fourth holder 191 by the sixth connection post 1713*f* and the seventh connection post 1713*g*, which makes it easier and simpler to disassemble and assemble the first connection component 1713 and the fourth holder 191, thereby reducing the difficulty of disassembly and assembly.

Optionally, the sixth connecting post 1713*f* is a stud.

Optionally, the seventh connecting post 1713*g* is a stud.

Figure 18:
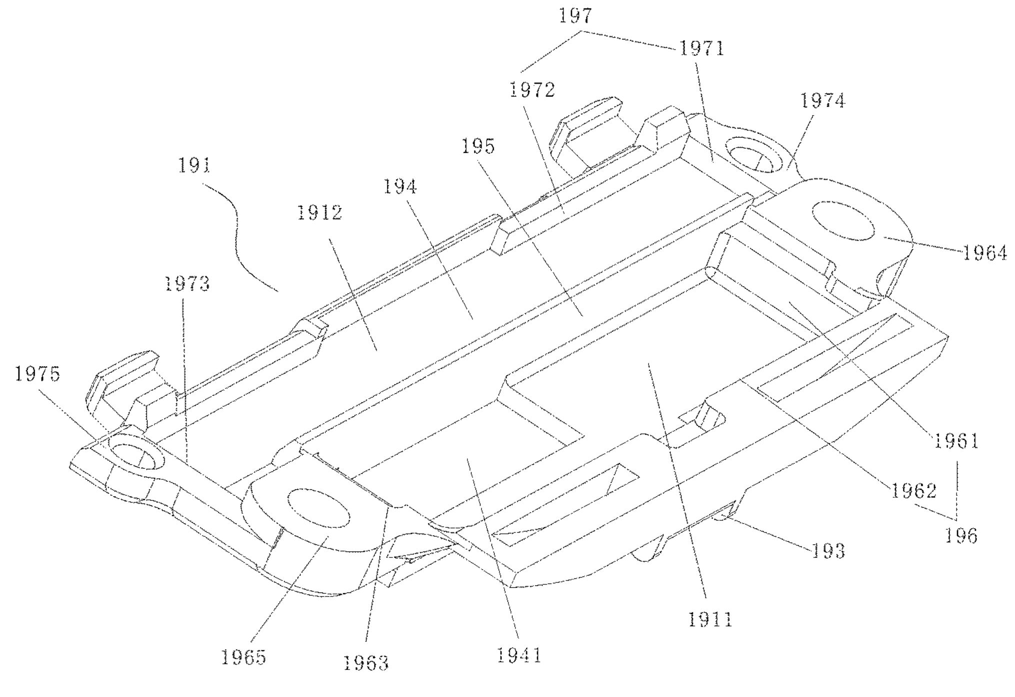
FIG. 18 is a perspective view of a fourth holder of the holder component in FIG. 4.
Figure 19:
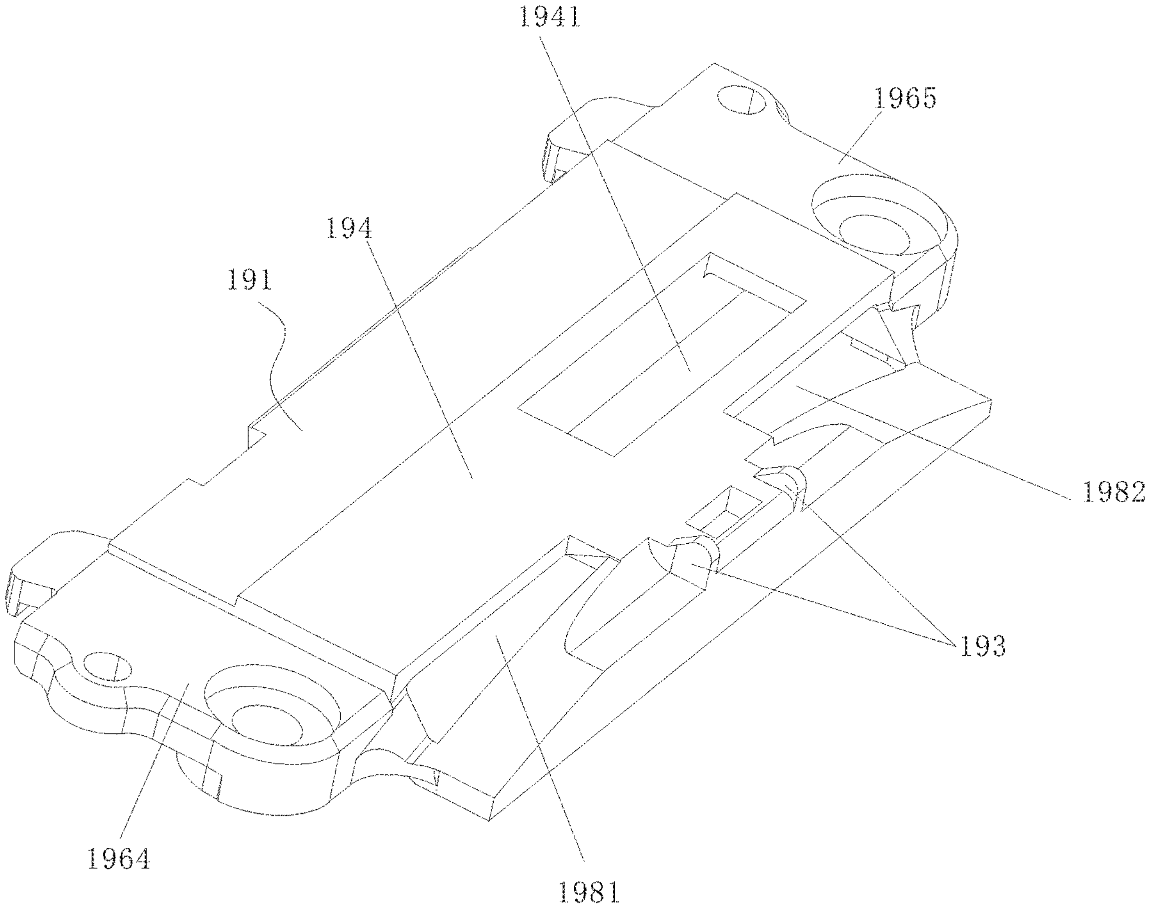
FIG. 19 is a perspective view of the fourth holder in FIG. 18 from another perspective.

As shown in FIG. 2, FIG. 18 and FIG. 19, the skin treatment apparatus further includes a Hall sensor 910. The side of the fourth holder 191 away from the third holder 1253 is provided with two third engagement protrusion parts 193 facing each other. A limiting space is defined between the two engagement protrusion parts 193, and at least part of the Hall sensor 910 is located in the limiting space. In this way, the Hall sensor 910 is mounted and limited in the limiting space to prevent itself from moving or shifting and affecting its normal use. In addition, the above arrangement makes the layout of the Hall sensor 910 and the fourth holder 191 in the housing 110 more reasonable and compact, thereby improving the utilization rate of the internal space of the housing 110.

As shown in FIG. 18 and FIG. 19, the fourth holder 191 includes a third mounting plate 194, a baffle plate 195, a first enclosure plate 196, and a second enclosure plate 197. The baffle plate 195 is disposed on the third mounting plate 194. The first enclosure plate 196 is disposed on the third mounting plate 194 and connected to the baffle plate 195. The first enclosure plate 196, the plate surface of the baffle plate 195 facing the light outlet 11, and at least a part of the third mounting plate 194 enclose to form a fourth mounting cavity 1911. The second enclosure plate 197 is disposed on the third mounting plate 194 and connected to the baffle plate 195. The second enclosure plate 197, the plate surface of the baffle plate 195 away from the light outlet 11, and at least another part of the third mounting plate 194 enclose to form a fifth mounting cavity 1912. In this way, with the arrangement in which the first enclosure plate 196, the baffle plate 195, and at least a part of the third mounting plate 194 enclose to form the fourth mounting cavity 1911 that is in the form of a first recessed part, and the phototherapy lamp 900 is mounted in the first recessed part, a structural interference between the phototherapy lamp 900 and the light transmitting member 310 can be prevented, thereby preventing affecting normal light transmission of the light transmitting member 310. In addition, the fifth mounting cavity 1912 is in the form of a second recessed part, and the filter 220 is mounted in the second recessed part to support and limit the filter 220, which further prevents the filter 220 from moving or shifting in the housing 110 and affecting its filtering reliability.

As shown in FIG. 18 and FIG. 19, the first enclosure plate 196 includes a first side plate section 1961, a first connection plate 1962, and a second side plate section 1963. The first side plate section 1961 and the second side plate section 1963 face each other, and are both connected to the baffle plate 195. The surface of the first connection plate 1962 facing the cold compress component 300 is provided with a first engagement recessed part communicated with the fourth mounting cavity 1911. At least part of the phototherapy lamp 900 extends into the first engagement recessed part and is engaged with the first engagement recessed part. Two third engagement protrusion parts 193 are disposed on the surface of the first connection plate 1962 away from the cold compress component 300. In this way, the first enclosure plate 196 has a simple structure which is easy to process and implement, thereby reducing the processing cost and processing difficulty of the first enclosure plate 196. Moreover, the positions of the third engagement protrusion parts 193 are more reasonable, and they do not interfere with the phototherapy lamp 900.

As shown in FIG. 18 and FIG. 19, a first support plate 1964 is disposed on an outer side surface of the first side plate section 1961, the first support plate 1964 is configured to support the sixth connection post 1713*f* and is defined with a first passing hole for a fastener to pass through; and/or, a second support plate 1965 is disposed on an outer side surface of the second side plate section 1963, the second support plate 1965 is configured to support the seventh connection post 1713*g* and is defined with a second passing hole for a fastener to pass through. In this way, the sixth connection post 1713*f* and the seventh connection post 1713*g* are spaced from the phototherapy lamp 900 with no structural interference, thus is convenient for disassembly and assembly.

Optionally, the third mounting plate 194 located in the fourth mounting cavity 1911 is defined with a ventilation hole 1941; and/or, each third engagement protrusion part 193 extends toward the light outlet 11 and then extends to the side edge of the first connection plate 1962 facing the light outlet 11. The ventilation hole 1941 helps to cool the phototherapy lamp 900 so as to prevent the surface temperature of the phototherapy lamp 900 from being too high to affect its service life. In addition, the ventilation hole 1941 can play a role in weight reduction, thereby realizing a lightweight design of the fourth holder 191.

As shown in FIG. 18 and FIG. 19, a joint of the third mounting plate 194, the first side plate section 1961 and the first connection plate 1962 is defined with a first through hole 1981 for at least part of the phototherapy lamp 900 to pass through; and/or, a joint of the third mounting plate 194, the second side plate section 1963 and the first connection plate 1962 is defined a second through hole 1982 for at least part of the phototherapy lamp 900 to pass through. In this way, the first through hole 1981 and/or the second through hole 1982 can position the phototherapy lamp 900 so as to prevent the phototherapy lamp 900 from moving or shifting in the fourth holder 191 and affecting its mounting stability.

As shown in FIG. 18 and FIG. 19, the second enclosure plate 197 includes a third side plate section 1971, a second connection plate 1972, and a fourth side plate section 1973. The third side plate section 1971 and the fourth side plate section 1973 face each other, and are both connected to the baffle plate 195. The side edge of the first connection plate 1962 away from the light outlet 11 is provided with a fourth engagement protrusion part that is engaged with the second holder 1252. The second enclosure plate 197 has a simple structure which is easy to process and implement, thereby reducing the processing cost and processing difficulty of the second enclosure plate 197. Moreover, the above arrangement makes it easier to assemble and dissemble the fourth holder 191 with the second holder 1252, thereby reducing the difficulty of assembly and disassembly; also, the engagement position between the fourth holder 191 and the second holder 1252 has no structural interference with the filter 220, which facilitates disassembly and assembly.

As shown in FIG. 18 and FIG. 19, a third support plate 1974 is disposed on an outer side surface of the third side plate section 1971, and the third support plate 1974 is configured to support the third holder 1253 and is defined with a second engagement recessed part that is engaged with the third holder 1253; and/or, a fourth support plate 1975 is disposed on an outer side of the fourth side plate section 1973, and the fourth support plate 1975 is configured to support the third holder 1253 and is defined with a third engagement recessed part that is engaged with the third holder 1253. The second engagement recessed part and/or the third engagement recessed part are configured to be engaged with the third holder 1253, so as to realize a detachable connection between the fourth holder 191 and the third holder 1253, thereby being convenient for a user to disassemble and assemble the skin treatment apparatus.

Optionally, the thermal conductive structure 410 is a vapor chamber or a heat pipe. The heat dissipation sheet component 420 and the light emitting component 200 are located on two opposite sides of the thermal conductive structure 410. This allows for a more flexible selection in the structure of the thermal conductive structure 410, to meet different user requirements and working conditions, and improve the processing flexibility. In addition, the heat dissipation sheet component 420 and the light emitting component 200 are stacked in the thickness direction of the housing 110, to shorten the overall length of the thermal conductive structure 410, thereby improving the heat dissipation performance of the heat dissipation component 400.

In some embodiments, the thermal conductive structure 410 is a vapor chamber, which extends along a front-rear direction of the housing 110.

Optionally, the thermal conductive structure 410 further includes a third thermal conductive section. The third thermal conductive section is connected to the end of the second thermal conductive section 412 away from the first thermal conductive section 411. The third thermal conductive section protrudes from the light emitting component 200 in a direction opposite to the light output direction of the light emitting component 200. The heat dissipation sheet component 420 is further disposed on the third thermal conductive section. In an embodiment, the third thermal conductive section is a condensation section.

The above arrangement ensures that an orthographic projection of the light emitting component 200 on the thermal conductive structure 410 is within the thermal conductive structure 410, and the heat dissipation sheet component 420 has a relatively large heat dissipation area, to fully and/or quickly dissipate heat from the cold coating component 300.

In the embodiments, the cool compress component 300 includes the light transmitting member 310 and the cooling plate 800. The light transmitting member 310 is disposed on the housing component 100. The light transmitting member 310 is located on the side of the light emitting component 200 facing the light outlet 11, and is disposed corresponding to the light outlet 11. The light transmitting member 310 is configured to transmit the light generated by the light emitting component 200 out of the light outlet 11. The cooling plate 800 includes a cooling surface and a heat dissipation surface. The cooling surface is thermally connected to the light transmitting member 310, and the heat dissipation surface is thermally connected to the first thermal conductive section 411. The first thermal conductive section 411 cools the light transmitting member 310 by the cooling plate 800, so as to prevent the surface temperature of the light transmitting member 310 from being too high to burn a user.

Optionally, there is one cooling plate 800. Alternatively, there are two cooling plates 800, and the two cooling plates 800 are connected to two sides of the light transmitting member 310. The cooling plate 800 may be a semiconductor cooling plate, which includes a cooling surface and a heat dissipation surface facing each other. The cooling surface is in contact with a side surface of the light transmitting member 300.

Optionally, a length direction the housing component 100 and the light output direction of the light emitting component 200 form an included angle. The included angle is greater than or equal to 3 degrees and less than or equal to 55 degrees, such as, 6 degrees, 8 degrees, 10 degrees, 12 degrees, 14 degrees, 16 degrees, 18 degrees, 20 degrees, 22 degrees, 24 degrees, 26 degrees, 28 degrees, 30 degrees, 32 degrees, 34 degrees, 36 degrees, 38 degrees, 40 degrees, 42 degrees, 44 degrees, 46 degrees, 48 degrees, 50 degrees, 52 degrees, 54 degrees, or 55 degrees.

Preferably, the included angle is greater than or equal to 6 degrees and less than or equal to 36 degrees. In this way, when a user holds the skin treatment apparatus for use, the housing 110 is tilted with respect to the skin to be treated, thereby improving the user experience. For example, in a process of facial hair removal (such as beard removal), when the attachment surface is in attached to the human face, the housing 110 may be tilted downward to reduce user arm fatigue. For another example, in a process of lower-leg hair removal, when the attachment surface is attached to the skin of the lower leg, the housing 110 may be tilted with respect to the skin of the lower leg instead of being pressed perpendicularity against the skin of the lower leg, which helps to reduce user arm fatigue.

As shown in FIG. 12, in the second embodiment of the holder component 120, different from the first embodiment of the holder component 120, no third air vent is formed, but a heat dissipation cavity 105 is formed. The heat dissipation cavity 105 is located inside the holder component 120, and is communicated with the at least one air vent part 12. In this way, the cavity body in the holder component 120 forms the heat dissipation cavity 105, and the air in the heat dissipation cavity 105 is blown out through the air vent part 12 after exchanging heat with the thermal conductive structure 410. With such arrangement, the heat dissipation efficiency is also improved.

Illustratively, the first support part 131 includes a first support plate 1311 and an auxiliary support plate 1312 disposed laterally. One side of the auxiliary support plate 1312 is connected to the side of the first support plate 1311 away from the heat dissipation sheet component 420, and the other side of the auxiliary support plate 1312 abuts against the thermal conductive structure 410. The area enclosed by the auxiliary support plate 1312 and the first support plate 1311 forms the heat dissipation cavity 105. The heat dissipation cavity 105 is communicated with the first ventilation flow channel 151. The heat dissipation cavity 105 is formed by the auxiliary support plate 1312 and the first support plate 1311, and the air entering the heat dissipation cavity 105 from the mounting cavity 101 enters the first ventilation flow channel 151, and then is blow out through the air vent part 12.

In the second embodiment, the first support part 131 further includes a drainage plate 1313. One end of the drainage plate 1313 is connected to at least one of the first support plate 1311 and the auxiliary support plate 1312, and the other end of the drainage plate 1313 is connected to the first outer support part 141. A drainage port is defined between the drainage plate 1313 and the first outer support part 141, and the heat dissipation cavity 105 is communicated with the first ventilation flow channel 151 through the drainage port. With this arrangement, the air in the heat dissipation cavity 105 is guided, such that the air in the heat dissipation cavity 105 after heat exchange is blown out through the first ventilation flow channel 151 to take away heat, thereby realizing heat dissipation.

The lateral end portions of the first support plate 1311 and the auxiliary support plate 1312 extend to the second side support part 134, so that the heat dissipation cavity 105 is not communicated with the second ventilation flow channel 152. That is, in this embodiment, the air in the heat dissipation cavity 105 can be blown out through the first ventilation flow channel 151. Of course, in other embodiments, the heat dissipation cavity 105 may be communicated with the second ventilation flow channel 152, and the air may be blown out through the second ventilation flow channel 152.

As shown in FIG. 20 to FIG. 31, the fan holder 700 includes a support base 710. The main control board 600 is mounted on the fan holder 700 and/or the housing 110. The main control board 600 is located on one side of the support base 710, and the fan 500 is located on the side of the support base 710 away from the main control board 600. In this solution, the fan 500 and the main control board 600 are disposed on two sides of the support base 710 of the fan support 700. This prevents the fan 500 from occupying the space of the main control board 600, such that the main control board 600 has a relatively large area to arrange elements, which is more convenient for element arrangement according to needs. Since the fan 500 does not cover the surface of the main control board 600 and the elements on the main control board 600, this area can be better ventilated to dissipate heat. Moreover, the arrangement in which the main control board 600 and the fan 500 are mounted on two sides of the support base 710 is advantageous for the support base 710 to support and mount the main control board 600 and the fan 500, which simplifies the structure and is convenient for assembly.

The first side plate 112 is located on the side of the main control board 600 away from the support base 710, the second side plate 113 is located on the side of the support base 710 away from the first side plate 112, and the support base 710 is spaced from the first side plate 112 and the second side plate 113. The cavity enclosed by the first side plate 112 and the second side plate 113 is configured to mount components such as the main control board 600, the fan holder 700 and the fan 500. The first side plate 112 and the second side plate 113 can protect these components. The support base 710 is spaced from the first side plate 112 and the second side plate 113 to avoid interference during assembly.

Figure 25:
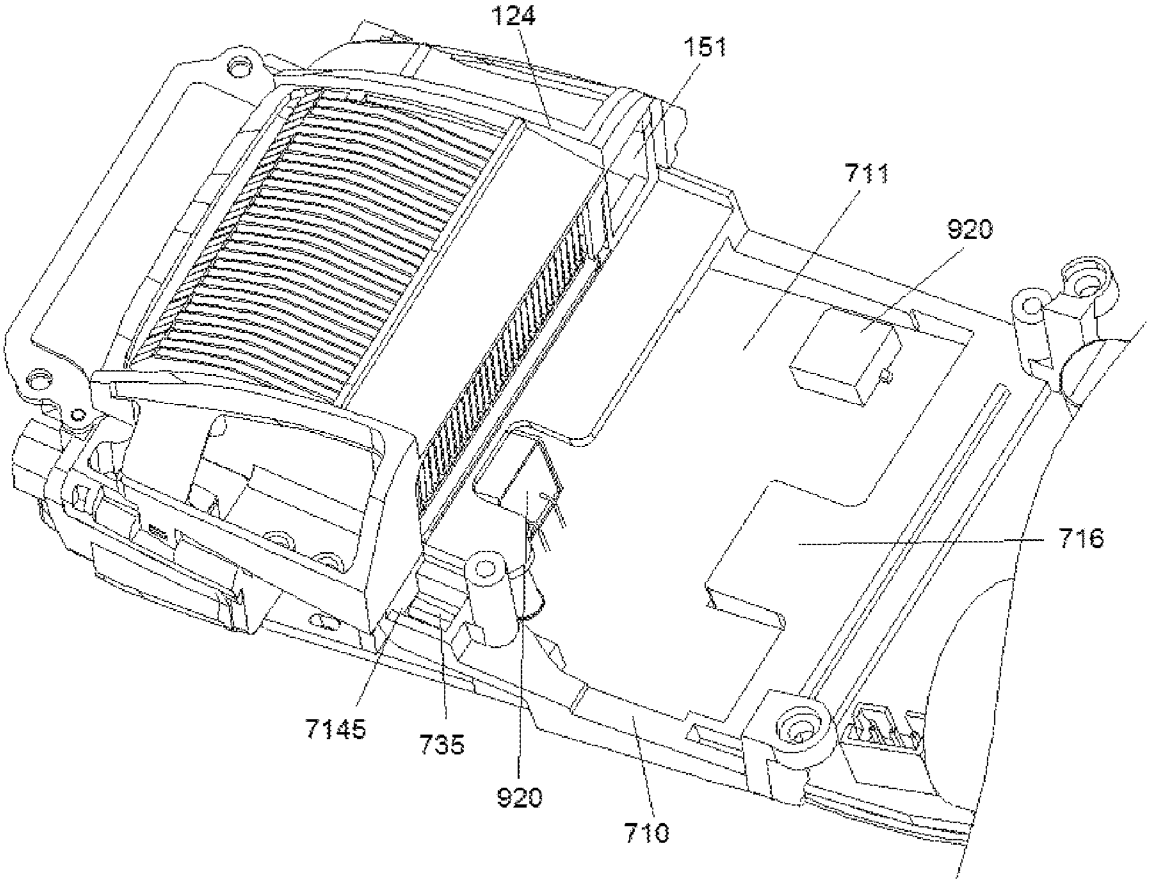
FIG. 25 is a structural schematic diagram of a portion of a skin treatment apparatus according to an embodiment of the present disclosure.

As shown in FIG. 25, an element 920 is mounted in the area between the main control and a first end. Since the area between the main control board 600 and the first end is relatively large, it is convenient to arrange the element 920 without interfering with other structures, and is also advantageous for the heat dissipation.

The support base 710 is defined with a hollow cavity 711. The hollow cavity 711 is located between the main control board 600 and the fan 500. With the arrangement of the hollow cavity 711, a large space is formed between the main control board 600 and the fan 500, which facilitates the arrangement of the element 920 and is advantageous to the flow of air. Moreover, the hollow cavity 711 helps to save materials and thus reducing the weight of the apparatus on the premise of ensuring the strength. In this embodiment, the element 920 is mounted in the area of the main control board 600 facing the hollow cavity 711.

As shown in FIG. 20 and FIG. 21, one end of the fan 500 is connected to the first end, and the other end of the fan 500 is connected to the second end. The fan 500 is inclined with respect to the main control board 600. The fan 500 is fixed by the first end and the second end of the support base 710, and is inclined with respect to the main control board 600, to avoid occupying too much space on the main control board 600. This realizes the avoidance of the middle area of the main control board 600, which is advantageous to arrange the element 920 on the main control board 600 and is beneficial for the heat dissipation of the main control board 600 and the element 920.

Illustratively, as shown in FIG. 20 to FIG. 31, the support base 710 includes a first base 712 disposed at the first end, a second base 713 disposed at the second end, and a first side base 714 and a second side base 715. The first side base 714 faces the second side base 715. One end of the first side base 714 and one end of the second side base 715 are connected to the first base 712, the other end of the first side base 714 and the other end of the second side base 715 are connected to the second base 713, so that the first base 712 is spaced apart from the main control board 600.

In this way, the first base 712 is spaced from the main control board 600, and the hollow area, namely the hollow cavity 711, enclosed by the first base 712, the second base 713, the first side base 714 and the second side base 715 is also spaced from the main control board 600, such that the main control board 600 has a large space on the side facing the fan 500, which facilitates the heat dissipation and the arrangement of the element 920. The first base 712 and the second base 713 are configured to support the fan 500.

The first base 712 includes a first base plate 7121. One end of the first base plate 7121 is connected to the first side base 714, the other end of the first base plate 7121 is connected to the second side base 715. The first base plate 7121 supports the fan 500. The first base plate 7121 has a plate-like structure, which increases the contact area with the fan 500. The connection is stable and reliable, and is easy to process.

Figure 29:
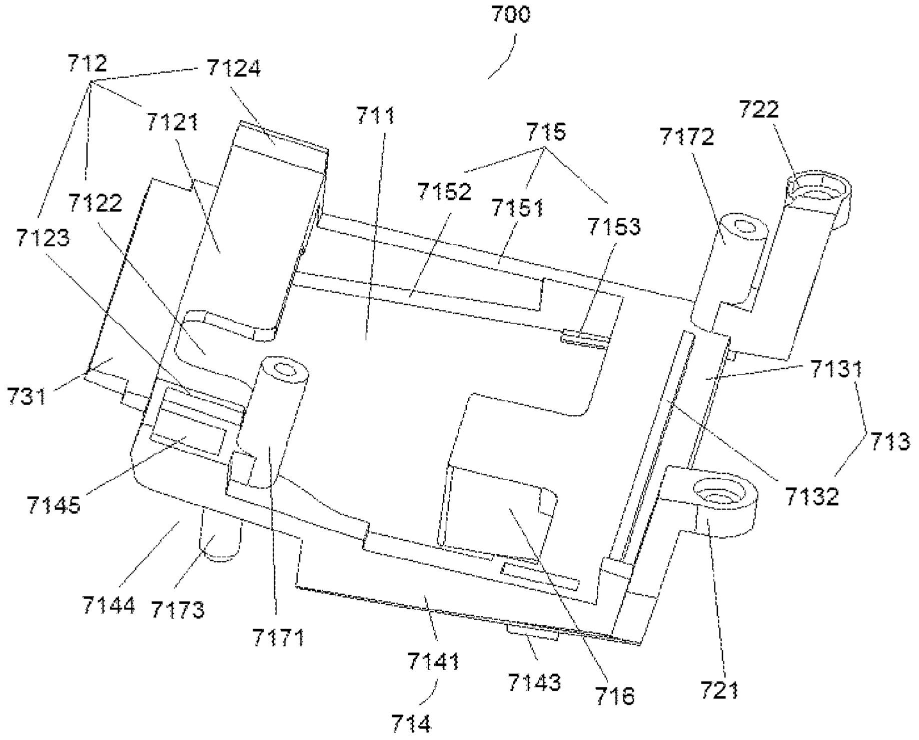
FIG. 29 is a schematic diagram of the support holder in FIG. 20 from a first perspective.

As shown in FIG. 25 and FIG. 29, the first base plate 7121 is defined with an avoidance notch 7122. An opening of the avoidance notch 7122 faces the second base 713. The avoidance notch 7122 avoids the element 920 mounted on the main control board 600. By providing the avoidance notch 7122, an interference between the first base plate 7121 and the element 920 mounted on the main control board 600 can be prevented. In this way, the element 920 having a relatively large height can be mounted at the avoidance notch 7122.

As shown in FIG. 29, the first base 712 further includes a first limiting flange 7123, the first limiting flange 7123 is located at the end of the first base plate 7121 close to the first side base 714, the first limiting flange 7123 protrudes from the side of the first base plate 7121 facing the fan 500, and the first limiting flange 7123 is in stop fit with the outer wall of the fan 500; and/or, the first base 712 further includes a second limiting rib 7124, the second limiting rib 7124 is located at the end of the first base plate 7121 close to the second side base 715, the second limiting rib 7124 protrudes from the side of the first base plate 7121 facing the fan 500, and the second limiting rib 7124 is in stop fit with the outer wall of the fan 500. The first limiting flange 7123 and the second limiting rib 7124 help to limit the fan 500 in the length direction of the first base plate 7121, which ensures the accurate mounting position of the fan 500, thereby avoiding the deviation in the position of the fan 500.

The second base 713 includes a second base plate 7131 and a support bar 7132. One end of the second base plate 7131 is connected to the first side base plate 714, and the other end of the second base plate 7131 is connected to the second side base plate 715. The support bar 7132 protrudes from the side of the second base plate 7131 facing the fan 500. The support bar 7132 is configured to support the fan 500. The second base plate 7131 is spaced from the fan 500. The fan 500 is supported by the second base plate 7131 and the support bar 7132, also the support bar 7132 is served as a reinforcing rib, which improves the structural strength of the second base plate 7131.

In the embodiments, the first side base 714 includes a first side body 7141. One end of the first side body 7141 is connected to the first base 712, and the other end of the first side body 7141 is connected to the second base 713. In the direction from the second end to the first end, a distance from the surface of the first side body 7141 facing away from the main control board 600 to the main control board 600 gradually increases. The change in the size of the first side body 7141 allows that the first base 712 is spaced from the main control board 600 and the fan 500 is inclinedly disposed.

Figure 26:
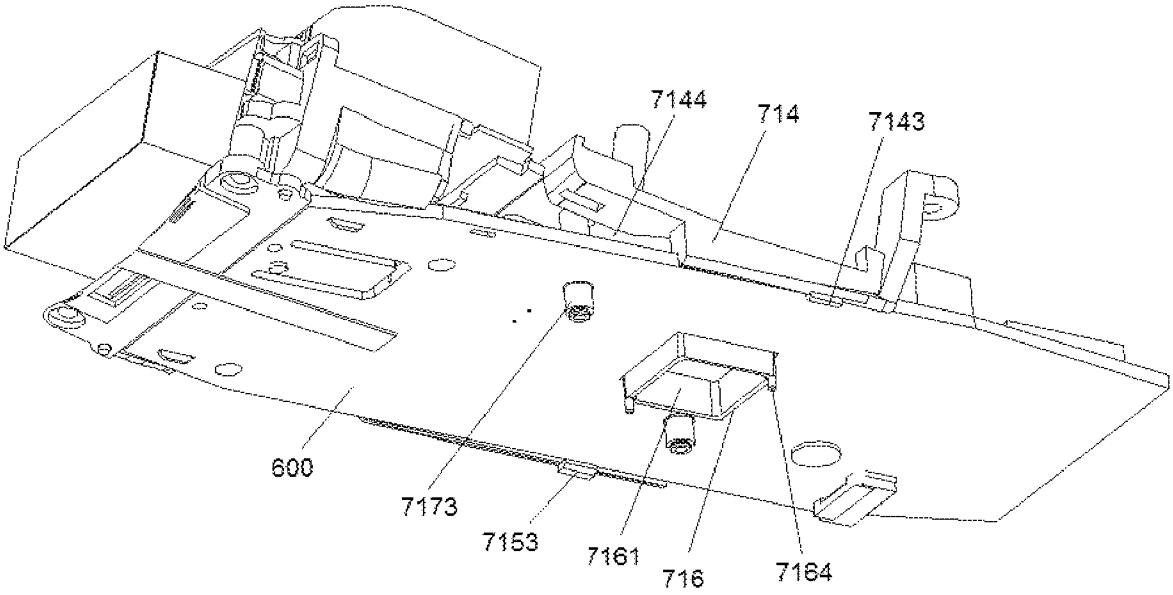
FIG. 26 is a schematic diagram of the skin treatment apparatus in FIG. 25 from another perspective.
Figure 27:
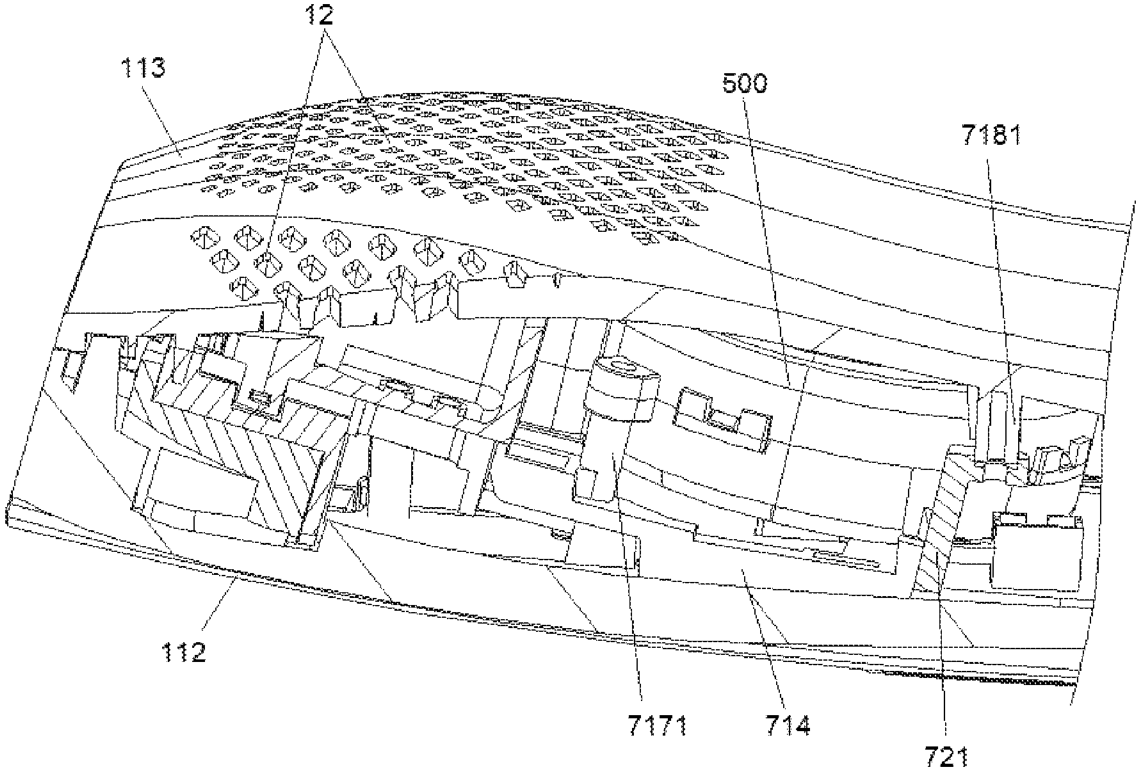
FIG. 27 is a sectional diagram of a joint of a second side plate and a support holder of the skin treatment apparatus in FIG. 20.
Figure 30:
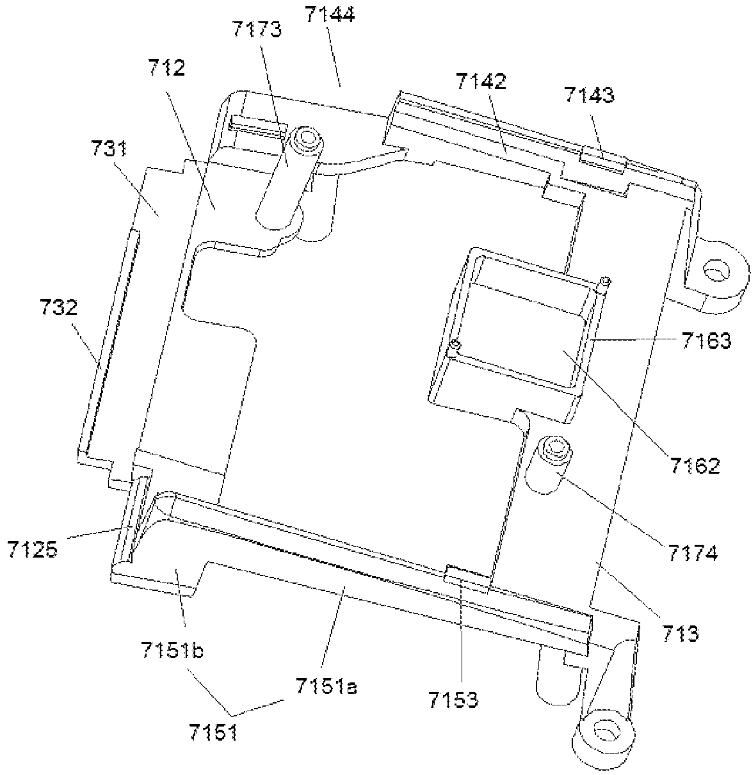
FIG. 30 is a schematic diagram of the support holder in FIG. 20 from a second perspective.

As shown in FIG. 26 and FIG. 30, the side of the first side body 7141 facing the main control board 600 is provided with a first limiting step 7142. The first limiting step 7142 is in limiting fit with the surface of the main control board 600 facing the fan 500 and the side surface of the main control board 600. By providing the first limiting step 7142, the first side body 7141 and the main control board 600 are limited to each other, thereby ensuring the accuracy of the assembly position.

Further, the first side base 714 further includes a first snap-fit element 7143. The first snap-fit element 7143 is located on the side of the first side body 7141 away from the fan 500, and is in snap-fit with the side of the main control board 600 away from the fan 500. In this way, the first side base 714 is connected to the main control board 600 by means of a snap-fit connection, which is convenient for operation and improves connection reliability.

In the embodiments, the second side base 715 includes a second side body 7151. One end of the second side body 7151 is connected to the first base 712, and the other end of the second side body 7151 is connected to the second base 713. In the direction from the second end to the first end, a distance from the surface of the second side body 7151 away from the main control board 600 to the main control board 600 gradually increases. The change in the size of the second side body 7151 allows that the first base 712 is spaced from the main control board 600 and the fan 500 is inclinedly disposed.

Illustratively, the second side body 7151 includes an inclined body 7151*a* and a protrusion body 7151*b*. One end of the inclined body 715*la* is connected to the second base 713. The surface of the inclined body 7151*a* away from the main control board 600 is an inclined surface. The protrusion body 7151*b* is disposed at the other end of the inclined body 7151*a*, and protrudes from the inclined surface of the inclined body 7151*a*. The protrusion body 7151*b* is connected to one end of the first base 712. The inclined body 7151*a* is spaced from the fan 500. The surface of the inclined body 7151*a* away from the main control board 600 is an inclined surface, which increases the distance between the first base 712 and the main control board 600. The protrusion body 7151*b* protrudes from the inclined surface of the inclined body 7151*a* and is connected to one end of the first base 712, which further increases the distance between the first base 712 and the main control board 600, thereby realizing the avoidance of the main control board 600.

As shown in FIG. 26 and FIG. 29 to FIG. 31, the side of the second side body 7151 facing the main control board 600 is provided with a second limiting step 7152. The second limiting step 7152 is in limiting fit with the surface of the main control board 600 facing the fan 500 and the side surface of the main control board 600. By providing the second limiting step 7152, the second side body 7151 and the main control board 600 are limited to each other, thereby ensuring the accuracy of the assembly position.

Further, the second side base 715 further includes a second snap-fit element 7153. The second snap-fit element 7153 is located on the side of the second side body 7151 away from the fan 500, and is engaged with the side of the main control board 600 away from the fan 500. In this way, the second side base 715 is connected to the main control board 600 by means of a snap-fit connection, which is convenient for operation and improves connection reliability.

As shown in FIG. 23 and FIG. 26, the skin treatment apparatus further includes a control board 930. The control board 930 is located on the side of the main control board 600 away from the fan 500. A chip is installed on the control board 930. The fan holder 700 further includes a protection part 716. The protection part 716 is connected to the second base 713. The protection part 716 passes through the passing hole provided in the main control board 600. The protection part 716 is defined with a protection groove 7161, whose opening faces the control board 930. The chip is located within the protection groove 7161, such that the chip can be protected by the protection part 716. In addition, for a chip generating radiation, the protection part can prevent or reduce the radiation impact of the chip on other structures outside the protection part 716 as well as user.

Figure 31:
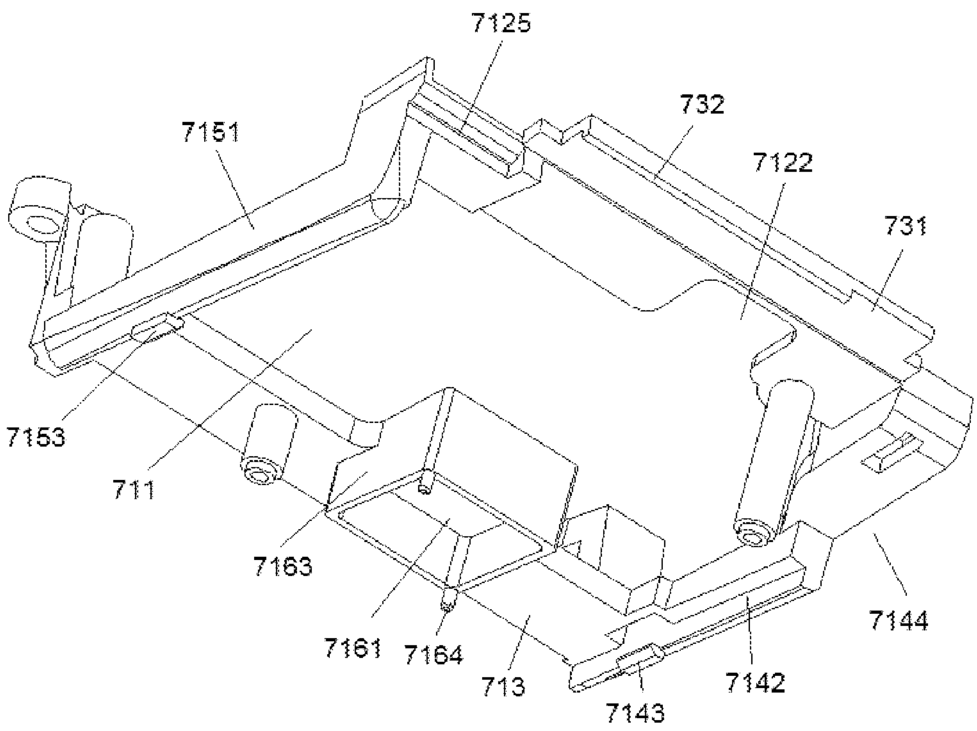
FIG. 31 is a schematic diagram of the support holder in FIG. 20 from a third perspective.

As shown in FIG. 29 to FIG. 31, the protection part 716 includes a protection bottom wall 7162 and a protection peripheral wall 7163. The protection bottom wall 7162 is connected to the side of the second base 713 facing the first base 712. A part of the protection peripheral wall 7163 is connected to the side of the protection bottom wall 7162 facing the main control board 600, and the other part of the protection peripheral wall 7163 is connected to the side of the second base 713 facing the main control board 600. The protection bottom wall 7162 and the protection peripheral wall 7163 are both connected to the second base 713, which ensures the structural strength of the protection part 716.

The control board 930 is defined with a positioning hole, and the side of the protection part 716 facing the main control board 600 is provided with a positioning post 7164. The positioning post 7164 passes through the positioning hole. By the cooperation of the positioning post 7164 and the positioning hole, mutual positioning and limiting of the control board 930 and the protection part 716 are realized, ensuring that the chip is located in the protection groove 7161 after the assembly is completed. A plurality of positioning posts 7164 and a plurality of positioning holes may be provided, and each positioning post 7164 corresponds to one positioning hole.

As shown in FIG. 21, FIG. 24 to FIG. 31, the fan holder 700 further includes a first holder connection post 7171 and a second holder connection post 7172. The first holder connection post 7171 and the second holder connection post 7172 are distributed on two of the first base 712, the second base 713, the first side base 714 and the second side base 715. The first holder connection posts 7171 are located at two diagonal positions of the support base 710. The first holder connection post 7171 and the second holder connection post 7172 are fixedly connected to two lugs on the fan 500. In this way, the first holder connection post 7171 and the second holder connection post 7172 are cooperated with the two lugs to realize a fixed connection between the fan 500 and the fan holder 700. Moreover, the first holder connection posts 7171 are distributed at the two diagonal positions of the support base 710 to ensure the connection reliability.

In some embodiments, the fan holder 700 further includes a third holder connection post 7173 and a fourth holder connection post 7174. The third holder connection post 7173 is located on the first base 712, and the fourth holder connection post 7174 is located on the second base 713. The third holder connection post 7173 passes through the main control board 600 and is connected to the control board 930 by a fastener, and the fourth holder connection post 7174 passes through the main control board 600 and is connected to the control board 930 by a fastener. By the third holder connection post 7173 and the fourth holder connection post 7174, the fan holder 700 is connected to the control board 930, and the position of the control board 930 relative to the main control board 600 is limited.

Figure 22:
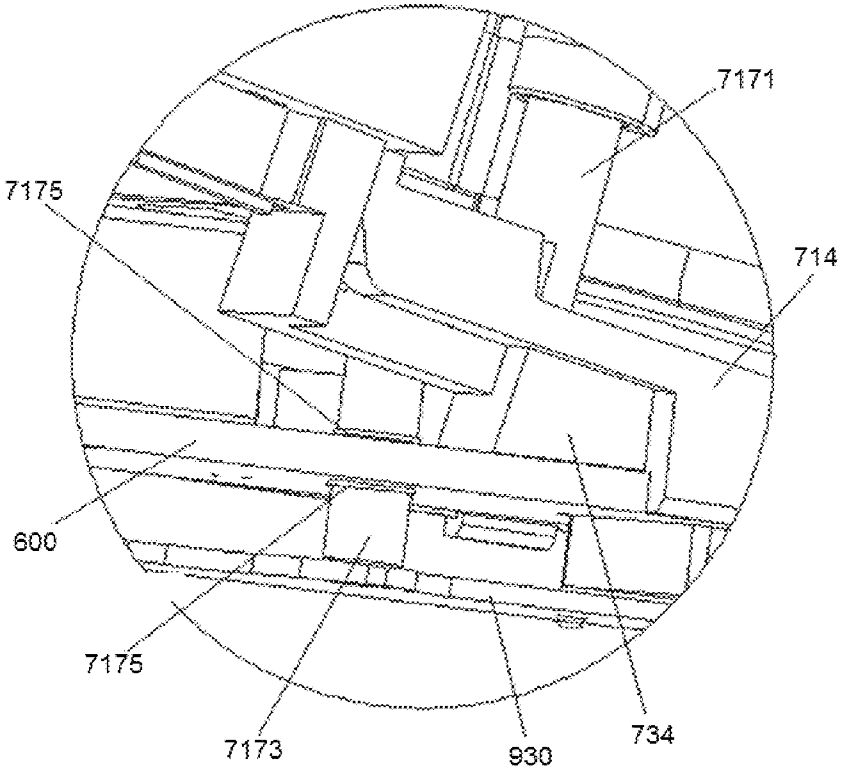
FIG. 22 is an enlarged view of portion A of the skin treatment apparatus in FIG. 21.

As shown in FIG. 21 and FIG. 22, the third holder connection post 7173 and/or the fourth holder connection post 7174 is provided with two limiting rings 7175. One limiting ring 7175 is located on one side of the main control board 600, and the other limiting ring 7175 is located on the other side of the main control board 600. The two limiting rings 7175 are in limiting fit with the two sides of the main control board 600. The two limit rings 7175 limit the position of the third holder connection post 7173 or the position of the fourth holder connection post 7174 relative to the main control board 600 in an axial direction, so as to limit the position of the fan holder 700 relative to the main control board 600, thereby ensuring the assembly precision and supporting the main control board 600.

As shown in FIG. 24 to FIG. 29, the side of the second side plate 113 facing the fan holder 700 is provided with a fifth holder connection post 7181 and a sixth holder connection post 7182 spaced apart. The fifth holder connection post 7181 is located on one side of the fan 500, and the sixth holder connection post 7182 is located on the other side of the fan 500. The fan holder 700 further includes a first connection seat 721 and a second connection seat 722. The first connection seat 721 and the second connection seat 722 are located at the second end of the support base 710 away from the rear part of the housing 110. The first connection seat 721 is connected to the fifth holder connection post 7181 through a fastener, and the second connection seat 722 is connected to the sixth holder connection post 7182 through a fastener. The above arrangement realizes a fixed connection between the fan holder 700 and the second side plate 113. In addition, the fan holder 700 is connected to multiple components, realizing the connection of multiple components within the skin treatment apparatus.

Figure 24:
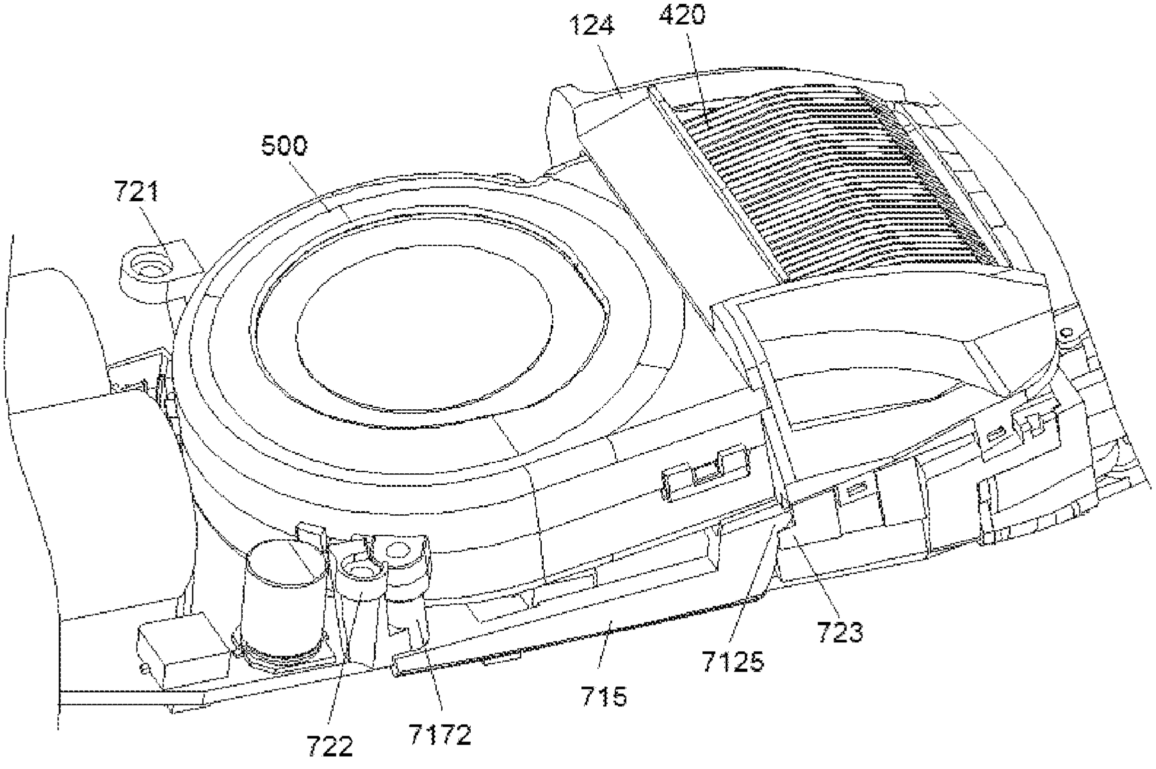
FIG. 24 is a schematic diagram of the skin treatment apparatus in FIG. 21 from another perspective.
Figure 28:
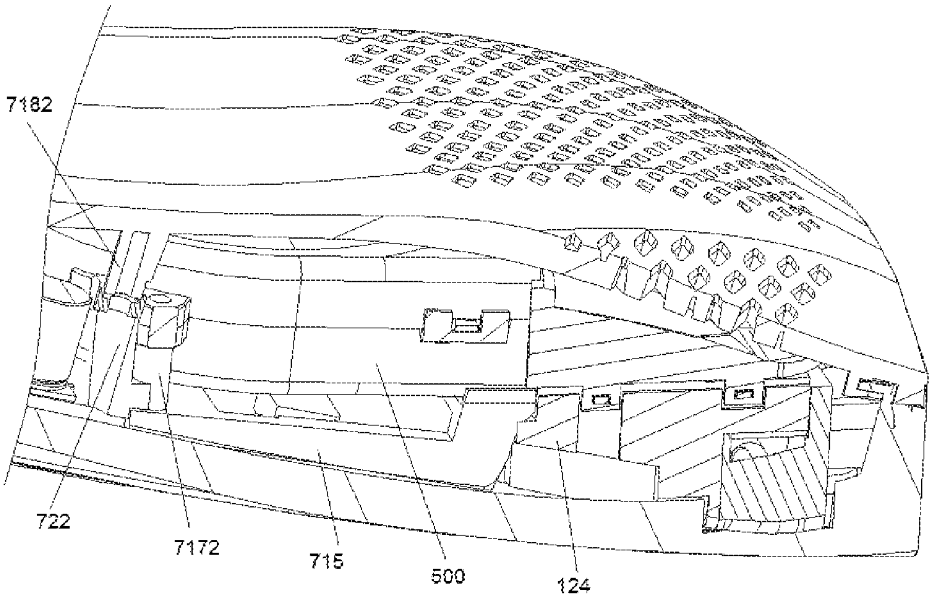
FIG. 28 is a sectional diagram of another joint of the second side plate and the support holder of the skin treatment apparatus in FIG. 20.

As shown in FIG. 24, FIG. 28, and FIG. 31, the side of the first base 712 facing the main control board 600 and the end close to the second side base 715 is provided with a third limiting step 7125, the end of the heat dissipation sheet holder 124 facing the fan 500 is provided with a fourth limiting step 723. The third limiting step 7125 is in limiting fit with the fourth limiting step 723. By the cooperation of the third limiting step 7125 and the fourth limiting step 723, the heat dissipation sheet holder 124 and the fan holder 700 are limited to each other in the length direction and the thickness direction of the skin treatment apparatus.

As shown in FIG. 23 and FIG. 31, the fan holder 700 further includes an extension plate 731. The extension plate 731 is disposed on the side of the first base 712 away from the second base 713. The extension plate 731 is located between a light source holder 720 and the heat dissipation component 400. The extension plate 731 supports the heat dissipation component 400. In this way, the heat dissipation component 400 is supported by the extension plate 731. The heat dissipation component 400 includes the thermal conductive structure and the heat dissipation sheet component 420. The extension plate 731 supports the thermal conductive structure.

Optionally, the extension plate 731 is overlapped with the light emitting side holder 125. The end of the extension plate 731 away from the first base 712 is provided with a limiting bar 732, and the limiting bar 732 protrudes from the side of the extension plate 731 facing the main control board 600. The light emitting side holder 125 is defined with a hollow hole 733. The limiting bar 732 extends into the hollow hole 733 and is in limiting fit with an inner wall of the hollow hole 733. In this way, mutual support and limitation of the light emitting side holder 125 and the fan holder 700 are realized, which ensures the structural strength of the skin treatment apparatus, and makes the structure of the skin treatment apparatus compact.

As shown in FIG. 21 and FIG. 22, the side of the first side base 714 facing the main control board 600 and the end close to the first base 712 is defined with a notch 7144, and the light emitting side holder 125 is provided with an extension arm 734. The extension arm 734 extends into the notch 7144. One side of the extension arm 734 abuts against the main control board 600, and the opposite side of the extension arm 734 abuts against inner wall of the notch 7144. In this way, the mutual cooperation and positioning of the main control board 600, the light emitting side holder 125 and the fan holder 700 are realized.

Illustratively, in some embodiments, as shown in FIG. 25 and FIG. 29, the side of the first side base 714 away from the main control board 600 and the end close to the first base 712 is defined with a thickness reduction groove 7145. A bottom wall of the thickness reduction groove 7145 is defined with a through hole. The extension arm 734 is provided with a third snap-fit element 735, and the third snap-fit element 735 passes through the through hole and is in snap-fit connection with the bottom wall of the thickness reduction groove 7145. In this way, the third snap-fit element 735 is in snap-fit connection with the first side base 714, realizing a fixed connection between the light emitting side holder 125 and the fan holder 700. This connection is reliable and easy to assemble.

Illustratively, light hair removal is based on the theory of selective photothermal action. The light of a specific wavelength penetrates the epidermis without damaging the epidermal hair follicles, and the hair follicles are coagulated and necrotic by heat, which can effectively slow down the growth of hair, thus playing the role of hair removal. However, the human skin may experience a burning sensation after absorbing the energy of the light emitted by the skin treatment apparatus. The cold compress component 300 can apply a cold compress to the skin to be treated or to the skin in the vicinity of the skin to be treated, thereby improving the comfort when using the skin treatment apparatus.

Optionally, the skin treatment apparatus is a hair removal instrument and/or a skin rejuvenation instrument. The light emitting component 200 is configured to generate the light for hair removal and/or skin rejuvenation. That is, the skin treatment apparatus may be used as a hair removal instrument and/or as a skin rejuvenation instrument, based on the wavelength of the light generated by the light emitting component 200.

As shown in FIG. 20, the first side plate 112 is provided with a button 114 for operation. The second side plate 113 is defined with the air inlet and the air outlet. The fan 500 sucks air through the air inlet. The air sucked into the housing 110 by the fan 500 is blown out through the air outlet after heat exchange. The button 114 is configured to operate the skin treatment apparatus, for example, adjusting the working mode of the light emitting component 200, so as to meet different user requirements. The air inlet is configured for the fan 500 to suck the air, and the air outlet is configured to discharge the air after heat exchange in the skin treatment apparatus. As such, the air flows inside the skin treatment apparatus to dissipate heat from the skin treatment apparatus.

As shown in FIG. 33 to FIG. 40, the light emitting component 200 is defined with a light emitting port 201 for letting the light out. The light transmitting member 310 is located on the side of the filter 220 away from the light emitting component 200, and a spacing space 330 is formed between the light transmitting member 310 and the filter 220. The sealing structure 240 seals the spacing space 330, and the sealing structure 240 is located outside the covering space of the light emitting port 201.

In the embodiments, the sealing structure 240 is the fifth holder, the light transmitting member 310 is fixed by the holder component 120, the light emitted by the light emitting component 200 is filtered by the filter 220 and then irradiated to the light transmitting member 310. The spacing space 330 between the light transmitting member 310 and the filter 220 is sealed by the sealing structure 240, to avoid the formation of water mist in the spacing space 330 which may affect the light irradiation. In addition, the sealing structure 240 is located outside the covering space of the light emitting port 201 of the light emitting component 200, such that the light emitted from the light emitting port 201 will not be irradiated on the sealing structure 240. This prevents the problem in related art that the sealing structure is susceptible to deterioration and carbonization under long-term light exposure, thereby improving the service life of the sealing structure 240 and the skin treatment apparatus, also preventing the production of powdery debris which may affect the light effect.

The sealing structure 240 being located outside the covering space of the light emitting port 201 of the light emitting component 200 may refer to that the sealing structure 240 is located outside the spot of light irradiated on the filter 220 by the light emitting component 200, such that the light exiting from the light emitting outlet will not be directly irradiated to the sealing structure 240. The skin treatment apparatus may be used as a hair removal instrument or as a skin rejuvenation instrument, based on the wavelength of the light generated by the light emitting component 200.

The sealing structure 240 in the embodiments may be a detachable structure or an integrated structure. Illustratively, in the first embodiment, the sealing structure 240 is an integrated sealing structure. The light transmitting member 310 and the filter 220 are in sealing fit with the sealing structure. By using the integrated sealing structure for sealing, the number of parts can be reduced, thereby ensuring the reliability of the sealing.

As shown in FIG. 35 to FIG. 40, the sealing structure is provided an insertion slot 241. The filter 220 is inserted into the insertion slot 241. The connection between the filter 220 and the sealing structure is realized by means of an insertion connection through the insertion slot 241. The inner wall of the insertion slot 241 is provided with an annular sealing rib 242, and the sealing rib 242 abuts against the filter 220. The sealing rib 242 surrounds the ring mouth of the sealing structure. The arrangement in which the sealing rib 242 abuts against the filter 220 further improves the sealing effect, which prevents the water vapor from entering the ring mouth of the sealing structure.

Figure 37:
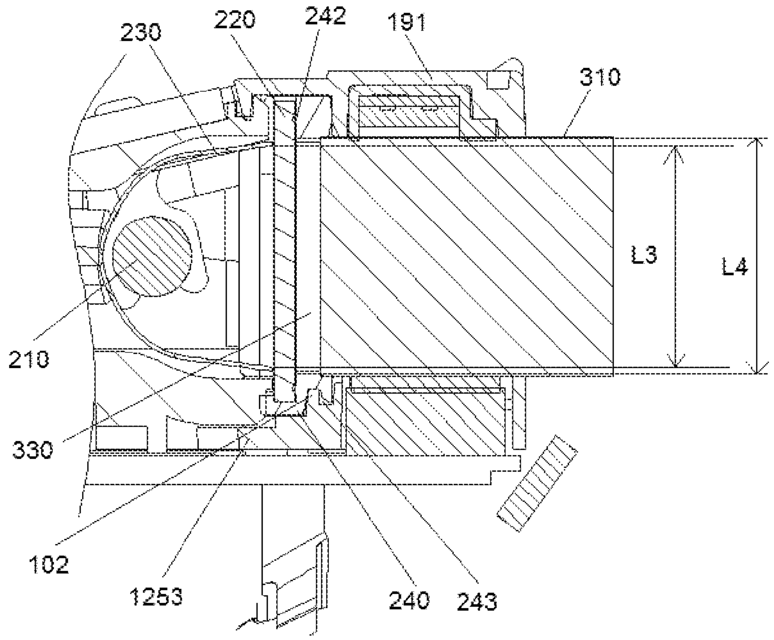
FIG. 37 is a second sectional diagram of a portion of the skin treatment apparatus according to the first embodiment of the present disclosure.
Figure 40:
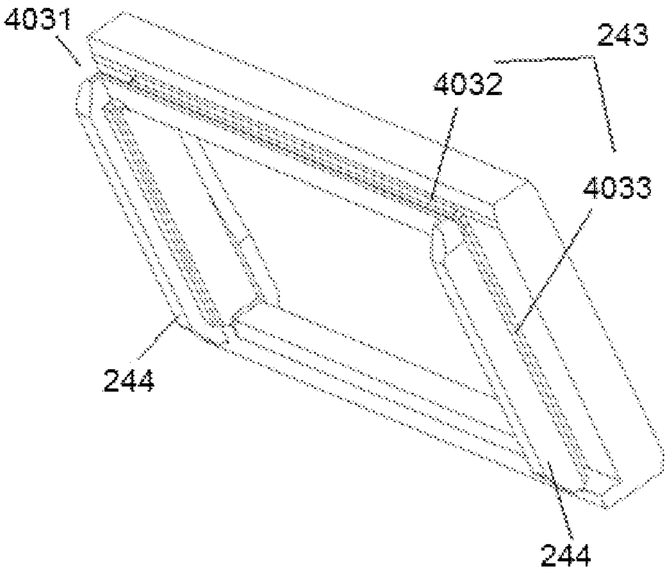
FIG. 40 is a schematic diagram of a sealing ring in FIG. 34 from a second perspective.

As shown in FIG. 37 and FIG. 40, the outer peripheral surface of the sealing structure is defined with a limiting groove 243. The limiting groove 243 is located on the side of the filter 220 away from the light emitting component 200. The holder component 120 is defined with a mounting groove 101. The filter 220 and the sealing structure are mounted in the mounting groove 101. The inner wall of the mounting groove 101 is provided with a limiting protrusion part 102, and the limiting protrusion part 102 is inserted into the limiting groove 243 for limiting fit with the limiting groove 243. The insertion slot 241 is defined with a first insertion port 4011 for inserting the filter 220, the limiting groove 243 is defined with a second insertion port 4031 for inserting the limiting protrusion part 102. The first insertion port 4011 and the second insertion port 4031 are located on two opposite sides of the sealing structure, respectively. An opening direction of the first insertion port 4011 is opposite to an opening direction of the second insertion port 4031. In this way, the limiting protrusion part 102 is inserted into the limiting groove 243 as a result of inserting the sealing structure into the mounting groove 101. Besides, the direction of inserting the filter 220 into the insertion slot 241 is the same as the direction of inserting the sealing structure into the mounting groove 101, which facilitates the assembly of multiple parts.

In the embodiments, the covering space of the light emitting port 201 of the light emitting component 200 is equivalent to a light incoming surface of the light transmitting member 310. The sealing structure 240 does not extend between the filter 220 and the light transmitting member 310, such that the light coming out from the light emitting port 201 will not be directly irradiated on the sealing structure 240.

In the embodiments, a mounting cavity 103 and a mounting groove are defined between the third holder 1253 and the fourth holder 191. The light transmitting member 310 is mounted in the mounting cavity 103, and the sealing structure is mounted in the mounting groove. With this structure, the sealing structure and the light transmitting member 310 can be mounted in the cavity between the third holder 1253 and the fourth holder 191, and the third holder 1253 is fixedly connected to the fourth holder 191 after the sealing structure and the light transmitting member 310 are mounted.

Illustratively, the third holder 1253 is a U-shaped structure, and the fourth holder 191 may be understood as a plate-shaped structure. After mounting the sealing structure, the light transmitting member 310 and the filter 220 into the cavity of the third holder 1253, the cavity opening of the third holder 1253 is covered by the fourth holder 191. This structure is conducive to the fixing of parts and is easy to assemble.

The outer peripheral surface of the sealing structure is defined with the limiting groove 243, which is located on the side of the filter 220 away from the light emitting component 200. The inner wall of the third holder 1253 located in the mounting groove is provided with the limiting protrusion part 102. The limiting protrusion part 102 is in limiting fit with the limiting groove 243. After mounting the sealing structure into the mounting groove, the sealing structure is limited and supported by the limiting protrusion part 102 to ensure the sealing effect.

Figure 34:
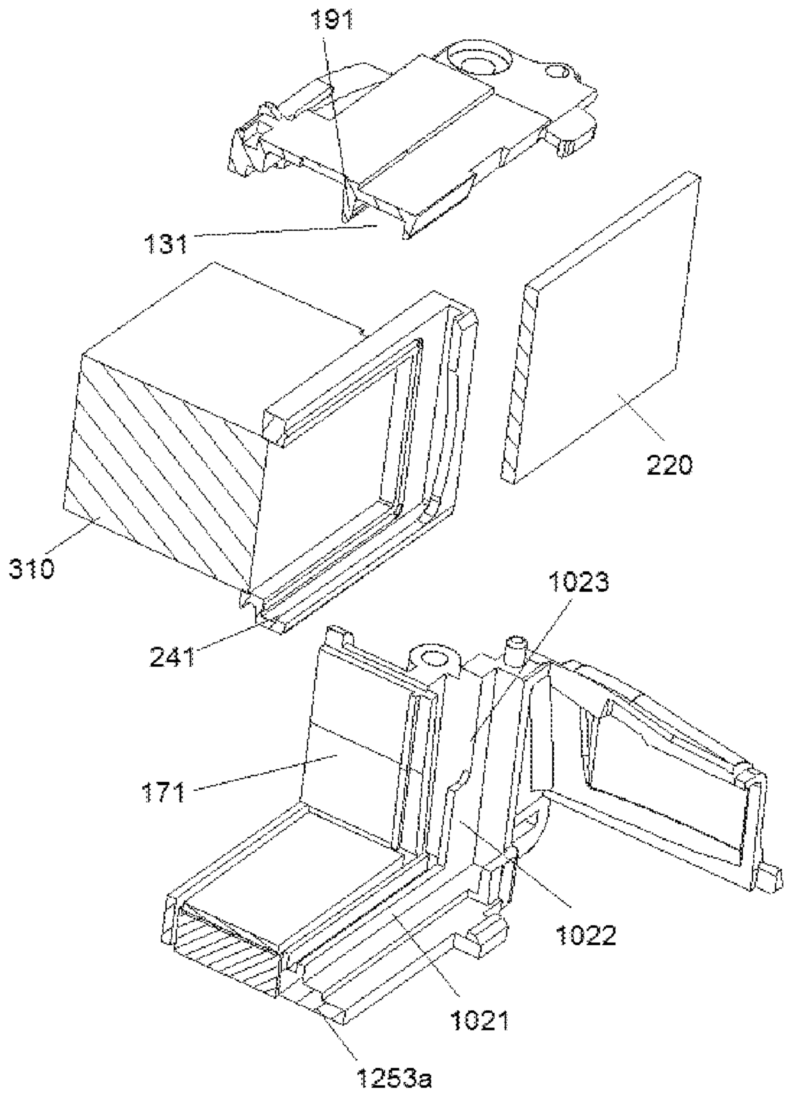
FIG. 34 is an exploded diagram of the skin treatment apparatus in FIG. 33.

Illustratively, as shown in FIG. 34, the limiting protrusion part 102 includes a main protrusion rib 1021 and two side protrusion ribs 1022. The main protrusion rib 1021 is located on the inner wall of the second mounting plate 1253*a*, and the two side protrusion ribs 1022 are located on the inner wall of the first connection support part 171 and/or the second connection support part 172. The limiting groove 243 includes a main strip-shaped groove 4032 and two side strip-shaped grooves 4033. The main strip-shaped groove 4032 is located on one side of the sealing structure facing the second mounting plate 1253*a*. The two side strip-shaped grooves 4033 are located on two opposite sides of the sealing structure. The main protrusion rib 1021 is in limiting fit with the main strip-shaped groove 4032, and the two side protrusion ribs 1022 are in limiting fit with two side strip-shaped grooves 4033. In the embodiments, the limiting protrusion part 102 may be understood as a U-shaped structure, and the limiting groove 243 is also a U-shaped structure, such that the two fit each other after assembly.

In the embodiments, the limiting protrusion part 102 is at least distributed on an inner wall of the first connection support part 171 and/or the second connection support part 172. The side of the third holder 1253 facing the fourth holder 191 is defined with a groove opening for inserting the light transmitting member 310, the sealing structure and the filter 220. A notch 1023 is defined at the position of the limiting protrusion part 102 close to the groove opening. The notch 1023 disposed in the limiting protrusion part 102 avoids the sealing structure, such that it is conducive to inserting the sealing structure into the cavity of the third holder 1253. This prevents a large resistance due to a large contact area between the limiting protrusion part 102 and the sealing structure in case the length of the limiting protrusion part 102 in the direction where the sealing structure is inserted is long. That is, the notch 1023 facilitates the assembly.

In the embodiments, the sealing structure, the filter 220 and the light transmitting member 310 are mounted in the following process: Step 1: The sealing structure is sleeved on the light transmitting member 310. Step 2: The sealing structure and the light transmitting member 310 are mounted into the cavity of the third holder 1253, where the sealing structure is inserted into the mounting groove, the limiting protrusion part 102 fits the limiting groove 243 disposed in the sealing structure, and the limiting protrusion part 102 is absent at the groove opening of the mounting groove. As such, it is convenient to mount the light transmitting member 310 and the sealing structure into the mounting groove; also, it is convenient for the sealing structure to deform and have a buffering capacity after the assembly is completed. Step 3: The filter 220 is inserted into the insertion slot 241 disposed in the sealing structure. Step 4: The groove opening of the mounting groove is covered by the fourth holder 191, so as to fix the sealing structure, the filter 220 and the light transmitting member 310.

Figure 33:
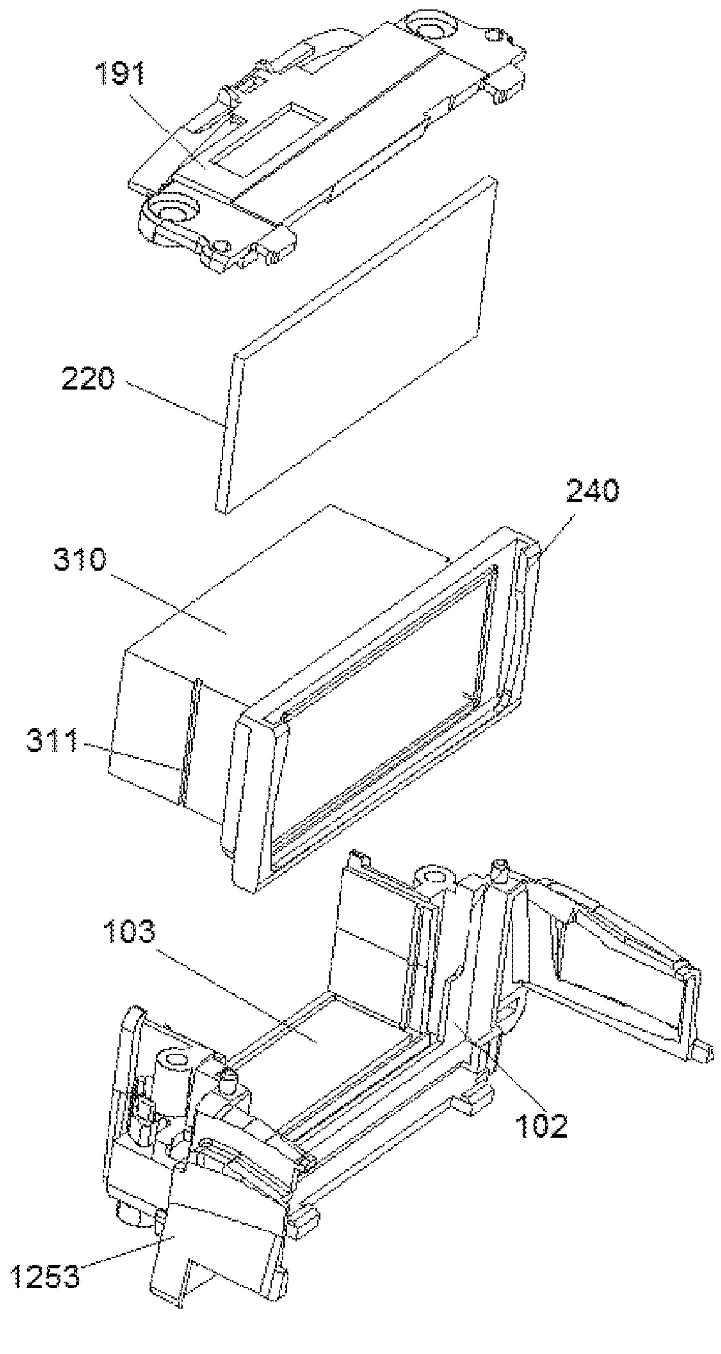
FIG. 33 is a structural schematic diagram of a portion of the skin treatment apparatus according to the first embodiment of the present disclosure.
Figure 35:
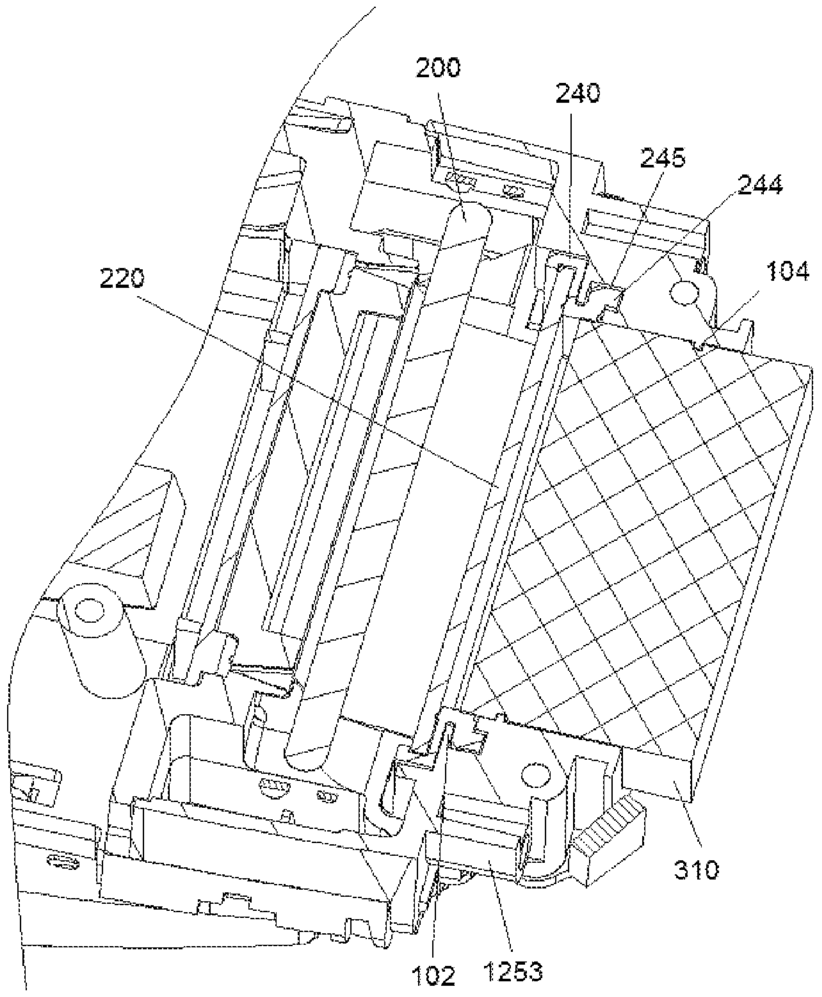
FIG. 35 is a sectional diagram of the skin treatment apparatus in FIG. 34.

As shown in FIG. 33 and FIG. 35, the sealing structure is sleeved on the light transmitting member 310. The inner wall of the mounting cavity is provided with a positioning rib 104, the outer wall of the light transmitting member 310 is defined with a positioning groove 311, and the positioning rib 104 is in limiting fit with the positioning groove 311. Or, the inner wall of the mounting cavity 103 is defined with a positioning groove 311, the outer wall of the light transmitting member 310 is provided with a positioning rib 104, and the positioning rib 104 is in limiting fit with the positioning groove 311. By the cooperation of the positioning rib 104 and the positioning groove 311, the light transmitting member 310 is reliably limited. This ensures the precision of the assembly position, and the precision of the position of the light transmitting member 310 relative to the sealing structure, thereby improving the sealing effect.

Figure 36:
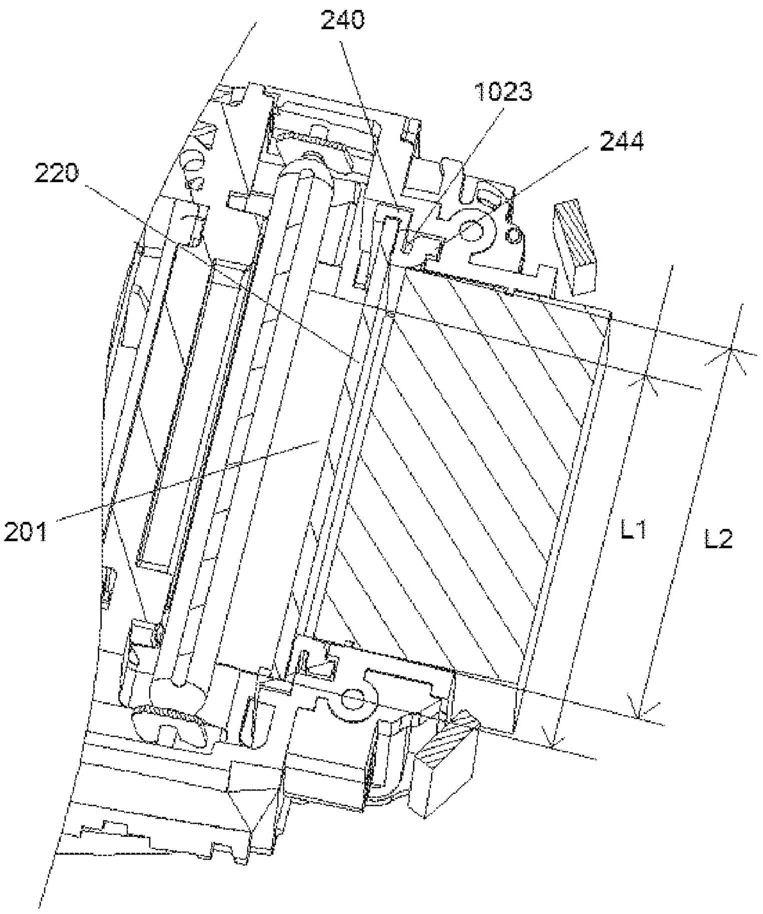
FIG. 36 is a first sectional diagram of a portion of the skin treatment apparatus according to the first embodiment of the present disclosure.

As shown in FIG. 35, FIG. 36 and FIG. 40, the side wall of the limiting groove 243 of the sealing structure away from the light emitting component 200 is bent to form a latching protrusion part 244. The first connection support part 171 and/or the second connection support part 172 includes a latching side face facing the latching protrusion part 244. The latching side face is provided with a latching notch 245 matching the shape of the latching protrusion part 244, the latching protrusion part 244 is latched in the latching notch 245. With this structure, a reliable connection between the sealing structure and the third holder 1253 is realized, and the position of the sealing structure is precisely limited. Also, the sealing effect is improved, and the water vapor is prevented from entering the spacing space.

Illustratively, the outer peripheral surface of the sealing structure is provided with a limiting groove 243, which is located on the side of the filter 220 away from the light emitting component 200. The inner walls of the second mounting plate 1253*a* and the first connection support part 171 and/or the second connection support part 172 located in the mounting groove 101 are provided with the limiting protrusion part 102. The limiting protrusion part 102 is in limiting fit with the limiting groove. The latching protrusion part 244 is located on the side of the limiting groove 243 away from the light emitting component 200. Two latching protrusion parts 244 are provided, and the two latching protrusion parts 244 are located on two opposite sides of the sealing structure. Two latching notches 245 are provided, and the two latching notches 245 are located on the first connection support part 171 and/or the second connection support part 172. The two latching protrusion parts 244 are respectively latched with the two latching notches 245. In this solution, the limiting fit between the limiting protrusion part 102 and the limiting groove 243, and the limiting fit between the two latching protrusion parts 244 and the two latching notches 245 jointly realizes the mounting and positioning of the sealing structure, thereby ensuring the reliability of connection and sealing.

Figure 38:
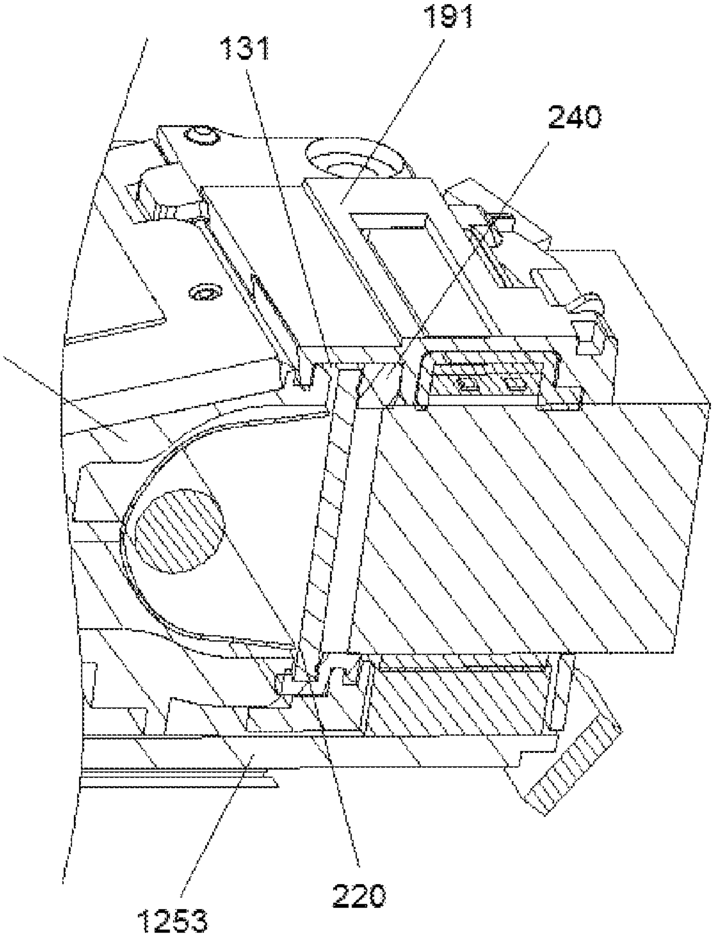
FIG. 38 is a third sectional diagram of a portion of the skin treatment apparatus according to the first embodiment of the present disclosure.
Figure 39:
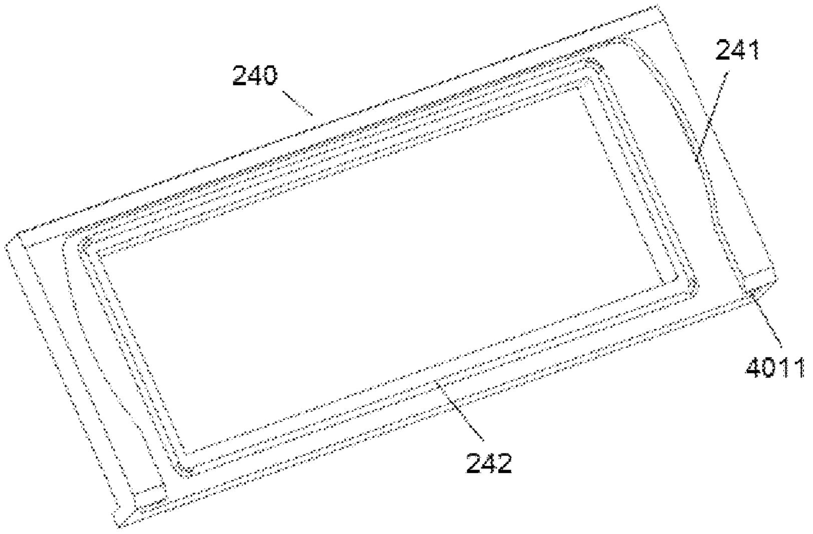
FIG. 39 is a schematic diagram of a sealing ring in FIG. 34 from a first perspective.

As shown in FIG. 38, the side of the fourth holder 191 facing the second mounting plate 1253*a* is defined with a pressure groove 131, which is a part of the mounting groove 101. The sides of the sealing structure and the filter 220 away from the second mounting plate 1253*a* are limited in the pressure groove 131. In this way, the sealing structure is limited in the entire circumferential direction.

In the embodiments, the fourth holder 191 is provided with the pressure groove 131, and the sides of the sealing structure and the filter 220 are limited in the pressure groove 131. The skin treatment apparatus further includes the light emitting side holder 125. The light emitting component 200 is mounted in the cavity of the light emitting side holder 125. The side of the light emitting side holder 125 facing the fourth holder 191 is provided with a third baffle plate, which extends into the pressure groove 131 and is in limiting fit with the inner wall of the pressure groove 131. The light emitting side holder 125 supports the light emitting component 200, and the third baffle plate extends into the pressure groove 131 and is in the limiting fit with the inner wall of the pressure groove 131, such that the light emitting side holder 125 and the fourth holder 191 are limited to each other, thereby ensuring the connection reliability.

In some embodiments, the reflector 230 is provided with the light emitting port 201. In other words, the reflector 230 defines the light emitting port 201. The arc-shaped inner wall of the reflector 230 reflects the light emitted by the light emitting member 210, so that the light is directed to the light emitting port 201 and emitted. Illustratively, the light emitting port 201 is formed by an upper side edge, a lower side edge, and two end side edges of the reflector 230.

As shown in FIG. 36 and FIG. 37, the length of the reflector 230 is L1, the length of the ring mouth of the sealing structure 240 is L2, satisfying: L1≤L2. The distance between two opposite edges (namely, the upper side edge and the lower side edge) of the inner side of the reflector 230 in the width direction is L3, the width of the ring mouth of the sealing structure 240 is L4, satisfying: L3≤L4. The size limitations ensure that the sealing structure 240 is located outside the covering space of the light emitting port 201 of the light emitting component 200. That is, the light exiting from the light emitting port 201 will not be directly irradiated on the sealing structure 240.

As shown in FIG. 41 to FIG. 45, in the second embodiment, the sealing structure 240 includes a first sealing structure 246 and a second sealing structure 247. The first sealing structure 246 is sleeved on the peripheral side of the light transmitting member 310, and the second sealing structure 247 is pressed between the first sealing structure 246 and the filter 220. In this embodiment, the two sealing structures cooperate to realize the sealing of the spacing space 330.

The holder component 120 is defined with the mounting groove. The sealing structure 240 is located in the mounting groove. The side of the first sealing structure 246 away from the second sealing structure 247 is provided with a mating rib 2461. The mating rib 2461 abuts against the side wall of the mounting groove 101 facing the filter 220, which ensures the sealing reliability of the first sealing structure 246 and the holder component 120.

Figure 43:
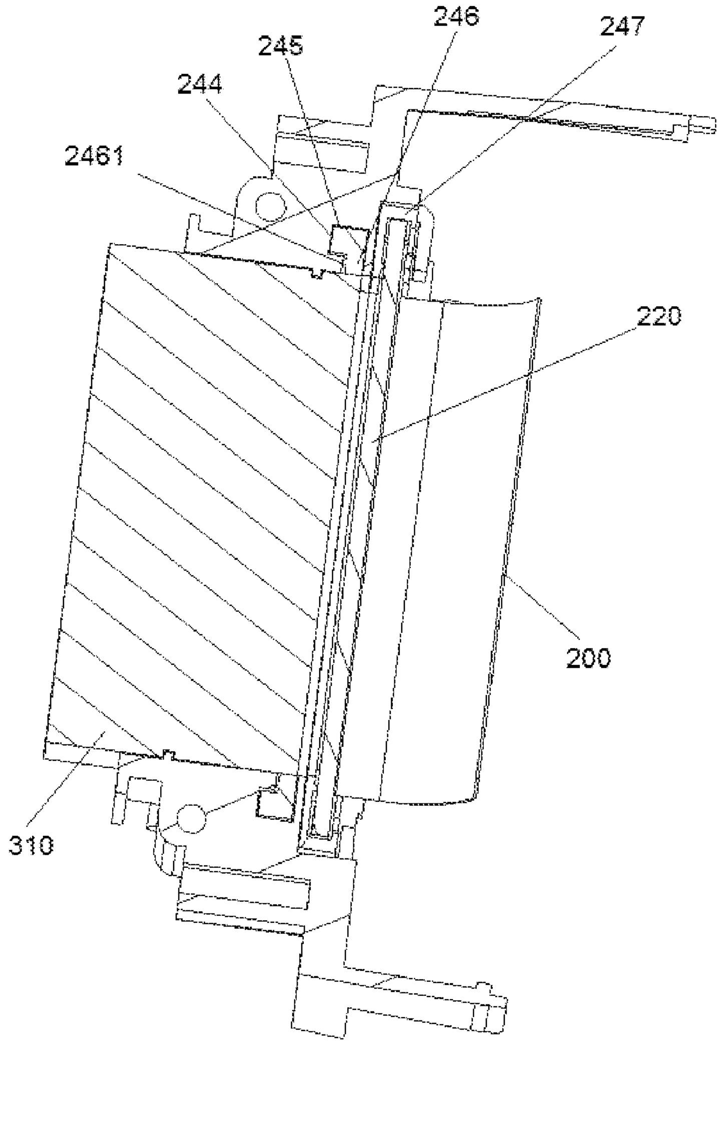
FIG. 43 is a first sectional diagram of the skin treatment apparatus in FIG. 41.
Figure 44:
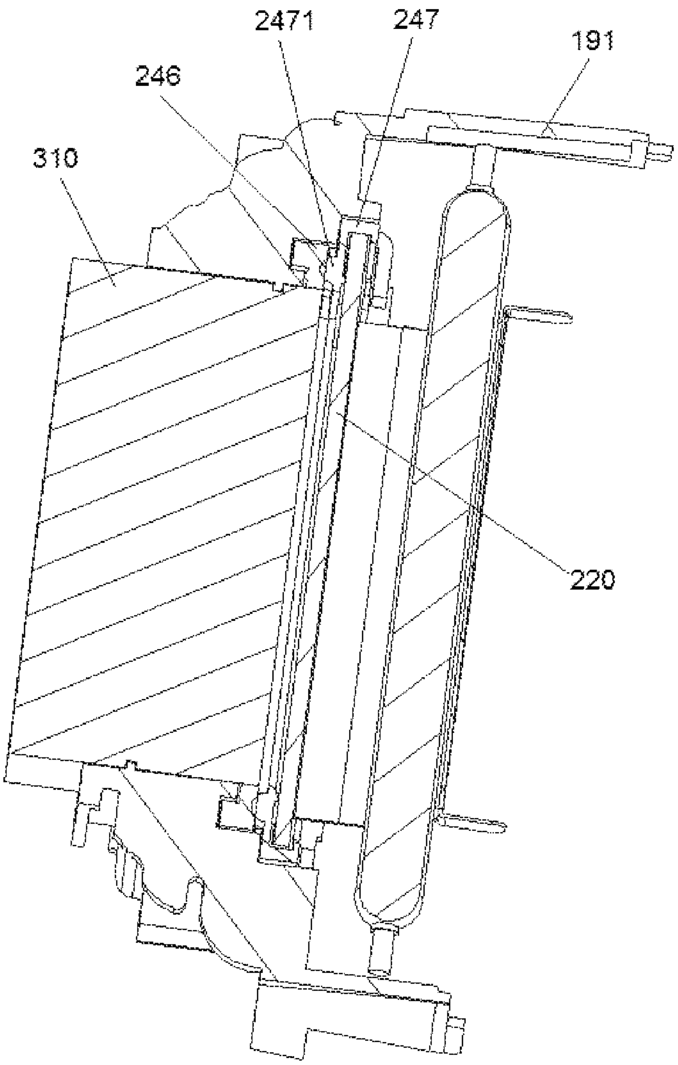
FIG. 44 is a second sectional diagram of the skin treatment apparatus in FIG. 41.
Figure 45:
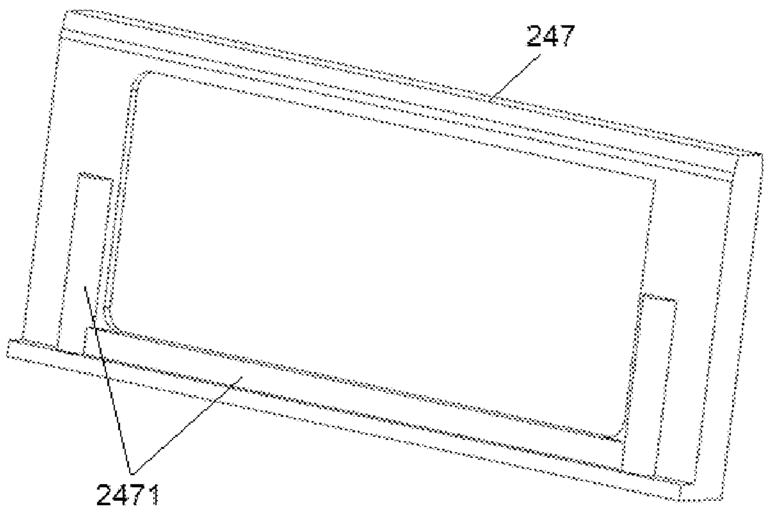
FIG. 45 is a schematic diagram of a second sealing ring in FIG. 42.

As shown in FIG. 43, the side of the first sealing structure 246 away from the second sealing structure 247 is provided with a latching protrusion part 244. The latching protrusion part 244 is located on the side of the mating rib 2461 away from the center of the first sealing structure 246. The side wall of the mounting groove facing the filter 220 is defined with a latching notch 245. The latching protrusion part 244 is latched into the latching notch 245. This structure helps to realize a reliable connection between the first sealing structure 246 and the holder component 120, and precisely limits the position of the first sealing structure 246. Also, this structure improves the sealing effect so as to prevents water vapor from entering the spacing space 330.

In some embodiments, the surface of the first sealing structure 246 is attached to the surface of the second sealing structure 247. Or, in the second embodiment, the holder component 120 is defined with the mounting groove, the holder component 120 is provided with the limiting protrusion part 102 located on an inner wall of the mounting groove. The limiting protrusion part 102 is located in a gap between the first sealing structure 246 and the second sealing structure 247, to position and seal the first sealing structure 246 and the second sealing structure 247. The limiting protrusion part 102 limits the first sealing structure 246 and the second sealing structure 247 in the axial direction of the first sealing structure 246 and the second sealing structure 247.

In an embodiment not shown in figures, the limiting protrusion part 102 includes a partition ring and a protrusion part. The partition ring abuts against the side of the first sealing structure 246 facing the second sealing structure 247, and the protrusion part is disposed on the side of the partition ring away from the first sealing structure 246. The second sealing structure 247 is sleeved on the protrusion part, and the second sealing structure 247 is pressed between the partition ring and the filter 220. By the partition ring and the protrusion part, precise positioning of the first sealing structure 246 and the second sealing structure 247 are realized, and sealing is achieved by close attachment of the first sealing structure 246 and the second sealing structure 247.

In an embodiment not shown in the figures, the inner circumferential surface of the partition ring is provided with a positioning protrusion part, and the side of the light transmitting member 310 facing the filter 220 abuts against the positioning protrusion part. The positioning protrusion part helps to improve the positioning effect on the filter 220. The positioning protrusion part may be provided as a plurality of blocks disposed along the circumferential direction of the partition ring.

In the second embodiment, the first sealing structure 246 abuts against a part of the surface of the second sealing structure 247, and a gap is formed between the first sealing structure 246 and the other part of the surface of the second sealing structure 247. The skin treatment apparatus further includes a limiting protrusion part 102, which is located in the gap between the first sealing structure 246 and the second sealing structure 247. The limiting protrusion part 102 can limit the first sealing structure 246 and the second sealing structure 247.

Figure 41:
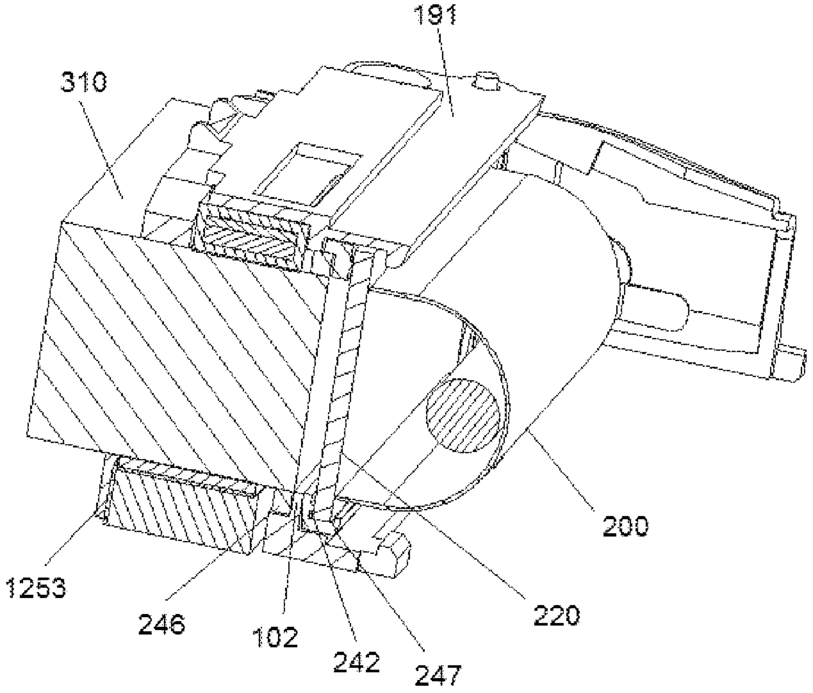
FIG. 41 is a structural schematic diagram of a portion of the skin treatment apparatus according to the second embodiment of the present disclosure.
Figure 42:
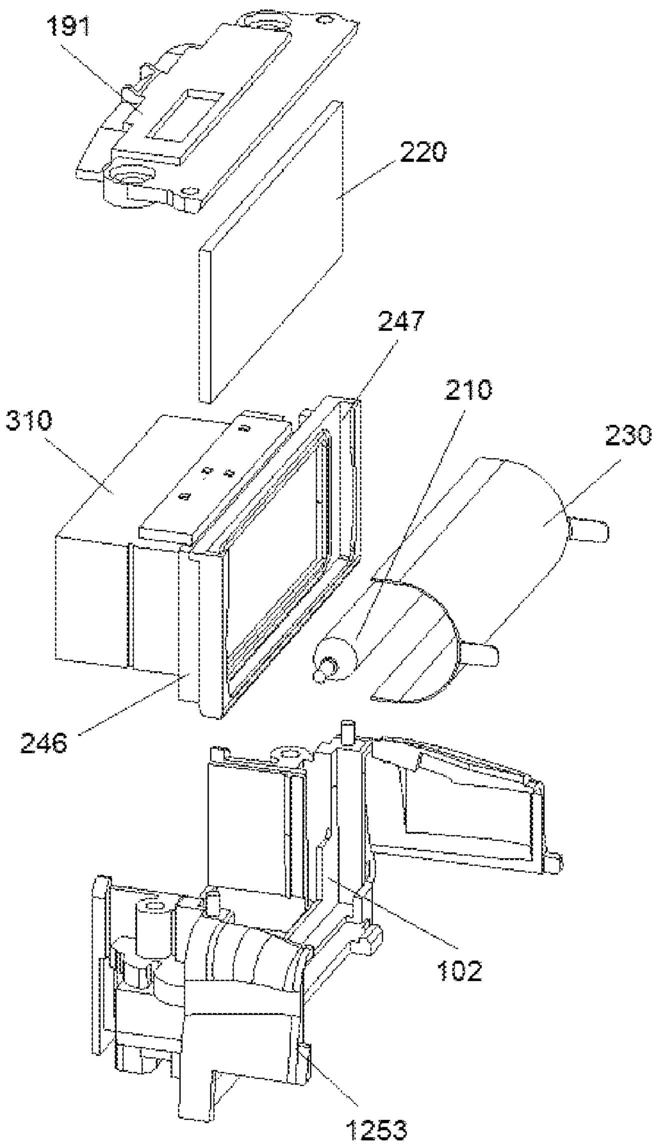
FIG. 42 is an exploded diagram of the skin treatment apparatus in FIG. 41.

As shown in FIG. 41 to FIG. 43, the limiting protrusion part 102 is semi-annular, the side of the second sealing structure 247 facing the first sealing structure 246 is provided with a semi-annular protrusion 2471. The semi-annular limiting protrusion part 102 and the semi-annular protrusion 2471 jointly enclose the covering space of the light emitting port 201. The gap between the first sealing structure 246 and the second sealing structure 247 is semi-annular and matches the shape of the limiting protrusion part 102. The semi-annular protrusion 2471 abuts against a part of the surface of the first sealing structure 246. In this way, the semi-annular protrusion 2471 and the limiting protrusion part 102 jointly seal the gap between the first sealing structure 246 and the second sealing structure 247.

As shown in FIG. 41, the side of the second sealing structure 247 facing the light emitting component 200 is provided with an annular sealing rib 242, which abuts against the filter 220. In this way, the sealing rib 242 ensures a reliable sealing between the second sealing structure 247 and the filter 220.

In the second embodiment, the side of the second sealing structure 247 facing the light emitting component 200 is defined with the insertion slot 241, and the filter 220 is inserted into the insertion slot 241. The connection between the filter 220 and the second sealing structure 247 is realized by means of an insertion connection through the insertion slot 241, which is convenient for assembly.

In an embodiment not shown in the figures, the second sealing structure 247 may be entirely disposed on the side of the filter 220 away from the light emitting component 200, and the surface of the second sealing structure 247 is attached to the surface of the filter 220. In this way, the sealing between the second sealing structure 247 and the filter 220 is also realized.

Figure 46:
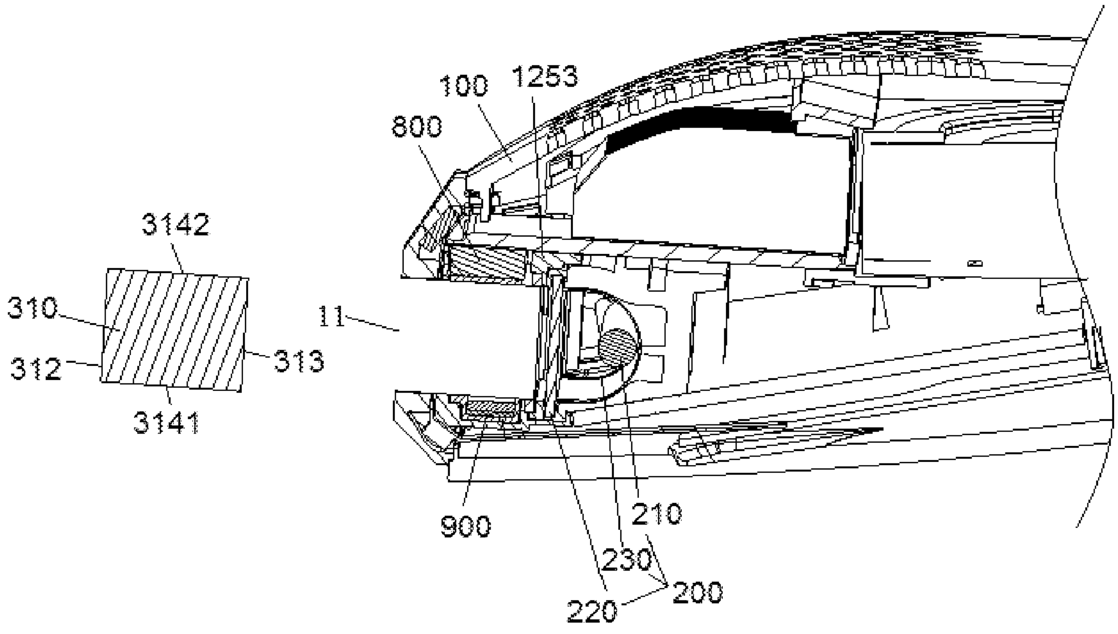
FIG. 46 is a disassembly diagram of a portion of the skin treatment apparatus in FIG. 42.

As shown in FIG. 46, in an embodiment, the phototherapy lamp 900 may be a first sub-light emitting component, and the light emitting component 200 may be a second sub-light emitting component. The first sub-light emitting component is configured to emit first light toward the light transmitting member 310, and the light transmitting member 310 transmits at least part of the first light out through a light outgoing surface 312 and the light outlet 11 for phototherapy on the skin, and in this case, the skin treatment apparatus is served as a phototherapy instrument. That is, the first sub-light emitting component is a phototherapy component. The second sub-light emitting component is configured to emit second light toward the light transmitting member 310, and the light transmitting member 310 transmits at least part of the second light out through the light outgoing surface 312 and the light outlet 11, for hair removal and/or skin rejuvenation, and in this case, the skin treatment apparatus is served as a hair removal instrument and/or a skin rejuvenation instrument. That is, the second sub-light emitting component is a hair removal component, or a skin rejuvenation component, or a component having both hair removal and skin rejuvenation functions.

Illustratively, the skin treatment apparatus can not only perform the phototherapy treatment on the skin, but also perform the hair removal and/or skin rejuvenation treatment on the skin. Besides, both the first light and the second light of the skin treatment apparatus of the present disclosure can exit from the light outgoing surface 312, such that the first light and the second light exiting from the light outgoing surface 312 and the light outlet 11 can act on the same skin simultaneously. Therefore, the skin treatment apparatus of the present disclosure can perform different skin treatments on the same skin simultaneously or successively. That is, the skin treatment apparatus of the present disclosure can perform the phototherapy treatment on the skin that is undergoing the hair removal treatment at the same time, and or perform the phototherapy treatment on the skin that has undergone the hair removal treatment in time, thereby improving the user experience. It can be seen that the skin treatment apparatus of the present disclosure provides a better user experience, and solves the problem in related art that the skin treatment apparatus cannot perform the hair removal treatment and the phototherapy treatment on the same skin at the same time and resulting in a poor user experience.

In addition, for the existing skin treatment apparatus, a light transmitting area of the second light needs to be disposed on a light-exit end surface of the housing component. Since the light transmitting area of the second light will inevitably occupy a part of the light exit end surface, the size of the light emitting port is limited by the light transmitting area of the second light. However, in the present disclosure, the first light and the second light are both emitted from the light outgoing surface 312 and the light outlet 11, and there is no need to dispose the light transmitting area of the second light. Thus, the size of the light outlet 11 is not limited, which is beneficial to increase the light outlet 11 and the light outgoing surface 312; that is, it is beneficial to increase the proportion (such as, up to 90% or more) of the light outgoing surface 312 and the light outlet 11 on the light-exit end surface 12 of the housing component 100. The light-exit end surface 12 is the surface of the housing component where the light outlet 11 is located, thus the effective light exit area on the light-exit end surface is enhanced.

Illustratively, the light transmitting member 310 is a light transmitting crystal. The material of the light transmitting crystal is at least one of sapphire, quartz glass, and crystal. The sapphire has good skin-friendly touch, and it can reach a low temperature close to zero by cooperating with the cooling member to make the temperature of the skin adjacent to the light outlet 11 infinitely close to the freezing point, which greatly relieves a burning pain. Also, a short-term contact will not cause skin damage. The sapphire cooperating with the cooling member refers to that the thermal conduction connection between the cooling member is in a thermal conductive connection with sapphire to allow the cooling member to cool down the sapphire.

Optionally, the second sub-light emitting component is an IPL light-emitting light source component to generate intense pulsed light, also known as pulsed intense light. The IPL is a type of broad-spectrum light generated after a high-intensity light source has been focused and filtered. The wavelength of the IPL is mostly 400 nanometer (nm) to 200 nm, and the IPL with different wavelengths has different functions. For example, the IPL with a wavelength of 690 nm to 1200 nm uses the principle of photo pyrolysis of the IPL and accordingly has the hair removal effect. Since the melanocytes in the hair follicles can selectively absorb light in a specific wavelength band, and the IPL can penetrate the epidermis and directly reach the hair follicles, light energy in the dermis is absorbed by the melanocytes in the hair follicles and then converted into heat energy to increase the temperature of the hair follicles. When the temperature of the hair follicles is high enough, the structure of the hair follicles will be irreversibly damaged, and the damaged hair follicles will naturally fall off after a period of time. As a result, the hair growth will be delayed or even inhibited in a short period of time. For another example, the IPL with a wavelength of 560 nm to 640 nm mainly has a skin rejuvenation effect. Alternatively, the second sub-light emitting component is a laser light emitting component to generate laser light, so as to achieve hair removal by laser.

Optionally, the first light includes at least one of red light, blue light, and yellow light. The wavelength of the blue light is 450 nm to 490 nm, the wavelength of the yellow light is 567 nm to 607 nm, and the wavelength of the red light is 620 nm to 660 nm.

For example, the first light includes light emitting diode (LED) light, which is cold light emitted by a narrow-spectrum light source. The light energy is converted into cell energy without generating high heat and not burning the skin, thus LED light therapy is a safe way to treat the skin. LED red light can promote whitening and skin rejuvenation, lightening spots and removing wrinkles. LED blue light can promote deep sterilization and balance oil. LED orange light can supplement cell energy, strengthen muscles, improve relaxation, etc. LED green light is absorbed by skin and has sedative effect, which helps to dilute pigmented spots and show brighter skin color. This sedative effect also has anti-inflammatory effect and can relieve skin surface.

In an embodiment, the light transmitting member 310 further includes a light incoming surface 313 facing the light outgoing surface 312. The second sub-light emitting component is configured to emit the second light toward the light incoming surface 313.

Illustratively, the second sub-light emitting component includes a second light emitting part 2521 configured to emit the second light. The second light emitting part 2521 faces the light incoming surface 313, such that the second light emitted by the second light emitting part 2521 enters the light transmitting member 310 through the light incoming surface 313, and then exits through the light outgoing surface 312.

In an embodiment, the light transmitting member 310 further includes a side surface part 314 connected between the light outgoing surface 312 and the light incoming surface 313. The first sub-light emitting component is configured to emit the first light toward the side surface part 314.

Illustratively, the side surface part 314 includes a first side surface 3141. The first sub-light emitting component includes a first light emitting part 31 configured to emit the first light. The first light emitting part 31 faces the first side surface 3141, to emit the first light into the light transmitting member 310 through the first side surface 3141.

Since the first sub-light emitting component and the second sub-light emitting component are disposed in different directions of the light transmitting member 310, the incoming direction of the first light is different from the incoming direction of the second light, and the outgoing path of the first light is different from the outgoing path of the second light after passing through the light transmitting member 310. However, since the light outgoing surfaces are the same, the first light and the second light can realize the superposition of different functions of the skin treatment apparatus, however, the structures of the first sub-light emitting component and the second sub-light emitting component do not affect each other. For example, the first sub-light emitting component and the second sub-light emitting component may be turned on at the same time, to achieve the superposition of the phototherapy function and the hair removal and/or skin rejuvenation function. Alternatively, only the first sub-light emitting component may be turned on to realize the phototherapy function; or only the second sub-light emitting component may be turned on to realize the hair removal and/or skin rejuvenation function.

Illustratively, the side surface part 314 includes a plurality of side surfaces connected successively. The plurality of side surfaces includes the first side surface 3141. Among the side surfaces except the first side surface 3141 in the plurality of side surfaces, at least one side surface is provided with a reflective film. Alternatively, among the side surfaces except the first side surface 3141 in the plurality of side surfaces, at least one side surface is a diffuse reflection surface, such that a diffuse reflection phenomenon can occur on the diffuse reflection surface. For example, at least one side surface is a rough surface having a microstructure to form the diffuse reflection surface. By disposing a reflective film on the side surface or providing a diffuse reflection surface, the light incident into the light transmitting member 310 is diffused or reflected and then exits through the light outgoing surface 312, which further improves the light exit rate, thereby reducing the loss of the first light and/or the second light. In addition, through the diffuse reflection effect of the diffuse reflection surface, the light uniformity and softness can also be improved, and the light exit rate can be ensured.

Illustratively, the reflective film may be a metal reflective film or an all-dielectric reflective film, or a reflective film in which a metal reflective film and an all-dielectric reflective film are combined.

Optionally, the thickness of the reflective film is d, satisfying: 0.1 mm≤d≤0.2 mm. The reflective film is relatively thin, so it can reflect light without affecting the heat dissipation of the light transmitting member 310.

Optionally, the side surface part 314 includes four side surfaces. Preferably, the light transmitting member 310 is a cuboid. Alternatively, the light transmitting member 310 is a cylinder or a prism.

Optionally, the light outgoing surface 312 is a rectangular surface, or a circular surface, or a curved surface; the light incoming surface 313 is a rectangular surface, or a circular surface, or a curved surface; the side surface is a rectangular surface, or a circular surface, or a curved surface. For example, the light incoming surface 313 in FIG. 21 is an curved surface, namely, the cross section of the light incoming surface 313 in FIG. 21 is an arc; the light incoming surface 313 in FIG. 22 is a bending surface formed by three planes, namely, the cross section of the light incoming surface 313 in FIG. 22 is trapezoidal; the light incoming surface 313 in FIG. 23 is formed by two planes, namely, the cross section of the light incoming surface 313 in FIG. 23 is V-shaped; the light outgoing surface 312 and the first side surface 3141 in FIG. 24 are rectangular planes. It should be noted that the light incoming surface 313 may be a bending surface formed by two, three, or even more planes or curved surfaces. The light transmitting member 310 in FIG. 24 is a triangular prism, whose top surface is the first side surface 3141, and whose two side surfaces are the light incoming surface 313 and the light outgoing surface 312.

In an embodiment, the light outgoing surface 312 is located at the light outlet 11.

Illustratively, the light outgoing surface 312 is located in the same plane as the surface where the light outlet 11 is located; or, at least part of the light outgoing surface 312 protrudes toward the outside of the housing component 100 with respect to the surface where the light outlet 11 is located.

Illustratively, the inner wall of the light outlet 11 is attached to the side surface part 314 of the light transmitting member 310.

In an embodiment, the light incoming surface 313 is a diffuse reflection surface, so that at least part of the first light entering the light transmitting member 310 can be directed out from the light outgoing surface 312 under the diffuse reflection effect of the light incoming surface 313.

Illustratively, the light incoming surface 313 is provided with a plurality of bumps 3131. The bumps 3131 protrude toward a direction away from the light outgoing surface 312, to allow the light incoming surface 313 to be the diffuse reflection surface. One bump 3131 forms one diffuse reflection dot. In addition, under the diffuse reflection effect of the diffuse reflection surface formed by the plurality of bumps 3131, better light conduction and diffuse reflection can be realized, which makes the light emitted more evenly, thereby ensuring the light emitting rate.

Illustratively, the bump 3131 is a micro-convex structure to form a rough surface.

Illustratively, the bump 3131 is formed through an etching process. The etching process refers to a process of removing a thin film layer that is not masked by a resist, to obtain exactly the same pattern on the thin film as on the resist film. The etching may selectively remove the part of the thin film layer that is not masked by the resist using a chemical method, or a physical method, or a combination thereof, so that the pattern on the thin film is exactly the same as that on the resist film. The etching technology mainly includes dry etching and wet etching. The dry etching mainly uses a reaction gas and plasma for etching. The wet etching mainly uses a chemical reagent to chemically react with an etched material for etching. The etching process is a well-known technology in the art, which is mature in the related industry chain, and it is advantageous to reduce the manufacturing cost.

Illustratively, the plurality of bumps 3131 are arranged at intervals on the light incoming surface 313.

Optionally, the projection of the bump 3131 on the light incoming surface 313 is circular, or polygon, or oval, or irregular.

Optionally, the interval between any two adjacent bumps 3131 ranges from 0.001 mm to 0.2 mm. For example, the interval may be 0.001 mm, 0.002 mm, 0.005 mm, 0.01 mm, 0.05 mm, 0.1 mm, 0.15 mm, or 0.2 mm.

Optionally, a diameter or an equivalent diameter of the projection of the bump 3131 on the light incoming surface 313 ranges from 20 micrometers to 50 micrometers. For example, the diameter or the equivalent diameter is 20 micrometers, 25 micrometers, 30 micrometers, 36 micrometers, 40 micrometers, 44 micrometers, or 50 micrometers.

Optionally, a protrusion height of the bump 3131 ranges from 5 micrometers to 15 micrometers. For example, the protrusion height is 5 micrometers, 6 micrometers, 8 micrometers, 10 micrometers, 11 micrometers, 13 micrometers, or 15 micrometers.

Optionally, the plurality of side surfaces include a second side surface 3142 facing the first side surface 3141. The light enters the light transmitting member 310 through the first side surface 3141; that is, the first side surface 3141 is adjacent to the first light sub-emitting component. The luminous flux adjacent to the first light sub-emitting component is larger than the luminous flux far away from the first sub-emitting component. As shown in FIG. 19, the distribution density of the bumps 3131 gradually increases in the direction from the first side surface 3141 to the second side surface 3142. For the light reaching the diffuse reflection surface on the light incoming surface 313 away from the first sub-light emitting component, due to the small luminous flux, increasing the distribution density of the scattering dots on the diffuse reflection surface can increase the chance of light scattering, thereby increasing the probability of light exiting from the light outgoing surface 312 of the light transmitting member 310. This improves the utilization of light, thereby improving the phototherapy efficiency. The arrow direction in FIG. 19 is the direction from the first side surface 3141 to the second side surface 3142. Alternatively, as shown in FIG. 18, the plurality of bumps 3131 are evenly distributed on the light incoming surface 313.

In a specific implementation process, the heat generated by the first sub-light emitting component is quickly diffused to the cooling plate 800 after passing through the light transmitting member 310, so that the light transmitting member 310 reaches a low temperature close to zero, and the temperature of the skin close to the light outlet 11 is infinitely close to the freezing point, which greatly relieves the burning sensation.

Illustratively, the cooling plate 800 faces the second side surface 3142 of the light transmitting member 310.

In an embodiment, the first sub-light emitting component includes a first light emitting part configured to emit the first light. The first light emitting part includes a circuit board and a plurality of light emitting members. The plurality of light emitting members are mounted on the circuit board. The light generated by at least part of the light emitting members is the first light. The surface of the circuit board on which the plurality of light emitting members are mounted faces the first side surface 3141.

Illustratively, the light emitting member is light emitting wafers or lamp beads. The light emitting wafers or the lamp beads are integrated on the circuit board, so that the light source can be centralized and thereby allowing a plurality of light sources to be integrated in a small area. For example, dozens of LED lamps can be integrated to improve the irradiance.

Illustratively, the circuit board faces the first side surface 3141, so that the light generated by at least part of the plurality of light emitting members enters the light transmitting member 310 through the first side surface 3141.

Optionally, the circuit board may be a printed circuit board (PCB) or a flexible printed board (FPB). The printed circuit board is a support of the electronic components and also a carrier for the interconnection of the electronic components. Since it is made by electronic printing, it is called "printed" circuit board. The flexible circuit board is a kind of printed circuit board. It is a highly reliable and excellent flexible printed circuit board made of polyimide or polyester film as a base material. It has the characteristics of high wiring density, light weight, thin thickness, and good bending.

Optionally, the light emitting wafer may be a light-emitting diode wafer. The light-emitting wafer may include eutectic circles of different light emitting colors. For example, the light-emitting wafer includes at least one of a red LED eutectic circle, a green LED eutectic circle, a blue LED eutectic circle, and a eutectic semiconductor wafer. Alternatively, the light-emitting wafer is a eutectic red-green-blue triad wafer. Any type of eutectic wafer can be installed on an eutectic pad by means of eutectic welding. An electrical connection is formed by the eutectic pad and an Indium Tin Oxide (ITO) film circuit layer. The ITO film circuit layer is attached to the surface of the substrate. The positive and negative electrode pads of the light-emitting eutectic circle are located under the wafer, so they can be connected to the substrate by means of direct attach (DA). The reverse-die flip-chip structure of the top enables the front and side surfaces of the top to have a higher light output.

Optionally, the lamp bead is a LED lamp bead, mainly including a chip, a holder, gold lines, and a transparent resin. The support holder includes a substrate, a heat dissipation base, a pin, and the like.

In an embodiment, the circuit board includes a two-layer structure, and the plurality of light emitting members are integrated in the middle of the two-layer structure. A mounting case 62 is sleeved on the outer periphery of the two-layer structure.

Illustratively, the circuit board is a double-layer circuit board, including a first layer and a second layer. The first layer and the second layer both have copper wires, and the wires on the two layers can be conducted through through-wire holes, to form a required network connection.

In an embodiment, the plurality of light emitting members are divided into a first light emitting unit and a second light emitting unit. The first light emitting unit includes at least one light emitting member, and the second light emitting unit includes at least one light emitting member. The color of light emitted by the light emitting member in the first light emitting unit is different from the color of light emitted by the light emitting member in the second light emitting unit.

In particular, the first sub-light emitting component may also be configured as an indication light source, to indicate an operation mode of the skin treatment apparatus. For example, the first sub-light emitting component has a first light emitting mode, a second light emitting mode, and a third light emitting mode. In case the first sub-light emitting component is in the first light emitting mode, the light emitting member in the first light emitting unit emits light, but the light emitting member of the second light emitting unit does not emit light.

In case the first sub-light emitting component is in the second light emitting mode, the light emitting member in the first light emitting unit does not emit light, but the light emitting member of the second light emitting unit emits light. In case the first sub-light emitting component is in the third light emitting mode, the light emitting member in the first light emitting unit and the light emitting member in the second light emitting unit emit light alternately.

Optionally, the light emitting member of the first light emitting unit is a red-light light emitting member. That is, the color of the light emitted by the light emitting member of the first light emitting unit is red.

Optionally, the light emitting member of the second light emitting unit is an orange-light light emitting member. That is, the color of the light emitted by the light emitting member of the second light emitting unit is orange.

Optionally, in case the first light emitting unit includes a plurality of light emitting members and the second light emitting unit includes a plurality of light emitting members, a distribution direction of the plurality of light emitting members in the first light emitting unit is parallel to a distribution direction of the plurality of light emitting members in the second light emitting unit.

In an embodiment, the first sub-light emitting component further includes a uniform light plate disposed between the first light emitting part and the light transmitting member 310, so that the first light emitted by the first light emitting part enters the light transmitting member 310 after passing through the uniform light plate.

Illustratively, the uniform light plate is disposed between the circuit board and the light transmitting member 310.

In an embodiment, the second sub-light emitting component further includes a reflective element. The reflective element encloses a reflective space. The second light emitting part is disposed in the reflective space to reduce leakage of the second light. The second light emitting part is located on the side of the reflective element facing the light transmitting member 310, so that the reflective element reflects at least part of the second light toward the light transmitting member 310.

Illustratively, the second sub-light emitting component further includes a filter 220. The filter 220 is disposed on the side of the reflective element facing the light transmitting member 310, so that the filter 220 is located on the light exit path of the reflective element. The filter 220 is configured to filter out the harmful light (such as ultraviolet light) in the strong pulse light, to allow target light from which the harmful light has been filtered out to act on the human skin. The target light can penetrate the epidermis and directly reach the hair follicles, and then is absorbed by the melanocytes in the hair follicles. As such, the temperature of the hair follicles is increased, and the heat damages the hair follicles, which inhibits their ability to grow new hair.

Optionally, the second light emitting part is a light emitting tube. For example, the light emitting tube is an IPL tube.

Optionally, the reflective element is an arc structure. For example, the reflective element is an arc-shaped cover.

Optionally, the reflective element is the reflective cup.

Illustratively, the reflective element is defined with a reflective opening 422 communicated with the reflective space. The filter 220 is connected to or abutted against the reflective element. The filter 220 is disposed at the reflective opening 422.

In an embodiment, a plurality of first sub-light emitting components are provided. The plurality of first sub-light emitting components are configured to emit the first light toward the light transmitting member 310, so that the light transmitting member 310 transmits at least part of the first light of each first sub-light emitting component through the light outgoing surface 312 and the light outlet 11, so as to perform the phototherapy treatment on the skin.

Illustratively, the side surface part 314 includes a plurality of first side surfaces 3141. The first light emitting parts of the plurality of first sub-light emitting components face the plurality of first side surfaces 3141 in a one-to-one correspondence, so that the first light emitting part of each first sub-light emitting component emits the first light into the light-transmitting member 310 through the corresponding first side surface 3141.

Optionally, the first light emitted by the plurality of first sub-light emitting components has different colors. In a specific implementation, at least one first sub-light emitting component may be turned on to perform the phototherapy treatment on the skin, thereby realizing different light therapy effects.

Optionally, the first light emitted by the plurality of first sub-light emitting components has different types and paths, which is advantageous to achieve more skin care functions and can reduce mutual interference of different first light paths.

As shown in FIG. 47 to FIG. 58, the inner cavity and the outside of the housing component 100 are communicated through the air vent part 12. Illustratively, the housing component 100 has a length direction. The outer wall surface of the housing component 100 includes a concave part 115. The housing component 100 includes a front end and a rear end in the length direction D3 of the housing component 100. When using the skin treatment apparatus for skin care, the front end of the housing component 100 is placed toward or close to the skin. In the direction from the front end to the rear end of the housing component 100, the wall surface of the concave part 115 includes a first wall section 116 and a second wall section 117 connected with each other. The first wall section 116 is located on the front side of the second wall section 117 close to the housing component 100. In the direction from the front end to the rear end of the housing component 100, the first wall section 116 is gradually close to the inner cavity of the housing component 100 to form the concave part 115. At least part of the first wall section 116 and at least part of the second wall section 117 form the grip area 16. The air vent part 12 is located outside the grip area 16.

Figure 49:
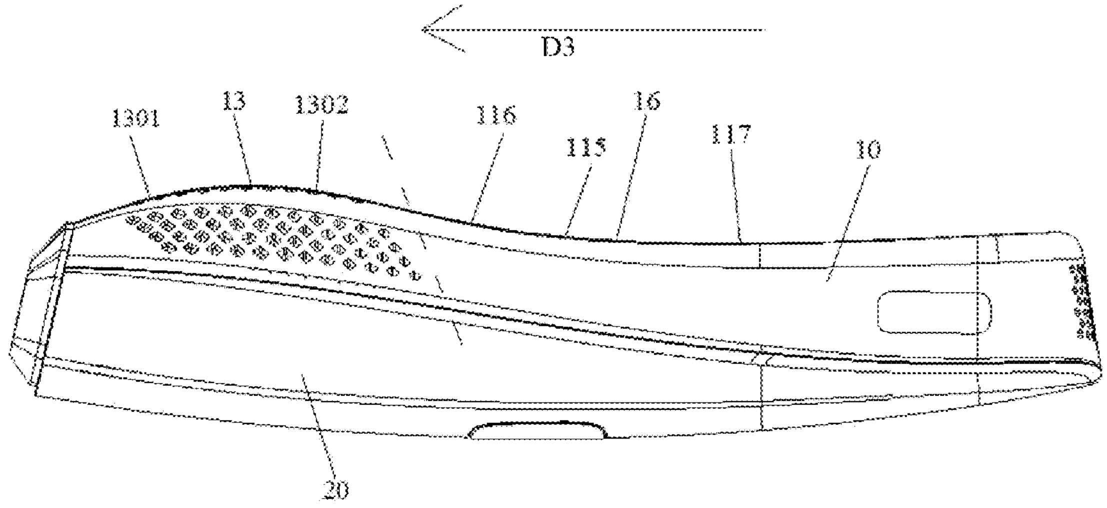
FIG. 49 is a perspective view of the skin treatment apparatus in FIG. 47 from a third perspective.
Figure 50:
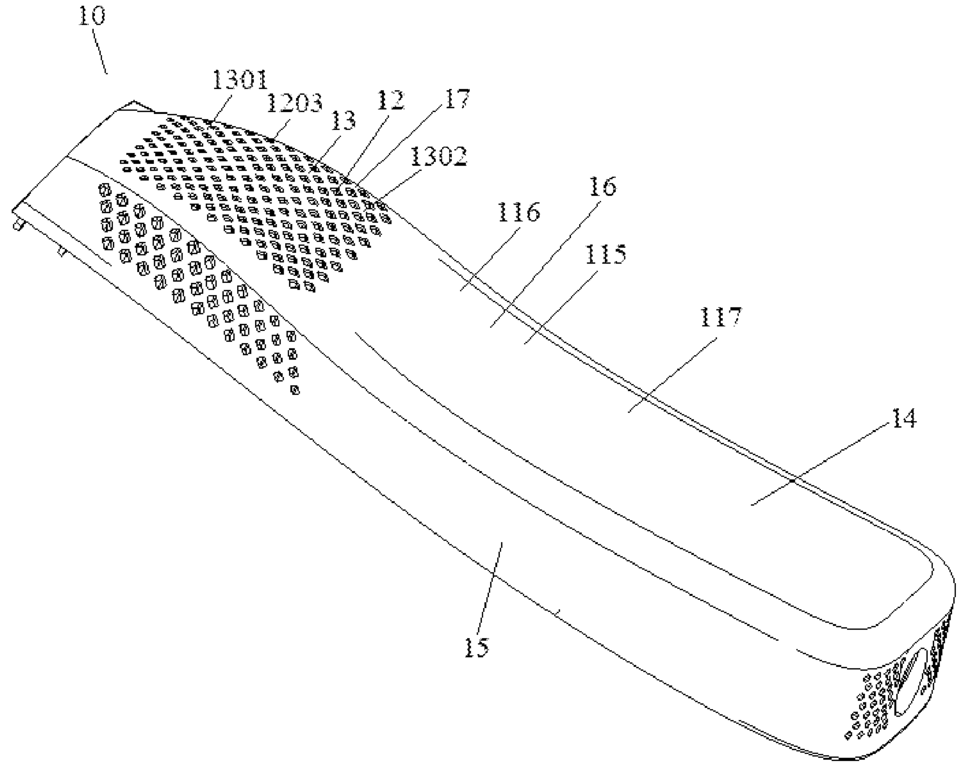
FIG. 50 is a structural schematic diagram of a first housing of the skin treatment apparatus in FIG. 47 from a first perspective.
Figure 51:
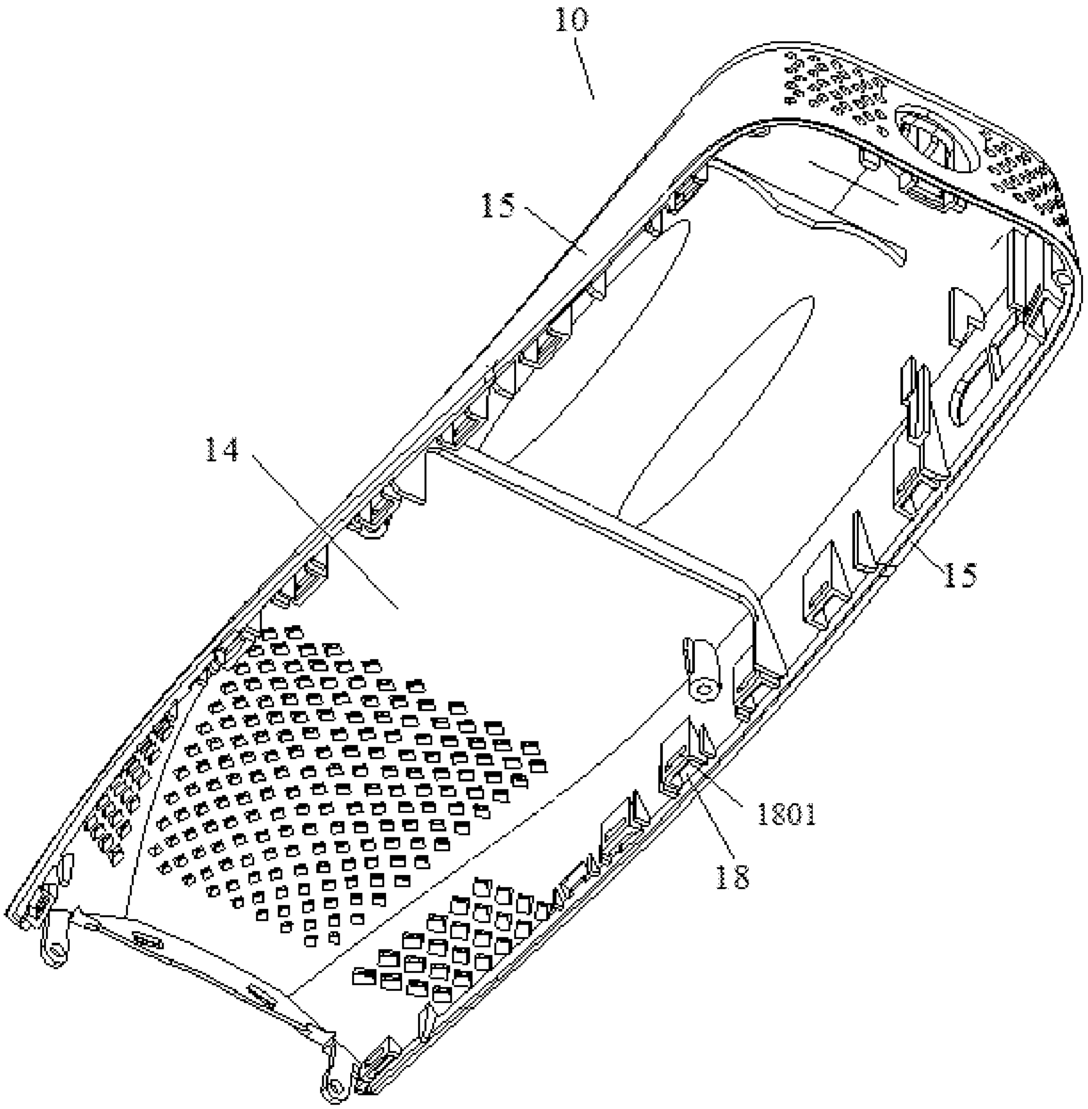
FIG. 51 is a structural schematic diagram of the first housing of the skin treatment apparatus in FIG. 47 from a second perspective.

It should be noted that, as shown in FIG. 49 and FIG. 50, in the direction from the front end to the rear end of the housing component 100, the first wall section 116 being gradually close to the inner cavity of the housing component 100 means that the first wall section 116 is gradually recessed inward, making the inner cavity of the housing component 100 gradually smaller. In this way, the grip area 16 is formed for a user to hold.

It should be noted that the concave part 115 and the first wall section 116 may be formed as a segment of the outer wall surface of the housing component 100 in the circumferential direction, for example, the concave part 115 and the first wall section 116 are formed on the back plate 14. The concave part 115 and the first wall section 116 may be formed to surround the outer wall surface of the housing component 100 in the circumferential direction, that is, the first wall section 116 and the second wall section 117 are formed on the face plate 21, the back plate 14, the first side plate 15 and the second side plate 22 of the housing component 100.

Figure 47:
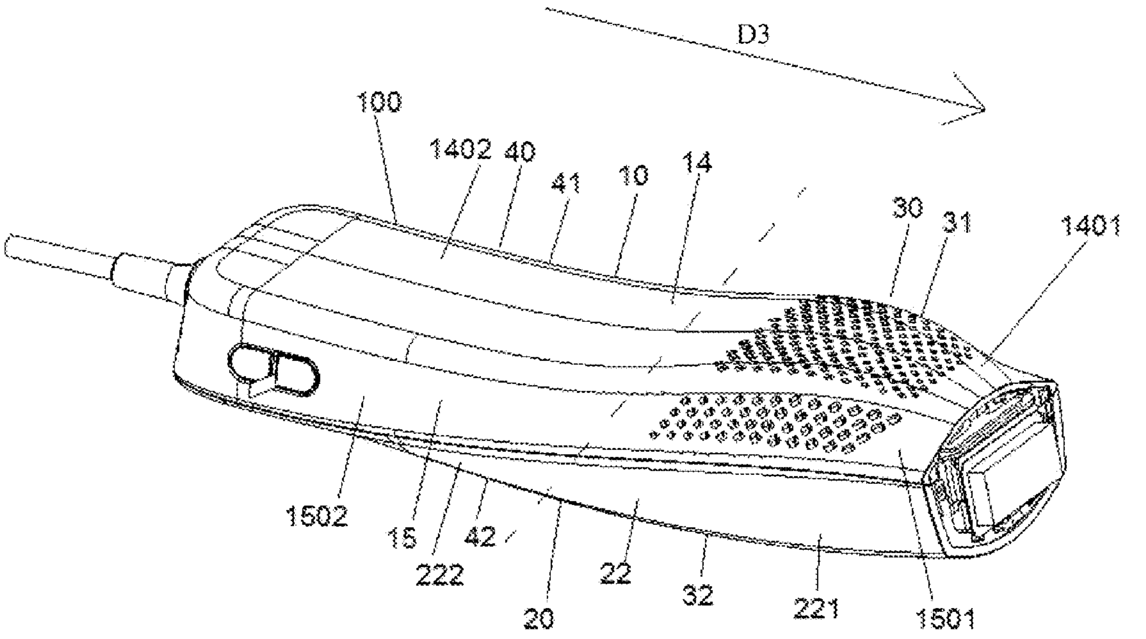
FIG. 47 is a perspective view of a skin treatment apparatus according to an embodiment of the present disclosure from a first perspective.
Figure 48:
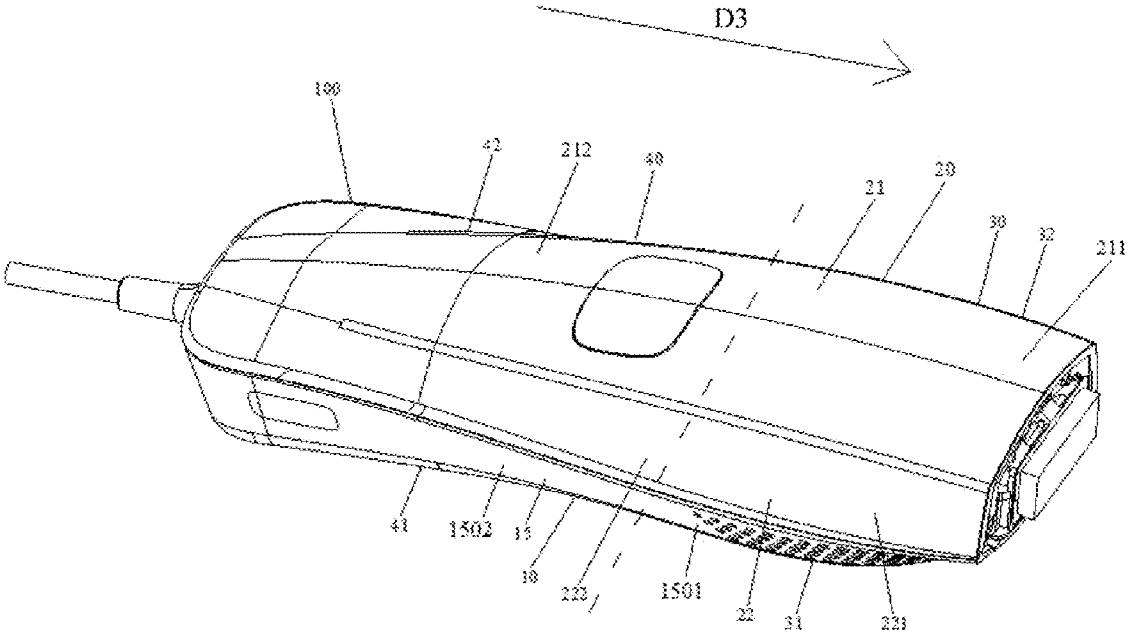
FIG. 48 is a perspective view of the skin treatment apparatus in FIG. 47 from a second perspective.

The arrow direction in FIG. 47 and FIG. 48 is direction from the rear end to the front end of the housing component 100.

According to the skin treatment apparatus of the present disclosure, the concave part 115 is formed on the outer wall surface of the housing component 100, and at least part of the first wall section 116 and at least part of the second wall section 117 of the concave part 115 form the grip area 16, so that a user can hold the grip area 16 during use. Besides, in the direction from the front end to the rear end of the housing component 100, the first wall section 116 is gradually close to the inner cavity of the housing component 100, which increases user comfort.

Moreover, the air vent part 12 is disposed outside the grip area 16 to prevent blocking the air inlet when a user holds the grip area 16. This solves the problem in related art the grip area is prone to blocking the air inlet and thereby affecting the heat dissipation effect of the skin treatment apparatus.

In an embodiment, a first arrangement way of the second wall section 117 is: the second wall section 117 is gradually away from the inner cavity of the housing component 100 in a direction from the front end to the rear end of the housing component 100. A second arrangement way of the second wall section 117: the second wall section 117 is a smooth wall section; where the smooth wall section refers to that the second wall section 117 is basically not raised or recessed in the direction from the front end to the rear end of the housing component 100. A third arrangement way of the second wall section 117 is: the second wall section 117 includes a front half section and a rear half section in a direction from the front end to the rear end of the housing component 100; the front half section of the second wall section 117 is a smooth wall section; the rear half section of the second wall section 117 is gradually away from the inner cavity of the housing component 100 in the direction from the front end to the rear end of the housing component 100; where the smooth wall section refers to that the front half section of the second wall section 117 is basically not raised or recessed in the direction from the front end to the rear end of the housing component 100.

At least part of the second wall section 117 is a smooth wall section, so that a user may hold the apparatus in a slightly backward position.

Optionally, the first wall section 116 is a smooth curved surface, the second wall section 117 is a smooth curved surface, and a smooth transition is provided between the first wall section 116 and the second wall section 117.

In an embodiment, in the length direction D3 of the housing component 100, the air vent part 12 is located on the front side of the grip area 16 close to the housing component 100.

Since the large heat generation structures (such as the light emitting lamp tube and the cooling member) of the skin treatment apparatus are basically disposed at the front end of the housing component 100, the setting in which the air vent part 12 is disposed on the front side of the grip area 16 close to the housing component 100 helps to shorten the air path and thereby improving the heat dissipation effect.

Illustratively, the area on the outer wall surface of the housing component 100 where the air vent part 12 is located is a ventilation area 17. That is, the ventilation area 17 is located on the front side of the grep area 16 close to the housing component 100.

In an embodiment, the grip area 16 is located in the middle of the housing component 100 in the length direction D3 of the housing component 100, or the grip area 16 is disposed close to the middle of the housing component 100 in the length direction D3 of the housing component 100, which is convenient for a user to hold.

In an embodiment, the housing 110 further has an air vent part 12, which includes the housing air outlet part 1201 and the air inlet part 1202. At least part of the housing air outlet part 1201 is located on the side of the air inlet part 1202 away from the grip area 16. It can be understood that the front side of the grip area 16 is provided with the light emitting component 200 and the holder structure for supporting the light emitting component 200. The fan component 300 may be disposed corresponding to the grip area 16, or the fan component 300 may be disposed at the rear side of the grip area 16. In the present disclosure, the air inlet part 1202 is disposed close to the grip area 16, which allows the air inlet part 1202 to be close to the fan 500. This reduces the air inlet path or shorten the air inlet path, thereby improving the heat dissipation effect.

In an embodiment, the housing component 100 includes a first housing 10, including a back plate 14 and two first side plates 15. The two first side plates 15 are respectively connected to two long sides of the back plate 14. Each long side edge of the back plate 14 includes two ends in the length direction of each long side edge of the back plate 14. The distribution direction of two ends of each long side edge of the back plate 14 is the same as the distribution direction of the front end and the rear end of the housing component 100.

Illustratively, the concave part 115 and the air inlet part 1202 are both disposed on the back plate 14. At least part of the housing air outlet part 1201 is disposed on the back plate 14.

Illustratively, a first distribution way of the housing air outlet part 1201 is: the housing air outlet part 1201 is disposed on the back plate 14, and the housing air outlet part 1201 is located on the side of the air inlet part 1202 away from the grip area 16.

Illustratively, a second distribution way of the housing air outlet part 1201 is: the housing air outlet part 1201 includes a first air outlet part 1211 and a second air outlet part 1212. The first air outlet part 1211 is disposed on the back plate 14, and the second air outlet part 1212 is disposed on one of the first side plates 15. The first air outlet part 1211 is located on the side of the air inlet part 1202 away from the grip area 16. At least part of the second air outlet part 1212 is located on the side of the air inlet part 1202 away from the grip area 16.

Illustratively, a third distribution way of the housing air outlet part 1201 is: the housing air outlet part 1201 includes a first air outlet part 1211 and two second air outlet parts 1212. The first air outlet part 1211 is disposed on the back plate 14, and the two second air outlet parts 1212 are disposed on two first side plates 15 respectively. The first air outlet part 1211 is located on the side of the air inlet part 1202 away from the grip area 16. At least part of each second air outlet part 1212 is located on the side of the air inlet part 1202 away from the grip area 16. In this way, by providing the second air outlet parts 1212 on the first side plates 15, on the one hand, the air outlet area is increased, and on the other hand, it is convenient to dispose a better air outlet structure in the housing component 100, thereby improving the heat dissipation effect.

In an embodiment, the outer wall surface of the housing component 100 further includes a bulge part 13. In the length direction D3 of the housing component 100, the bulge part 13 is located on the side of the concave part 115 close to the front end of the housing component 100 (other similar positional relationship described herein may also be called the front side for short). In the direction from the front end to the tail end of the housing component 100, the wall surface of the bulge part 13 includes a third wall section 1301 and a fourth wall section 1302 connected to each other. That is, the third wall section 1301 is located on the front side of the fourth wall section 1302 close to the housing component 100. In the direction from the front end to the rear end of the housing component 100, the third wall section 1301 is gradually away from the inner cavity of the housing component 100, and the fourth wall section 1302 is gradually close to the inner cavity of the housing component 100. The fourth wall section 1302 is connected to the first wall section 116. At least part of the air vent part 12 is disposed on the bulge part 13.

Illustratively, in FIG. 49, the left side of the dashed line is the bulge part 13, and the right side of the dashed line is the concave part 115 and the grip area 16.

It should be noted that the bulge part 13 may be formed as a segment of the outer wall surface of the housing component 100 in the circumferential direction, for example, the bulge part 13 is formed on the back plate 14. The bulge part 13 may also be formed to surround the outer wall surface of the housing component 100 in the circumferential direction, that is, the third wall section 1301 and the fourth wall section 1302 are formed on the face plate 21, the back plate 14, the first side plate 15 and the second side plate 22 of the housing component 100. In this way, the air vent part 12 is disposed on the bulge part 13. On one hand, it makes the indication function of the grip area 16 more obvious; on the other hand, it is possible to form a larger ventilation area, thereby being convenient to set more air vents 1203.

Illustratively, in the length direction D3 of the housing component 100, the bulge part 13 is located on the front side of the grip area 16 close to the housing component 100. In an embodiment, the bulge part 13 is formed on the back plate 14.

In an embodiment, the air inlet part 1202 is disposed on the bulge part 13.

In case the housing air outlet part 1201 is in the first distribution way, the housing air outlet part 1201 is disposed on the bulge part 13. In case the housing air outlet part 1201 is in the second distribution way or the third distribution way, the first air outlet part 1211 is disposed on the bulge part 13.

Optionally, at least part of the housing air outlet part 1201 is disposed on the third wall section 1301. That is, in case the housing air outlet part 1201 is in the first distribution way, at least part of the housing air outlet part 1201 is disposed on the third wall section 1301; in case the housing air outlet part 1201 is in the second distribution way or the third distribution way, at least part of the first air outlet part 1211 is disposed on the third wall section 1301.

Optionally, at least part of the air inlet part 1202 is disposed on the fourth wall section 1302. By disposing the housing air outlet part 1201 on the third wall section 1301 and the air inlet part 1202 on the fourth wall section 1302, the opening orientations of the air outlets on the third wall section 1301 are different from the opening orientations of the air inlets on the fourth wall section 1302. In this way, the probability that the hot air discharged through the air outlets on the third wall section 1301 enters the housing component 100 through the air inlets can be avoided or reduced, thereby improving the heat dissipation efficiency.

In an embodiment, the third wall section 1301 is a smooth curved surface; the fourth wall section 1302 is a smooth curved surface; a smooth transition is provided between the third wall section 1301 and the fourth wall section 1302; and a smooth transition is provided between the fourth wall section 1302 and the first wall section 116. In this way, the skin treatment apparatus is made more beautiful.

In an embodiment, the part of the housing air outlet part 1201 disposed on the back plate 14 is a designated air outlet part 1215. That is, in case the housing air outlet part 1201 is in the first distribution way, the entire housing air outlet part 1201 is the designated air outlet part 1215; in case the housing air outlet part 1201 is in the second distribution way or the third distribution way, the first air outlet part 1211 is the designated air outlet part 1215. The area where the designated air outlet part 1215 is located is the designated air outlet area.

Figure 52:
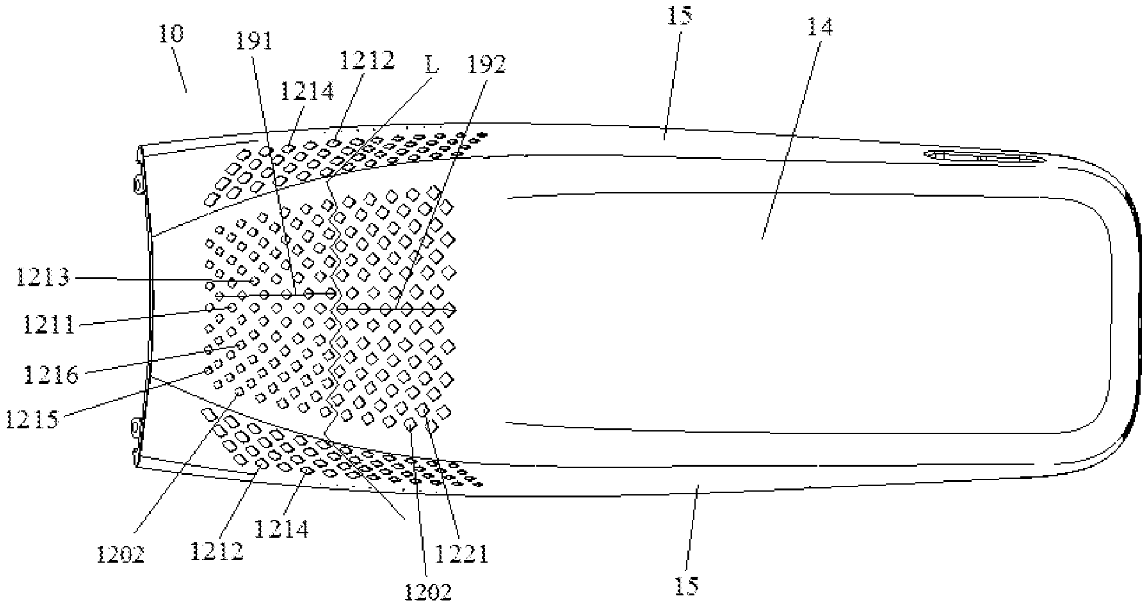
FIG. 52 is a top view of the first housing of the skin treatment apparatus in FIG. 47.
Figure 53:
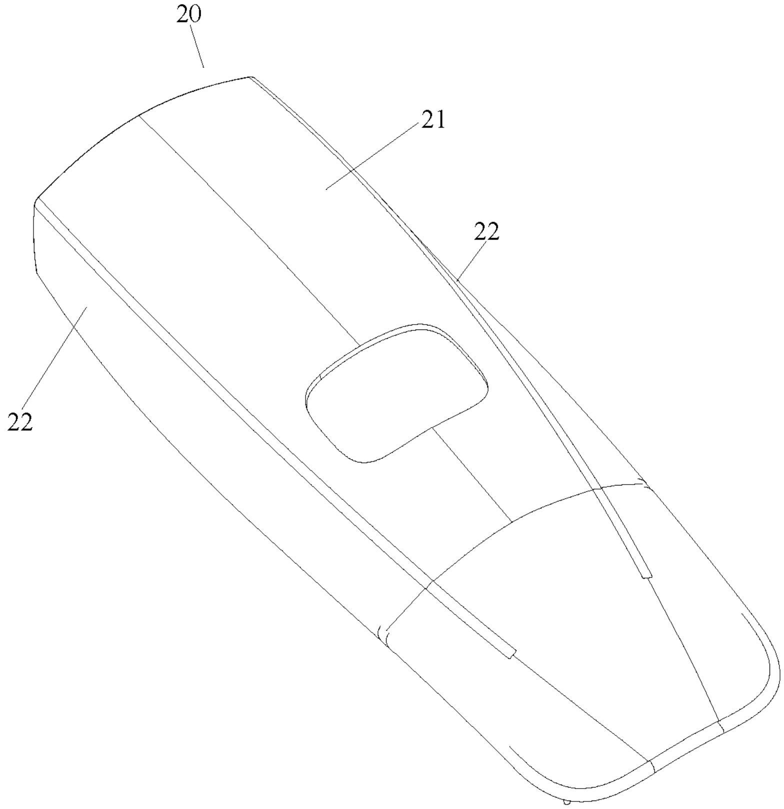
FIG. 53 is a structural schematic diagram of a second housing of the skin treatment apparatus in FIG. 47.

Illustratively, in the length direction D3 of the housing component 100, the designated air outlet part 1215 is located at the front side of the air inlet part 1202 close to the housing component 100. In FIG. 52, the broken line L is taken as the dividing line, where the left side of the broken line L is the designated air outlet part 1215, and the right side of the broken line L is the air inlet part 1202.

Illustratively, the designated air outlet part 1215 includes a plurality of air outlet groups, and each air outlet group includes a plurality of designated air outlets 1216. The plurality of air outlet groups are distributed at intervals along a first direction D1, and the plurality of designated air outlets 1216 of each air outlet group are distributed at intervals along a second direction D2. The first direction D1 and the second direction D2 form an included angle.

Illustratively, any three adjacent air outlet groups are a first air outlet group, a second air outlet group and a third air outlet group. A plurality of designated air outlets 1216 of the first air outlet group are in one-to-one correspondence with a plurality of designated air outlets 1216 of the second air outlet group, and a plurality of designated air outlets 1216 of the first air outlet group are in one-to-one correspondence with a plurality of designated air outlets 1216 of the third air outlet group. That is, the plurality of designated air outlets 1216 of the second air outlet group are in one-to-one correspondence with the plurality of designated air outlets 1216 of the third air outlet group.

Optionally, each designated air outlet 1216 of the first air outlet group, a corresponding designated air outlet 1216 of the second air outlet group, and a corresponding designated air outlet 1216 of the third air outlet group are located on a same straight line. Alternatively, the straight line where each designated air outlet 1216 of the first air outlet group and a corresponding designated air outlet 1216 of the second air outlet group are located forms an included angle with the straight line where a corresponding designated air outlet 1216 of the second air outlet group and the corresponding designated air outlet 1216 of the third air outlet group; that is, each designated air outlet 1216 of the second air outlet group is staggered with the corresponding designated air outlet 1216 of the first air outlet group, and each designated air outlet 1216 of the second air outlet group is staggered with the corresponding designated air outlet 1216 of the third air outlet group. This is beneficial to set more designated air outlets 1216 in the limited designated air outlet area, thereby increasing the air volume of the designated air outlet area. Moreover, compared with increasing the air volume by increasing the ventilation area of the designated air outlet, increasing the air volume by setting more designated air outlets 1216 also allows a densely distributed grid structure formed in the designated air outlet area, preventing external objects from entering the housing component 100.

Figure 6:
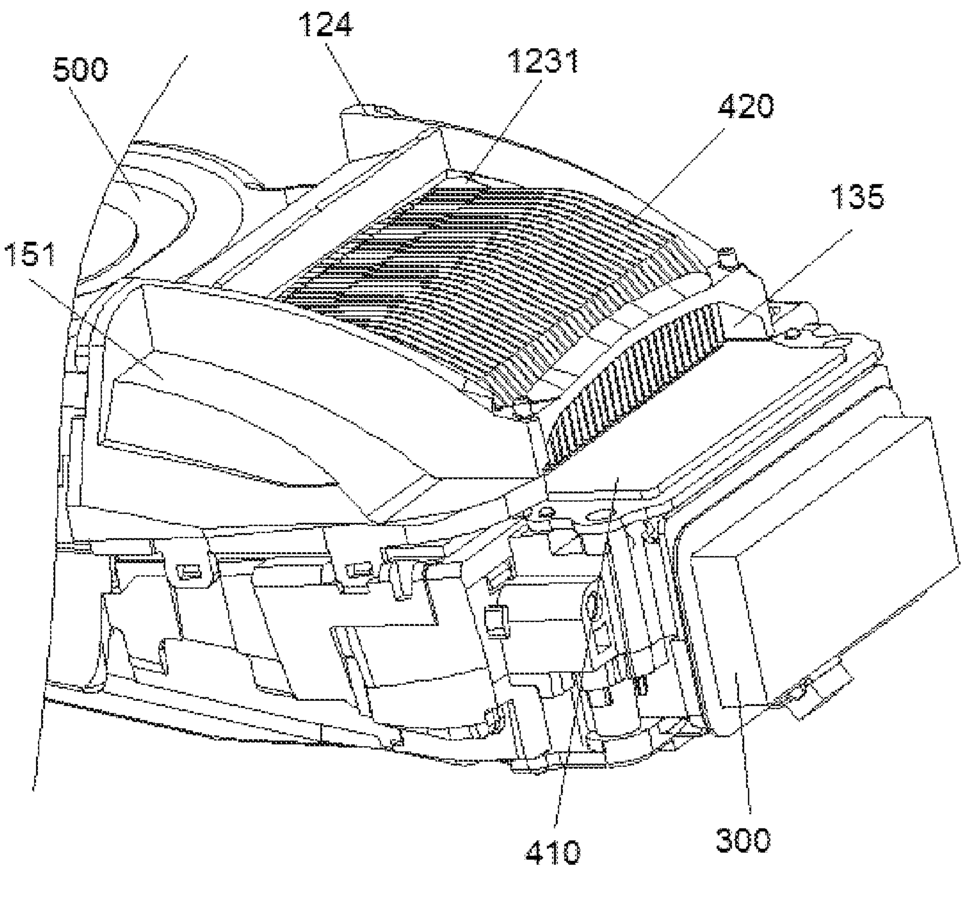
FIG. 6 is a first schematic diagram of an internal structure of the skin treatment apparatus in FIG. 5.

Illustratively, the projection of each designated air outlet 1216 on a first projection plane is a quadrangle, and the first projection plane is perpendicular to an airflow circulation direction of at least one designated air outlet 1216. First diagonal lines of the projections of the plurality of designated air outlets 1216 of each air outlet group on the first projection plane are located on the same straight line. The projection of each designated air outlet 1216 on the first projection plane has two diagonal lines, one of which is the first diagonal line. The first straight line 191 in FIG. 6 is the straight line on which the first diagonal lines of the projections of the plurality of designated air outlets 1216 of one air outlet group on the first projection plane is located.

In an embodiment, the air inlet part 1202 includes a plurality of air inlet groups, and each air inlet group includes a plurality of air inlets 1221. The plurality of air inlet groups are distributed at intervals along a third direction, and the plurality of air inlets 1221 in each air inlet group are distributed at intervals along a fourth direction. The third direction and the fourth direction form an included angle.

Illustratively, any three adjacent air inlet groups are a first air inlet group, a second air inlet group and a third air inlet group. The plurality of air inlets 1221 in the first air inlet group are disposed in one-to-one correspondence with the plurality of air inlets 1221 in the second air inlet group, and the plurality of air inlets 1221 in the first air inlet group are disposed in one-to-one correspondence with the plurality of air inlets 1221 in the third air inlet group. That is, the plurality of air inlets 1221 in the second air inlet group are disposed in one-to-one correspondence with the plurality of air inlets 1221 in the third air inlet group.

Optionally, each air inlet 1221 in the first air inlet group, the corresponding air inlet 1221 in the second air inlet group and the corresponding air inlet 1221 in the third air inlet group are located on a same straight line. Alternatively, the straight line where each air inlet 1221 in the first air inlet group and the corresponding air inlet 1221 in the second air inlet group are located forms an included angle with the straight line where the corresponding air inlet 1221 in the second air inlet group and the corresponding air inlet 1221 in the third air inlet group are located. That is, each air inlet 1221 in the second air inlet group is staggered with respect to the corresponding air inlet 1221 in the first air inlet group, and each air inlet 1221 in the second air inlet group is staggered with respect to the corresponding air inlet 1221 in the third air inlet group. This helps to set more air inlets 1221 in a limited air inlet area, thereby increasing the air volume in the air inlet area. In addition, compared with increasing the ventilation area of the air inlet, setting more air inlets 1221 also allows a densely distributed grid structure formed in the air inlet area, which prevents external objects from entering the housing component 100.

Illustratively, the projection of each air inlet 1221 on a second projection plane is a quadrangle, where the second projection plane is perpendicular to an airflow circulation direction of at least one air inlet 1221. Second diagonal lines of the projections of the plurality of air inlets 1221 in each air inlet group on the second projection plane are on the same straight line. The projection of each air inlet 1221 on the second projection plane has two diagonal lines, one of which is the second diagonal line. The second straight line 192 in FIG. 52 is the straight line on which the second diagonal lines of the projections of the plurality of air inlet 1221 in one air inlet group on the second projection plane is located.

In an embodiment, in case of the first distribution way, the housing air outlet part 1201 includes a plurality of air outlets distributed at intervals, and in this case, each air outlet is a designated air outlet 1216. In case of the second distribution way or the third distribution way, the first air outlet part 1211 includes a plurality of first air outlets 1213 distributed at intervals, and each first air outlet 1213 is a designated air outlet 1216; and the second air outlet part 1212 includes a plurality of second air outlets 1214 distributed at intervals.

In an embodiment, the housing air outlet part 1201 includes a plurality of air vents 1203 distributed at intervals. In case of the first distribution way, the air vents 1203 are collectively referred to as the air inlet 1221 and the air outlet. In case of the second distribution way or the third distribution way, the air vents 1203 are collectively referred to as the air inlet 1221, the first air outlet 1213 and the second air outlet 1214.

Figure 58:
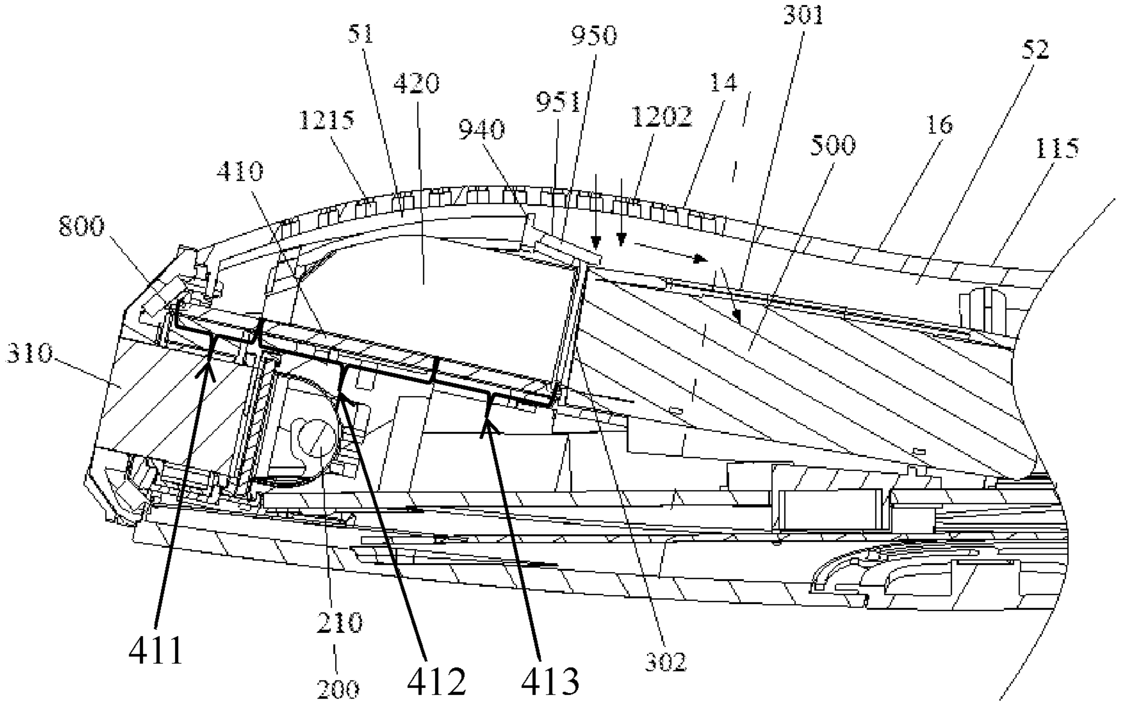
FIG. 58 is a structural schematic diagram of a portion of the skin treatment apparatus in FIG. 57.

As shown in FIG. 58, in the airflow circulation direction of the air vent 1203, the air vent 1203 includes an outer air vent section 1203*a* and an inner air vent section 1203*b* connected and communicated with each other. The ventilation surface of the outer air vent section 1203*a* refers to the section of the outer air vent section 1203*a* perpendicular to the airflow circulation direction of the air vent 1203. The ventilation surface of the inner air vent section 1203*b* refers to the section of the inner air vent section 1203*b* perpendicular to the airflow circulation direction of the air vent 1203.

The first housing 10 is usually processed by using an injection molding technology. The air vent 1203 is formed as the outer air vent section 1203*a* and the inner air vent section 1203*b*. During injection molding, the outer air vent section 1203*a* and the inner air vent section 1203*b* may be formed by using an outer mold section and an inner mold section respectively. In case the length of the air vent is constant, compared with forming the air vents with an integral injection mold, forming the air vent 1203 with the outer mold section and the inner mold section can make the mold release of the outer mold section and the inner mold section easier and more convenient than the mold release of an integral injection mold.

Optionally, the ventilation surface of the outer air vent section 1203*a* is smaller than the ventilation surface of the inner air vent section 1203*b*. This helps to hide the internal structure of the housing component 100, and also makes the appearance of the skin treatment apparatus more beautiful. Moreover, the inner air vent section 1203*b* being formed with a larger ventilation surface is conducive to demolding of the inner mold section.

Optionally, the length of the outer air vent section 1203*a* is less than the length of the inner air vent section 1203*b*, and the length directions of the outer air vent section 1203*a* and the inner air vent section 1203*b* are the same as the airflow circulation direction of the air vent 1203. Therefore, the internal structure of the housing component100 is hidden, and at the same time, the inner air vent section 1203*b* with a larger ventilation surface is allowed to have a larger length, which prevents the ventilation volume of the air vent 1203 from being too small, namely ensuring that the air vent 1203 has a large ventilation volume.

Optionally, in the direction from the inner air vent section 1203*b* to the outer air vent section 1203*a*, the ventilation surface of the outer air vent section 1203*a* gradually increases, to form the outer air vent section 1203*a* into a flaring shape, which is beneficial to demolding of the outer mold section.

In an embodiment, the area on the outer wall surface of the housing component 100 where the designated air outlet part 1215 is located is a first air outlet area. That is, in case the housing air outlet part 1201 is in the first distribution way, all the area on the outer wall surface of the housing component 100 where the designated air outlet part 1215 is located is the first air outlet area; in case the housing air outlet part 1201 is in the second distribution way or the third distribution way, the area on the outer wall surface of the housing component 100 where the first air outlet part 1211 is located is a first air outlet area, and the area on the outer wall surface of the housing component 100 where the second air outlet part 1212 is located is a second air outlet area. The area on the outer wall surface of the housing component 100 where the air inlet part 1202 is located is an air inlet area.

Illustratively, the air inlet of the fan 500 is disposed corresponding to the grip area 16, so that the fan 500 is disposed at the grip area 16. In such a way, there are fewer structures between the air inlet area and the fan 500, thus the air resistance is small; while there are more structures between the air outlet area and the fan 500, thus the air resistance is larger. In case that the air vent area is limited, the size of the air inlet area is smaller than the size of the first air outlet area. That is, the size of the first air outlet area is larger, to increase the velocity rate of the air flow (heat dissipation air) with a great wind resistance in the housing assembly 100, thereby improving the heat dissipation efficiency.

Illustratively, the designated air outlet part 1215 includes a plurality of designated air outlets 1216 distributed at intervals, and the air inlet part 1202 includes a plurality of air inlets 1221 distributed at intervals. The plurality of designated air outlets 1216 include a first part of designated air outlets, that is, the designated air outlet part 1215 includes the first part of designated air outlets. The first part of designated air outlets includes at least one air outlet 1216. The plurality of air inlets 1221 include a first part of air inlets, and the first part of air inlets includes at least one air inlet 1221. The ventilation surface of the designated air outlet 1216 on the outer wall surface of the housing component 100 is smaller than the ventilation surface of the air inlets 1221 on the outer wall surface of the housing component 100.

It should be noted that, in the forging embodiments, the entire housing air outlet part 1201 is disposed on the back plate and located in the non-grip area. In this way, when a user holds the apparatus during use, the air is discharged from the rear side and not blown to the user, thereby improving the user experience.

It should be noted that the housing component 100 may be formed in other ways, such as including a left housing and a right housing, and in this case, the assembled housing component still includes the face plate 21 and the back plate 14. The face plate 21 typically refers to a side plate facing a user's face during use. The face plate 21 may be provided with control buttons, display information, and the like. The back plate 14 typically refers to a side plate facing away from a user's face during use. That is, the housing component 100 includes the face plate 21 and the back plate 14 facing each other. The concave part 115 is disposed on the back plate 14, and at least part of the housing air outlet part 1201 is disposed on the back plate 14.

Illustratively, the distribution direction of the face plate 21 and the back plate 14 is perpendicular to the length direction D3 of the housing component 100.

Illustratively, in the direction from the front end to the rear end of the housing component 100, the first wall section 116 is gradually close to the face plate 21.

Illustratively, in case the second wall section 117 is disposed in the first manner, the second wall section 117 is gradually away from the face plate 21 in the direction from the front end to the rear end of the housing component 100.

Illustratively, in the direction from the front end to the rear end of the housing component 100, the third wall section 1301 is gradually away from the face plate 21, and the fourth wall section 1302 is gradually close to the face plate 21.

In an embodiment, the housing component 100 includes a first housing 10 and a second housing 20 that are detachably connected to each other. The first housing 10 includes the back plate 14, and the second housing 20 includes the face plate 21. The air vent part 12 is disposed on the first housing 10.

In an embodiment, the housing component100 includes a first housing section 30 in the length direction D3 of the housing component100. The part of the first housing 10 on the first housing section 30 is a first housing part 31, and the part of the second housing 20 on the first housing section 30 is a second housing part 32. The air vent part 12 is disposed on the first housing part 31.

Illustratively, the part of the back plate 14 on the first housing part 31 is a first back plate section 1401. The first housing part 31 further includes two first side plate sections 1501, and the two first side plate sections 1501 are connected with two the long side edges of the first back plate section 1401. Each first side plate section 1501 is detachably connected with the second casing 20.

Illustratively, the two first side plate sections 1501 are disposed in a one-to-one correspondence with the two first side plates 15. The part of each first side plate 15 on the first housing part 31 is the corresponding first side plate section 1501. Each first side plate 15 is detachably connected with the second housing 20.

Illustratively, the distribution direction of the two first side plates 15 is perpendicular to the length direction D3 of the housing component 100, and the distribution direction of the two first side plates 15 is perpendicular to the distribution direction of the face plate 21 and the back plate 14.

Illustratively, the air vent part 12 includes a plurality of air inlets 1221 and a plurality of air outlets. The plurality of air inlets 1221 are all disposed on the first back plate section 1401, and at least part of the plurality of air outlets are disposed on the first back plate section 1401.

Optionally, in case the housing air outlet part 1201 is in the first distribution way, the plurality of air outlets are all disposed on the first back plate section 1401. In case the housing air outlet part 1201 is in the second distribution way or the third distribution way, a part of the plurality of air outlets is disposed on the first back plate section 1401, and the other part is disposed on the two first side plate sections 1501. That is, the first air outlet part 1211 is disposed on the first back plate section 1401, and the second air outlet part 1212 is disposed on at least one first side plate section 1501.

In an embodiment, in the length direction D3 of the housing component 100, the housing component 100 further includes a second housing section 40 connected to the first housing section 30. The first housing section 30 is located on the side of the second housing section 40 close to the front end of the housing component 100.

Illustratively, the part of the first housing 10 on the second housing section 40 is a third housing part 41, and the part of the second housing 20 on the second housing section 40 is a fourth housing part 42. The first housing 10 includes a first housing part 31 and a third housing part 41 connected to each other. The second housing 20 includes a second housing part 32 and a fourth housing part 42 connected to each other.

Illustratively, the part of the back plate 14 on the third housing part 41 is a second back plate section 1402. The back plate 14 includes a first back plate section 1401 and a second back plate section 1402 connected to each other.

Illustratively, the third housing part 41 further includes two second side plate sections 1502, and the two second side plate sections 1502 are respectively connected to two long sides of the second back plate section 1402. Each second side plate section 1502 is detachably connected to the second housing 20.

Illustratively, the two second side plate sections 1502 are disposed in a one-to-one correspondence with the two first side plates 15, and the part of each first side plate 15 on the third housing part 41 is the corresponding second side plate section 1502. That is, each first side plate 15 includes a first side plate section 1501 and a second side plate section 1502 connected to each other.

In an embodiment, the part of the face plate 21 on the second housing part 32 is a first face plate section 211. The second housing part 32 further includes two third side plate sections 221, and the two third side plate sections 221 are respectively connected to two long sides of the first face plate section 211. Each third side plate section 221 is detachably connected to the first housing 10.

Illustratively, the second housing 20 further includes two second side plates 22, and the two second side plates 22 are respectively connected with two long sides of the face plate 21. The two third side plate sections 221 are disposed in one-to-one correspondence with the two second side plates 22, and the part of each second side plate 22 on the second housing part 32 is the corresponding third side plate section 221. Each second side plate 22 is detachably connected to the first housing 10.

Illustratively, the distribution direction of the two second side plates 22 is perpendicular to the length direction D3 of the housing component 100, and the distribution direction of the two second side plates 22 is perpendicular to the distribution direction of the face plate 21 and the back plate 14.

Illustratively, the part of the face plate 21 on the fourth housing part 42 is a second face plate section 212. The face plate 21 includes a first face plate section 211 and a second face plate section 212 connected to each other.

Illustratively, the fourth housing part 42 further includes two fourth side plate sections 222, and the two fourth side plate sections 222 are respectively connected with two long sides of the second face plate section 212. Each fourth side plate section 222 is detachably connected with the first housing 10.

Illustratively, the two fourth side plate sections 222 are disposed in a one-to-one correspondence with the two second side plates 22, and the part of each second side plate 22 on the fourth housing part 42 is the corresponding fourth side plate section 222. That is, each second side plate 22 includes a third side plate section 221 and a fourth side plate section 222 connected to each other.

Illustratively, in FIG. 47 and FIG. 48, the left side of the dashed line is the second housing section 40, and the right side of the dashed line is the first housing section 30.

In an embodiment, the second housing 20 is an integrally formed structure, and the first housing 10 is an integrally formed structure.

In an embodiment, each first side plate section 1501 includes a first end connected with the first back plate section 1401 and a second end connected with the second housing 20. In the direction from the first end to the second end of each first side plate sections 1501, each first side plate section 1501 is gradually away from the other first side plate section 1501. That is, in the direction from the first end to the second end of each first side plate section 1501, each first side plate section 1501 gradually expands outward in the direction away from the inner cavity of the housing component 100. In this way, the skin treatment apparatus as a whole can be made to air out to the back side, and it is advantageous to increase the air outlet area.

In an embodiment, each third side plate section 221 includes a first end connected with the first face plate section 211 and a second end connected with the first housing 10. In the direction from the first end to the second end of each third side plate section 221, each third side plate section 221 is gradually away from the other third side plate section 221. That is, in the direction from the first end to the second end of each third side plate section 221, each third side plate section 221 gradually expands outward in the direction away from the inner cavity of the housing component 100. In this way, each third side plate section fits the first housing 10.

In an embodiment, each first side plate 15 includes a first end connected with the back plate 14 and a second end connected with the second housing 20. In the direction from the first end to the second end of each first side plate 15, each first side plate 15 is gradually away from the other first side plate 15, so that each first side plate 15 expands outward in the direction away from the other first side plate 15. In the direction from the rear end to the front end of the housing component 100, the expansion degree of each first side plate 15 gradually increases at the grip area 16 and the bulge part 13. That is, the angle of expansion of each first side plate 15 gradually increases.

According to the above design, the expansion degree of the first side plate 15 at the bulge part 13 is relatively large, so that the width of the first side plate 15 at the bulge part 13 is relatively large, and the plate surface of the first side plate 15 at the bulge part 13 is relatively large. Therefore, the area of the second air exhaust area can be set to be relatively large; that is, it is convenient to arrange more second air outlets 1214.

Illustratively, the width direction of the first side plate 15 is perpendicular to the length direction D3 of the housing component 100.

In addition, the expansion degree of the first side plate 15 at the grip area 16 is smaller than the expansion degree of the first side plate 15 at the bulge part 13, so that the convex edge at the joint of the first side plate and the second housing at the grip area 16 is allowed to be not obvious, which increases user comfort.

In an embodiment, each the second side plate 22 includes a first end connected with the face plate 21 and a second end connected with the first housing 10; in the direction from the first end of each the second side plate 22to the second end, each the second side plate 22 is gradually away from the other second side plate 22, so that each the second side plate 22 expands outward in the direction away from the other second side plate 22; and in the direction from the rear end of the housing component 100 to the front end, the expansion degree of each second side plate 22 gradually decreases at the grip area 16 and the bulge part 13.

Figure 54:
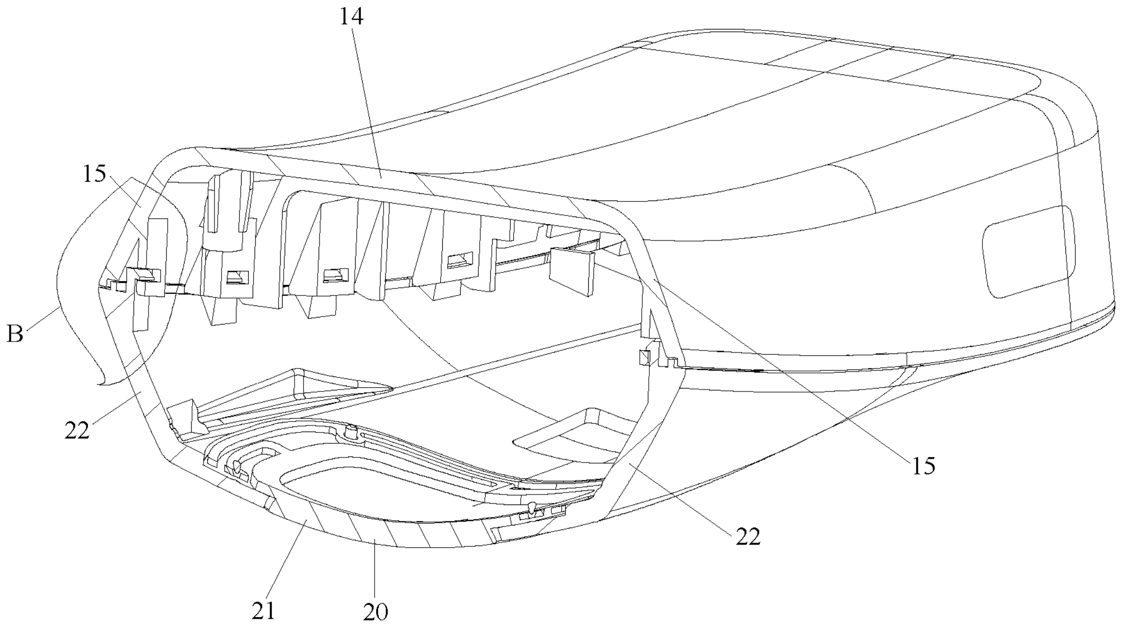
FIG. 54 is a longitudinal sectional diagram of a first housing and a second housing of the skin treatment apparatus in FIG. 47 in assembly.

In an embodiment, as shown in FIG. 54, one of the first housing 10 and the second housing 20 is provided with an insertion part 23, and the other one is provided with an insertion groove 18. The insertion part 23 is inserted into the insertion groove 18, so that the first housing 10 is detachably connected to the second housing 20.

Figure 55:
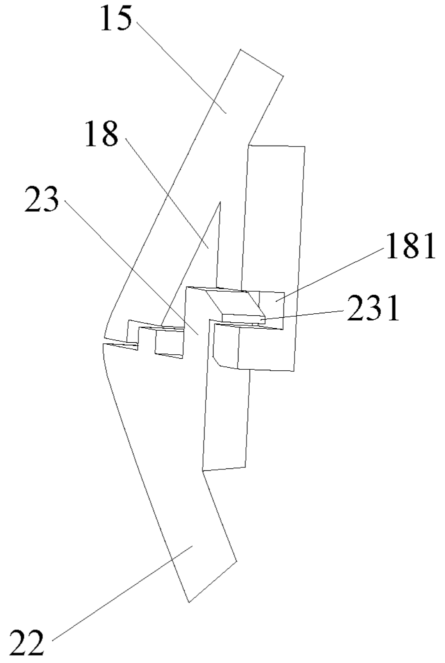
FIG. 55 is an enlarged view of portion B of the assembly of the first housing and the second housing of the skin treatment apparatus in FIG. 54.

Illustratively, as shown in FIG. 55, the side wall of the insertion groove 18 is defined with a latching hole 1801, and the side wall of the insertion part 23 is protruded with a latching platform 231, so that when the insertion part 23 is inserted into the insertion groove 18, the latching platform 231 is latched into the latching hole 1801, to ensure a stable connection between the first housing 10 and the second housing 20.

Optionally, a plurality of insertion parts 23 and a plurality of insertion grooves 18 are provided. The plurality of insertion parts 23 are inserted into the plurality of insertion grooves 18 in a one-to-one correspondence.

Illustratively, each second side plate 22 is provided with at least one insertion part 23; and/or, each second side plate 22 is provided with at least one insertion groove 18.

Illustratively, each first side plate section 1501 is provided with at least one insertion part 23; and/or, each first side plate section 1501 is provided with at least one insertion groove 18.

Figure 56:
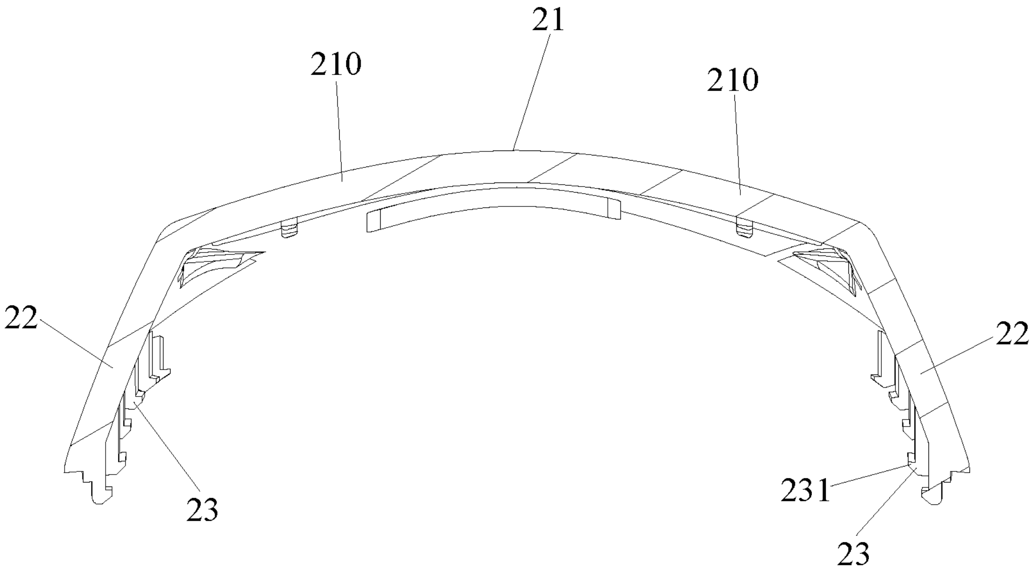
FIG. 56 is a longitudinal sectional diagram of the second housing of the skin treatment apparatus in FIG. 53.

In an embodiment, as shown in FIG. 56, the face plate 21 includes two face plate parts 210 connected to each other. The long side edges of the two face plate parts 210 are connected to each other. Each face plate part 210 includes a first end connected to the other face plate part 210 and a second end away from the other face plate part 210. In the direction from the second end to the first end of each face plate part 210, the face plate part 210 is gradually away from the back plate 14.

Illustratively, a distribution direction of the two face plate parts 210 is perpendicular to the length direction D3 of the housing component 100, and the distribution direction of the two face plate parts 210 is perpendicular to a distribution direction of the face plate 21 and the back plate 14.

Illustratively, the face plate 21 is an arc-shaped plate. The face plate 21 protrudes toward the direction away from the back plate 14.

Figure 57:
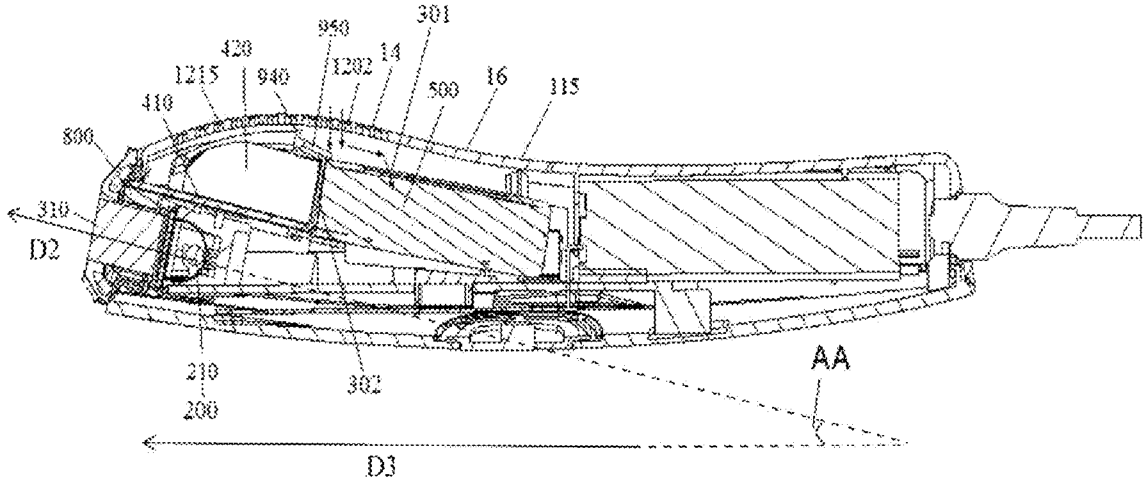
FIG. 57 is a side view of a longitudinal section of the skin treatment apparatus in FIG. 49.

In an embodiment, as shown in FIG. 57, the skin treatment apparatus further includes the fan 500. The fan 500 is defined with an air inlet. The fan 500 is disposed in the housing component 100, and the air inlet of the fan 500 is disposed corresponding to the grip area 16. In this way, the fan 500 is disposed adjacent to the air inlet part 1202, which is easier to suck the outside air.

In other embodiments, the air inlet part 1202 may be disposed on the side of the grip area 16 close to the rear end of the housing component 100. That is, the housing air outlet part 1201 and the air inlet part 1202 are disposed on the front and rear sides of the grip area 16, respectively.

Further, the part of the housing air outlet part 1201 disposed on the back plate 14 is the designated air outlet part 1215, which is located on the side of the air inlet part 1202 away from the grip area 16. The skin treatment apparatus further includes the fan 500, which is provided with the air inlet and the air outlet. The inner cavity of the housing component 100 includes a first area 51 and a second area 52. The designated air outlet part 1215 and the air inlet part 1202 are both disposed corresponding to the first area 51, and the grip area 16 is disposed corresponding to the second area 52. At least part of the fan 500 is disposed in the second area 52. The air inlet of the fan 500 is located in the second area 52. The air inlet of the fan 500 faces the grip area 16. The air outlet of the fan 500 faces the first area 51. In this way, the structural layout in the housing component 100 is more reasonable.

Illustratively, the lower side of the dotted line in FIG. 58 is the first area 51, and the upper side of the dotted line is the second area 52.

Optionally, a part of the fan 500 is disposed in the second area 52, and the other part of the fan 500 is disposed in the first area 51.

The air intake port 301 in FIG. 57 and FIG. 58 is the air inlet of the fan 500, and the air exhaust port 302 is the air outlet of the fan 500.

In an embodiment, as shown in FIG. 57 and FIG. 58, the skin treatment apparatus further includes a partition part 940. The partition part 940 is disposed in the first area 51, and the partition part 940 is located at the junction of the designated air outlet part 1215 and the air inlet part 1202, so that the airflow flowing from the air inlet part 1202 flows to the second area 52 and then flows into the fan 500 through the air inlet of the fan 500.

Illustratively, the partition part 940 and the back plate 14 form a preset included angle, which ranges from 80 degrees to 100 degrees. The preset included angle faces the second area 52.

Illustratively, the partition part 940 is a plate-like structure.

Illustratively, as shown in FIG. 58, the partition part 940 is disposed on the heat dissipation holder 402.

In an embodiment, as shown in FIG. 57 and FIG. 58, the skin treatment apparatus further includes a drainage part 950 connected to the partition part 940. The drainage part 950 is located on the side of the partition part 940 facing the second area 52, to drain the airflow flowing from the air inlet part 1202 to the second area 52 through the drainage part 950. The arrows in FIG. 57 and FIG. 58 show that, under the action of the partition part 940 and the drainage part 950, the airflow entering from the air inlet part 1202 is directed to the second area 52 and then flows into the fan 500 through the air inlet of the fan 500.

Illustratively, the surface of the drainage part 950 facing the back plate 14 is a drainage surface 951. The drainage surface 951 includes a connection end connected with the partition part 940 and a free end away from the partition part 940. The drainage surface 951 is gradually away from the back plate 14 in the direction from the connection end of the drainage surface 951 to the free end.

Illustratively, the partition part 940 includes a first end connected to the back plate 14 and a second end away from the back plate 14. The connection end of the drainage surface 951 is located between the first end and the second end of the partition part 940.

The space between the drainage surface 951 and the back plate 14 and located on the side of the partition part 940 facing the second area 52 is an air intake space 952. The setting in which the preset included angle ranges from 80 degrees to 100 degrees, the connection end of the drainage surface 951 is located between the first end and the second end of the partition part 940, and the drainage surface 951 is gradually away from the back plate 14 in the direction from the connection end to the free end of the drainage surface 951 allows the air intake space 952 to be larger, which is beneficial to increase the air intake flow.

Illustratively, the free end of the drainage surface 951 extends to the fan 500 in the direction from the first area 51 to the second area 52. In this way, all the airflow flowing in through the air inlet part 1202 can be drained to the fan 500, thereby ensuring that more airflow flows into the fan 500.

Illustratively, the drainage part 950 is a plate-shaped structure, and the plate surface of the drainage part 950 facing the back plate 14 is the drainage surface 951.

From the above description, it can be seen that the foregoing embodiments have the following technical effects:

The heat generated by the cold compress component is conducted to the second thermal conductive section through the first thermal conductive section, and then is dissipated through the heat dissipation sheet component thermally connected to the second thermal conductive section. In the present disclosure, since the second thermal conductive section thermally connected to the heat dissipation sheet component is disposed corresponding to the light emitting component, the heat dissipation sheet component is disposed close to the cold compress component, the thermal conductive path is shortened. In other words, the heat dissipation sheet component and the light emitting component are stacked in the thickness direction of the housing component. Compared with the related art in which the cold compress component, the light emitting component and the heat dissipation sheet component are arranged along a straight line, the skin treatment apparatus of the present disclosure shortens the overall length of the thermal conductive structure and accordingly shortens the thermal conductive path, which allows the heat dissipation sheet component to be closer to the light emitting component, thereby improving the heat dissipation efficiency. Therefore, the problem in related art that the length of the thermal conductive component of the skin treatment apparatus is relatively long and thereby affecting the heat dissipation efficiency of the heat dissipation sheet component is solved.

Obviously, the foregoing embodiments are only part of the embodiments of the present disclosure and not all of them. Based on the embodiments in the present disclosure, all other embodiments obtained by those skilled in the art without creative working shall fall within the scope of protection in the present disclosure.

It should be noted that the terms used herein are intended to describe specific embodiments and are not intended to limit exemplary embodiments under the present disclosure. As used herein, the singular form is also intended to include the plural form unless the context expressly indicates otherwise. In addition, it should be understood that the terms "include" and/or "comprise" used in this specification indicate the presence of features, steps, operations, devices, components and/or combinations thereof.

It should be noted that the terms "first", "second", etc. in the description and claims of the present disclosure and in the drawings are used to distinguish similar objects and are not necessarily used to describe a particular order or sequence. It should be understood that the data thus used are interchangeable where appropriate so that the embodiments of the present disclosure described herein can be implemented in an order other than those illustrated or described herein.

The preferred embodiments of the present disclosure are described above and are not intended to limit the present disclosure. For those skilled in the art, the present disclosure is subject to various changes and variations. Any modification, equivalent replacement, improvement, etc. made within the spirit and principles of the present disclosure shall be included in the scope of protection of the present disclosure.

What is claimed is:

1. A skin treatment apparatus, comprising:

a housing component (100) defined with an accommodation cavity and a light outlet (11) communicated with each other;

a light emitting component (200) disposed in the accommodation cavity, light generated from the light emitting component (200) passing through the light outlet (11) and being irradiated to a skin to be treated;

a cold compress component (300) disposed on the housing component (100) and located at the light outlet (11), the cold compress component (300) being configured to cool the skin to be treated or a skin in a vicinity of the skin to be treated; and a heat dissipation component (400) comprising a thermal conductive structure (410) and a heat dissipation sheet component (420), the thermal conductive structure (410) comprising a first thermal conductive section (411) and a second thermal conductive section (412), the cold compress component (300) being thermally connected to the first thermal conductive section (411), and at least part of the heat dissipation sheet component (420) being thermally connected to the second thermal conductive section (412)

wherein the housing component (100) comprises:

a housing (110), the light outlet (11) being located at a first end of the housing (110), and the first end of the housing (110) being provided with a necking section (111);

wherein a height of at least part of the heat dissipation sheet component (420) gradually reduces along the light output direction of the light emitting component (200), to fit the necking section (111);

wherein the heat dissipation sheet component (420) comprises a first side surface (421) and a second side surface (422), the first side surface (421) faces the first end of the housing (110), the second side surface (422) faces away from the light emitting component (200), a joint of the first side surface (421) and the second side surface (422) is defined with a missing corner (423), and the missing corner (423) is disposed corresponding to the necking section (111);

wherein the heat dissipation sheet component (420) further comprises a transition surface (424), the first side surface (421) is connected to the second side surface (422) by the transition surface (424), the transition surface (424) is non-coplanar with the first side surface (421), the transition surface (424) is non-coplanar with the second side surface (422), and the missing corner (423) is formed between the transition surface (424) and the housing (110);

wherein the heat dissipation sheet component (420) comprises a plurality of heat dissipation sheets (425) arranged at intervals in a first direction, a first side edge of each heat dissipation sheet (425) forms the first side surface (421), and a second side edge of each heat dissipation sheet (425) forms the second side surface (422); wherein, each heat dissipation sheet (425) extends along a second direction, the first direction is non-parallel to the second direction, and the second direction is the same as the light output direction of the light emitting component (200);

wherein the transition surface (424) comprises a first sub-transition surface (4241) and a second sub-transition surface (4242) which is non-coplanar with the first sub-transition surface (4241), the first sub-transition surface (4241) is connected to the first side surface (421), and the second sub-transition surface (4242) is connected to the second side surface (422); and each heat dissipation sheet (425) comprises:

a heat dissipation sheet body (4251) comprising the first side surface (421), the second side surface (422), and the second sub-transition surface (4242); and a flange (4252) disposed on the heat dissipation sheet body (4251) and non-coplanar with the heat dissipation sheet body (4251), a surface of the flange (4252) away from the heat dissipation sheet body (4251) forming the first sub-transition surface (4241);

wherein, a ventilation channel (4253) is formed between the heat dissipation sheet bodies (4251) of two adjacent heat dissipation sheets (425), and the flange (4252) of each heat dissipation sheet (425) is in contact with an adjacent heat dissipation sheet (425) and configured to block at least part of the ventilation channel (4253), so as to form an air outlet (427) on two sides of the flange (4252).

2. The skin treatment apparatus according to claim 1, wherein the housing component (100) is provided with a housing air outlet part (1201), and at least part of the heat dissipation component (400) is disposed corresponding to the housing air outlet part (1201); and/or, the thermal conductive structure (410) extends along a light output direction of the light emitting component (200); and/or, the thermal conductive structure (410) comprises a capillary flow channel and a thermal conductive medium disposed in the capillary flow channel, the first thermal conductive section (411) is an evaporation section, and the second thermal conductive section (412) is a condensing section.

3. The skin treatment apparatus according to claim 1, wherein the heat dissipation sheet component (420) further comprises:

a blocking part disposed on a part of a third side edge of at least one heat dissipation sheet (425) for blocking at least part of the ventilation channel (4253); a surface of the blocking part away from the light emitting component (200) forming the first sub-transition surface (4241), so as to form the air outlet (427) at two sides of the blocking part; wherein the other part of the third side edge of the at least one heat dissipation sheet (425) forms the second sub-transition surface (4242).

4. The skin treatment apparatus according to claim 1, wherein a ventilation channel (4253) is formed between two adjacent heat dissipation sheets (425), the heat dissipation sheet component (420) is defined with an air inlet and an air outlet (427), the air inlet is communicated with the air outlet (427) through the ventilation channel (4253), the air inlet is located on a side of the heat dissipation sheet component (420) away from the first side surface (421), and the air outlet (427) is located on at least one of the first side surface (421), the second side surface (422), and the missing corner (423).

5. The skin treatment apparatus according to claim 1, wherein the heat dissipation component (400) is located on one side of the light emitting component (200); and/or the thermal conductive structure (410) is a vapor chamber or a heat pipe, and the heat dissipation sheet component (420) and the light emitting component (200) are located on two opposite sides of the thermal conductive structure (410); and/or the thermal conductive structure (410) further comprises a third thermal conductive section, the third thermal conductive section is connected to an end of the second thermal conductive section (412) away from the first thermal conductive section (411), the third thermal conductive section protrudes from the light emitting component (200) in a direction opposite to the light output direction of the light emitting component (200), and the heat dissipation sheet component (420) is further disposed on the third thermal conductive section; and/or the cold compress component (300) comprises a light transmitting member (310) and a cooling plate (800), the light transmitting member (310) is disposed on the housing component (100), the light transmitting member (310) is located on a side of the light emitting component (200) facing the light outlet (11) and is disposed corresponding to the light outlet (11), the light transmitting member (310) is configured to transmit the light generated by the light emitting component (200) out of the light outlet (11), the cooling plate (800) comprises a cooling surface and a heat dissipation surface, the cooling surface is thermally connected to the light transmitting member (310), and the heat dissipation surface is thermally connected to the first thermal conductive section (411); and/or a length direction of the housing component (100) and the light output direction of the light emitting component (200) form an included angle, and the included angle is greater than or equal to 6 degrees and less than or equal to 36 degrees.

6. The skin treatment apparatus according to claim 1, wherein the housing (110) comprises:

a first side plate (112) located on a side of the heat dissipation sheet component (420) away from the light emitting component (200); and a second side plate (113) facing the first side plate (112);

wherein, a surface of the first side plate (112) facing a second side surface (422) of the heat dissipation sheet component (420) defines a first extension section (1121), and at least part of the first extension section (1121) gradually bends toward the second side plate (113) along the light output direction of the light emitting component (200), to form at least part of the necking section (111).

7. The skin treatment apparatus according to claim 6, wherein the housing component (100) further comprises:

a holder component (120) disposed in the accommodation cavity, the holder component (120) being defined with a first mounting cavity (121) and a second mounting cavity (122), the light emitting component (200) being disposed in the first mounting cavity (121), the heat dissipation sheet component (420) being disposed in the second mounting cavity (122), and at least part of a projection of the second mounting cavity (122) on the first mounting cavity (121) being within the first mounting cavity (121) along a length direction of the housing component (100).

8. The skin treatment apparatus according to claim 7, wherein the holder component (120) comprises a first ventilation surface (123) facing the first extension section (1121), and at least part of the first ventilation surface (123) is gradually close to the second side plate (113) along the light output direction of the light emitting component (200), to fit the first extension section (1121); wherein, the first ventilation surface (123) is defined with a first air vent (1231) communicated with the second mounting cavity (122).

9. The skin treatment apparatus according to claim 8, wherein the holder component (120) comprises a heat dissipation sheet holder (124) and a light emitting side holder (125) located on two sides of the thermal conductive structure (410) and connected to each other, the light emitting side holder (125) is provided with the first mounting cavity (121), the heat dissipation sheet holder (124) is provided with the second mounting cavity (122), the first ventilation surface (123), and a mounting port (1241); and the heat dissipation sheet component (420) is mounted in the second mounting cavity (122) through the mounting port (1241).

10. The skin treatment apparatus according to claim 9, further comprising:

a fan (500) disposed in the accommodation cavity and located on a side of the heat dissipation sheet component (420) away from the light outlet (11);

wherein, the heat dissipation sheet holder (124) is defined with a second air vent (1242), and an air outlet of the fan (500) is communicated with the second mounting cavity (122) through the second air vent (1242).

11. The skin treatment apparatus according to claim 10, wherein the cold compress component (300) comprises a light transmitting member (310), the light emitting side holder (125) is further defined with a third mounting cavity (1251) located between the first mounting cavity (121) and the light outlet (11), and the light transmitting member (310) is mounted in the third mounting cavity (1251).

12. The skin treatment apparatus according to claim 10, wherein the heat dissipation sheet holder (124) comprises a first holder, the first holder comprises a first support part (131), a first side support part (132), a second support part (133), and a second side support part (134) connected with each other successively, the first support part (131) and the second support part (133) face each other and are connected to the second side support part (134), the first side support part (132) faces the second side support part (134), and the second support part (133) is disposed away from the light outlet (11) with respect to the first support part (131);

wherein, the first support part (131), the first side support part (132), the second support part (133), and the second side support part (134) enclose to form the second mounting cavity (122) and the first air vent (1231); side walls of the first support part (131), the first side support part (132), the second support part (133), and the second side support part (134), that are away from the light emitting component (200), form the first ventilation surface (123); the second support part (133), the first side support part (132), and the second side support part (134) enclose to form the second air vent (1242).

13. The skin treatment apparatus according to claim 12, wherein the first support part (131) comprises a first support plate (1311) disposed laterally, the second support part (133) comprises a second support plate (1331) disposed laterally, the first side support part (132) comprises a third support plate (1321) disposed longitudinally, and the second side support part (134) comprises a fourth support plate (1341) disposed longitudinally; one end of the second support plate (1331) is connected to an inner surface of the third support plate (1321), and the other end of the second support plate (1331) is connected to an inner surface of the fourth support plate (1341); a side edge of the second support plate (1331) facing the fan (500), a side edge of the third support plate (1321) facing the fan (500), and a side edge of the fourth support plate (1341) facing the fan (500) enclose to form the second air vent (1242); a side edge of the first support plate (1311) facing the third support plate (1321), the third support plate (1321), the fourth support plate (1341), and a side edge of the second support plate (1331) facing the first support plate (1311) enclose to form the first air vent (1231).

14. The skin treatment apparatus according to claim 11, wherein the light emitting side holder (125) comprises a second holder (1252) and a third holder (1253) located between the second holder (1252) and the light outlet (11); the second holder (1252) is provided with the first mounting cavity (121) and a holder light outlet (1252*a*), and the first mounting cavity (121) is communicated with the light outlet (11) through the holder light outlet (1252*a*); the third holder (1253) is connected to the second holder (1252) and is provided with the third mounting cavity (1251).

* * * * *